US011866501B2

(12) United States Patent
Herrmann et al.

(10) Patent No.: US 11,866,501 B2
(45) Date of Patent: Jan. 9, 2024

(54) ANTI-TRKB ANTIBODIES

(71) Applicant: Boehringer Ingelheim International GmbH, Ingelheim am Rhein (DE)

(72) Inventors: Rolf Herrmann, Biberach (DE); Remko Alexander Bakker, Biberach an der Riss (DE); Sebastian Bandholtz, Schemmerhofen (DE); Peter Michael Benz, Veitshoechheim (DE); Michael Dziegelewski, Newburgh, NY (US); Lore Katharina Florin, Redwood City, CA (US); Cynthia Hess Kenny, Pearl River, NY (US); Sarah Kathleen Low, Carmel, NY (US); Holger Rosenbrock, Mittelbiberach (DE); Sanjaya Singh, Blue Bell, PA (US); Heiko Friedrich Stahl, Biberach (DE); Sathyadevi Venkataramani, Blue Bell, PA (US); Vladimir H. Voynov, Danbury, CT (US); Haiguang Xiao, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 334 days.

(21) Appl. No.: 17/002,907

(22) Filed: Aug. 26, 2020

(65) Prior Publication Data
US 2020/0399378 A1 Dec. 24, 2020

Related U.S. Application Data

(62) Division of application No. 16/002,058, filed on Jun. 7, 2018, now Pat. No. 10,793,634.

(30) Foreign Application Priority Data

Jun. 9, 2017 (EP) .................................. 17175122

(51) Int. Cl.
C07K 16/28 (2006.01)
A61K 39/00 (2006.01)
A61P 27/02 (2006.01)
A61P 25/28 (2006.01)

(52) U.S. Cl.
CPC .......... *C07K 16/2863* (2013.01); *A61P 25/28* (2018.01); *A61K 2039/505* (2013.01); *A61K 2039/54* (2013.01); *A61K 2039/545* (2013.01); *A61P 27/02* (2018.01); *C07K 2317/24* (2013.01); *C07K 2317/34* (2013.01); *C07K 2317/56* (2013.01); *C07K 2317/565* (2013.01); *C07K 2317/75* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,275,149 A | 6/1981 | Litman et al. |
| 4,301,144 A | 11/1981 | Iwashita et al. |
| 4,318,980 A | 3/1982 | Uslaski et al. |
| 4,419,446 A | 12/1983 | Howley et al. |
| 4,496,689 A | 1/1985 | Mitra |
| 4,560,655 A | 12/1985 | Baker |
| 4,601,978 A | 7/1986 | Karin |
| 4,640,835 A | 2/1987 | Shimizu et al. |
| 4,657,866 A | 4/1987 | Kumar |
| 4,670,417 A | 6/1987 | Iwasaki et al. |
| 4,737,456 A | 4/1988 | Weng et al. |
| 4,767,704 A | 8/1988 | Cleveland et al. |
| 4,791,192 A | 12/1988 | Nakagawa et al. |
| 4,816,567 A | 3/1989 | Cabilly et al. |
| 4,927,762 A | 5/1990 | Darfler |
| 4,965,199 A | 10/1990 | Capon et al. |
| 5,122,469 A | 6/1992 | Mather et al. |
| 5,888,809 A | 3/1999 | Allison |
| 6,037,454 A | 3/2000 | Jardieu et al. |
| 6,054,297 A | 4/2000 | Carter et al. |
| 6,407,213 B1 | 6/2002 | Carter et al. |
| 2010/0150914 A1 | 6/2010 | Wang |
| 2010/0196390 A1 | 8/2010 | Lin et al. |
| 2014/0004119 A1 | 1/2014 | Saragovi et al. |

FOREIGN PATENT DOCUMENTS

| | | |
|---|---|---|
| CN | 101909647 A | 12/2010 |
| CN | 101939337 A | 1/2011 |
| CN | 101980603 A | 2/2011 |
| CN | 102159215 A | 8/2011 |
| CN | 105566272 A | 5/2016 |
| EP | 73657 A1 | 3/1983 |
| EP | 183070 A2 | 6/1986 |
| EP | 244234 A2 | 11/1987 |

(Continued)

OTHER PUBLICATIONS

Van Bulck et al., Int. J. Mol. Sci. 2019, 20, 719; doi: 10.3390/ijms20030719; 36 pages total (Year: 2019).*
The webpage from https://www.mayoclinic.org/diseases-conditions/huntingtons-disease/symptoms-causes/syc-20356117?p=1 (4 pages total; downloaded Oct. 14, 2018 (Year: 2018).*
Fusar-Poli et al., World Psychiatry 2017;16:251-265 (Year: 2017).*
Stepnicki et al., Molecules 2018, 23, 2087; doi:10.3390/molecules23082087 (Year: 2018).*
Mikanmaa et al., NeuroImage 190 (2019) 144-153 (Year: 2019).*
Traub et al, J Pharmacol Exp Ther 361:355-365 (Year: 2017).*

(Continued)

*Primary Examiner* — Christina M Borgeest
(74) *Attorney, Agent, or Firm* — Mary Breen Smith

(57) ABSTRACT

The present invention relates to novel agonistic anti-TrkB antibodies and therapeutic and diagnostic methods and compositions for using the same.

1 Claim, 14 Drawing Sheets

Specification includes a Sequence Listing.

(56) References Cited

FOREIGN PATENT DOCUMENTS

| | | |
|---|---|---|
| EP | 402226 A1 | 12/1990 |
| WO | 1987000195 A1 | 1/1987 |
| WO | 1990013646 A1 | 11/1990 |
| WO | 1994011026 A2 | 5/1994 |
| WO | 1996032478 A1 | 10/1996 |
| WO | 2006133164 | 12/2006 |
| WO | 2008078179 | 7/2008 |
| WO | 2009048605 A1 | 4/2009 |
| WO | 2009053442 A1 | 4/2009 |
| WO | 2009092049 | 7/2009 |
| WO | 2009098238 A1 | 8/2009 |
| WO | 2010014613 A2 | 2/2010 |
| WO | 2010086828 | 8/2010 |
| WO | 2011103667 | 9/2011 |
| WO | 2011156479 A2 | 12/2011 |
| WO | 2012027821 A1 | 3/2012 |
| WO | 2012156505 | 11/2012 |
| WO | 2015173756 A2 | 11/2015 |
| WO | 2017019907 | 2/2017 |
| WO | 2017085035 | 5/2017 |
| WO | 2019108662 A1 | 6/2019 |

OTHER PUBLICATIONS

Drummond and Wisniewski, Acta Neuropathol. 2017, 133:155-175 (Year: 2017).*

Miranda-Lourenço et al., Pharmacological Research 162 (2020) 105281 (Year: 2020).*

Bai, Yujing et al. "An Agonistic TrkB mAb Causes Sustained TrkB Activation, Delays RGC Death, and Protects the Retinal Structure in Optic Nerve Axotomy and in Glaucoma" (2010) IOVS, vol. 51, No. 9, 4722-4731.

Cazorla, M. et al "Pharmacological characterization of six trkB antibodies reveals a novel class of functional agents for the study of BDNF receptor" (2011) British Journal of Pharmacology, vol. 162, 947-960.

Piche-Nicholas, Nicole et al. "Changes in complementarity-determining regions significantly alter IgG binding to the neonatal Fc receptor (FcRn) and pharmacokinetics" (2018) MABS, vol. 10, No. 1, 81-94.

Todd, Daniel et al. "A Monoclonal Antibody TrkB Receptor Agonist as a Potential Therapeutic for Huntington's Disease" (2014) PLOS One, vol. 9, Issue 2, e87923, 13 pgs.

Almagro, Juan C. et al. "Antibody modeling assessment" (2011) Proteins, 79, 3050-3066.

Altschul, Stephen F. et al. "Basic Local Alignment Search Tool" (1990) Journal of Molecular Biology, 215, 403-410.

Altschul, Stephen F. et al. "Gapped BLAST and PSI-BLAST: a new generation of protein database search programs" (1997) Nucleic Acids Research, vol. 25, No. 17, 3389-3402.

Bakri, Sophie J. et al. "Pharmacokinetics of Intravitreal Ranibizumab (Lucentis)" (2007) American Academy of Ophthalmology, 2179-2182.

Barnes, David et al. "Methods for Growth of Cultured Cells in a Serum-Free Medium" (1980) Analytical Biochemistry, 102, 255-270.

Brennan, Maureen et al. "Preparation of Bispecific Antibodies by Chemical Recombination of Monoclonal Immunoglobulin G1 Fragments" (1985) Science, vol. 229, 81-83.

Carter, Paul et al. "High Level *Escherichia coli* Expression and Production of a Bivalent Humanized Antibody Fragment" (1992) Biotechnology, vol. 10, 163-167.

Chothia, Cyrus et al. "Canonical Structures for the Hypervariable Regions of Immunoglobulins" (1987) Journal of Molecular Biology, vol. 196, 901-917.

Chothia, Cyrus et al. "Domain Association in Immunoglobulin Molecules the Packing of Variable Domains" (1985) Journal of Molecular Biology, 186, 651-663.

Clackson, Tim et al. "Making antibody fragments using phage display libraries" (1991) Nature, vol. 352, 624-628.

Edge, Albert S. B. et al. "Deglycosylation of Glycoproteins by Trifluromethanesulfonic Acid" (1981) Analytical Biochemistry, 118, 131-137.

Fleer, R. et al. "Stable Multicopy Vectors for High-Level Secretion of Recombinant Human Serum Albumin by *Kluyveromyces* Yeasts" (1991) Nature Biotechnology, vol. 9, 968-975.

Graham, F.L. et al. "Characteristics of a Human Cell Line Transformed by DNA from Human Adenovirus Type 5" (1977) J. Gen. Virol., vol. 36, 59-72.

Guss, Bengt et al. "Structure of the IgG-binding regions of streptococcal protein G" (1986) The EMBO Journal, vol. 5, No. 7, 1567-1575.

Ham, Richard G. et al. "Media and Growth Requirements" (1979) Methods in Enzymology, vol. 58, 44-93.

Higgins, Desmond G. et al. "Using CLUSTAL for Multiple Sequence Alignments" (1996) Methods in Enzymology, vol. 266, 383-402.

Hutton-Smith, Laurence A. et al. "A Mechanistic Model of the Intravitreal Pharmacokinetics of Large Molecules and the Pharmacodynamic Suppression of Ocular Vascular Endothelial Growth Factor Levels by Ranibizumab in Patients with Neovascular Age-Related Macular Degeneration" (2016) Molecular Pharmaceutics, 2941-2950.

Jones, Elizabeth W. "Proteinase Mutants of *Saccharomyces cerevisiae*" (1977) Genetics, 85, 23-33.

Karlin, Samuel et al. "Applications and statistics for multiple high-scoring segments in molecular sequences" (1993) Proc. Natl. Acad. Sci., vol. 90, 5873-5877.

Karlin, Samuel et al. "Methods for assessing the statistical significance of molecular sequence features by using general scoring schemes" (1990) Proc. Natl. Acad. Sci., vol. 87, 2264-2268.

Kohler, G. et al. "Continuous cultures of fused cells secreting antibody of predefined specificity" (1975) Nature, vol. 256, 495-497.

Lindmark, Roger et al. "Binding of Immunoglobulins to Protein A and Immunoglobulin Levels in Mammalian Sera" (1983) Journal of Immunological Methods, 62, 1-13.

Maier, Johannes K. et al. "Assessment of fully automated antibody homology modeling protocols in molecular operating environment" (2014) Proteins, 82, 1599-1610.

Marks, James D. et al. "By-passing Immunization Human Antibodies from V-gene Libraries Displayed on Phage" (1991) Journal of Molecular Biology, 222, 581-597.

Mather, Jennie P. "Estsablishment an Characterization of Two Distinct Mouse Testicular Epithelial Cell Lines" (1980) Biology of Reproduction, 23, 243-252.

Mather, Jennie P. et al. "Culture of Testicular Cells in Horomone-Supplemented Serum-Free Medium" (1982) Annals New York Academy of Sciences, 44-68.

Morimoto, Koichi et al. "Single-step purification of F(ab')2 fragments of mouse monoclonal antibodies (immunoglobulins G1) by hydrophobic interaction high performance liquid chromatography using TSKgel Phenyl-5PW" (1992) Journal of Biochemical and Biophysical Methods, 24, 107-117.

Morrison, Sherie L. et al. "Chimeric human antibody molecules: Mouse antigen-binding domains with human constant region domains" (1984) Proc. Natl. Acad. Sci., vol. 81, 6851-6855.

O'sullivan, M.J. et al. "Methods for the Preparation of Enzyme-Antibody Conjugates for Use in Enzyme Immunoassay" (1981) Methods in Enzymology, vol. 73, 147-166.

Pearson, William R. et al. "Improved tools for biological sequence comparison" (1988) Proc. Natl. Acad. Sci., vol. 85, 2444-2448.

Reyes, Gregory R. et al. "Expression of human B-interferon cDNA under the control of a thymidine kinase promoter from herpes simplex virus" (1982) Nature, vol. 297, 598-601.

Sojar, Hakimuddin et al. "A Chemical Method for the Deglycosylation of Proteins" (1987) Archives of Biochemistry and Biophysics vol. 259, No. 1, 52-57.

Stinchcomb, D.T. et al. "Isolation and characterisation of a yeast chromosomal replicator" (1979), Nature, vol. 282, 39-43.

Thotakura, Nageswara R. et al. "Enzymatic Deglycosylation of Glycoproteins" (1987) Methods in Enzymology, vol. 138, 350-359.

(56) References Cited

OTHER PUBLICATIONS

Torelli, Alberto et al. "ADVANCE and ADAM: two algorithms for the analysis of global similarity between homologous informatoinal sequences" (1994) Cabios, vol. 10, No. 1, 3-5.
Urlaub, Gail et al. "Isolation of Chinese hamster cell mutants deficient in dihydrofolate reductase activity" (1980) Proc. Natl. Acad. Sci., vol. 77, No. 7, 4216-4220.
Van Den Berg, Johan A. et al. "Kluyveromyces as a Host for Heterologous Gene Expression: Expression and Secretion of Prochymosin" (1990) Nature Biotechnology, vol. 8, 135-139.
Yaniv, Moshe "Enhancing elements for activation of eukaryotic promoters" (1982) Nature, vol. 297, 17-18.
Zapata, Gerardo et al. "Engineering linear F(ab')2 fragments for efficient production in *Escherichia coli* and enhanced antiproliferative activity" (1995) Protein Engineering, vol. 8, No. 10, 1057-1062.

* cited by examiner

FIG. 1

SEQUENCE LISTING

<160> NUMBER OF SEQ ID NOS: 61

<210> SEQ ID NO 1
<211> LENGTH: 113
<212> TYPE: PRT
<213> ORGANISM: Mus <mouse, genus>
<220> FEATURE:
<223> OTHER INFORMATION: D003_VL (murine lead), variable light chain

<400> SEQUENCE: 1

```
Asp Ile Val Met Ser Gln Ser Pro Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys
```

<210> SEQ ID NO 2
<211> LENGTH: 113
<212> TYPE: PRT
<213> ORGANISM: Artificial Sequence
<220> FEATURE:
<223> OTHER INFORMATION: 277-gr_VL, (humanized) variable light chain

<400> SEQUENCE: 2

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gln Gly Thr Lys Leu Glu Ile
            100                 105                 110

Lys
```

<210> SEQ ID NO 3
<211> LENGTH: 113
<212> TYPE: PRT
<213> ORGANISM: Artificial Sequence
<220> FEATURE:
<223> OTHER INFORMATION: 277-33_VL: (humanized) variable light chain

<400> SEQUENCE: 3

Asp Ile Val Met Thr Gln Ser Pro Asp Ser Leu Ala Val Ser Leu Gly

```
                1               5                   10                  15
        Glu Arg Ala Thr Ile Ser Cys Lys Ser Ser Gln Ser Leu Leu Tyr Ser
                        20                  25                  30

Ser Asn Gln Lys Asn Tyr Leu Ala Trp Tyr Gln Gln Lys Pro Gly Gln
                        35                  40                  45

Pro Pro Lys Leu Leu Ile Tyr Trp Ala Ser Thr Arg Glu Ser Gly Val
                        50                  55                  60

Pro Asp Arg Phe Ser Gly Ser Gly Ser Gly Thr Asp Phe Thr Leu Thr
         65                 70                  75                  80

Ile Ser Ser Leu Gln Ala Glu Asp Val Ala Val Tyr Tyr Cys Gln Gln
                        85                  90                  95

Tyr Tyr Ser Tyr Pro Tyr Thr Phe Gly Gly Gly Thr Lys Leu Glu Ile
                        100                 105                 110

Lys

<210> SEQ ID NO 4
<211> LENGTH: 113
<212> TYPE: PRT
<213> ORGANISM: Artificial Sequence
<220> FEATURE:
<223> OTHER INFORMATION: 277-35_VL, (humanized) variable light chain

<400> SEQUENCE: 4

Asp Ile Val Met Thr Gln Ser Pro Asp Ser Leu Ala Val Ser Leu Gly
         1              5                   10                  15

Glu Arg Ala Thr Ile Ser Cys Lys Ser Ser Gln Ser Leu Leu Tyr Ser
                        20                  25                  30

Ser Asn Gln Lys Asn Tyr Leu Ala Trp Tyr Gln Gln Lys Pro Gly Gln
                        35                  40                  45

Pro Pro Lys Leu Leu Ile Tyr Trp Ala Ser Thr Arg Glu Ser Gly Val
                        50                  55                  60

Pro Asp Arg Phe Ser Gly Ser Gly Ser Gly Thr Asp Phe Thr Leu Thr
         65                 70                  75                  80

Ile Ser Ser Leu Gln Ala Glu Asp Val Ala Val Tyr Tyr Cys Gln Gln
                        85                  90                  95

Tyr Tyr Ser Tyr Pro Tyr Thr Phe Gly Gly Gly Thr Lys Leu Glu Ile
                        100                 105                 110

Lys

<210> SEQ ID NO 5
<211> LENGTH: 113
<212> TYPE: PRT
<213> ORGANISM: Artificial Sequence
<220> FEATURE:
<223> OTHER INFORMATION: 277-42_VL, (humanized) variable light chain

<400> SEQUENCE: 5

Asp Ile Val Met Thr Gln Ser Pro Asp Ser Leu Ala Val Ser Leu Gly
         1              5                   10                  15

Glu Arg Ala Thr Ile Asn Cys Lys Ser Ser Gln Ser Leu Leu Tyr Ser
                        20                  25                  30

Ser Asn Gln Lys Asn Tyr Leu Ala Trp Tyr Gln Gln Lys Pro Gly Gln
                        35                  40                  45

Pro Pro Lys Leu Leu Ile Tyr Trp Ala Ser Thr Arg Glu Ser Gly Val
                        50                  55                  60

Pro Asp Arg Phe Ser Gly Ser Gly Ser Gly Thr Asp Phe Thr Leu Thr
         65                 70                  75                  80
```

```
Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gly Thr Lys Leu Glu Ile
            100                 105                 110

Lys

<210> SEQ ID NO 6
<211> LENGTH: 113
<212> TYPE: PRT
<213> ORGANISM: Artificial Sequence
<220> FEATURE:
<223> OTHER INFORMATION: 277-44_VL, (humanized) variable light chain

<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gln Gly Thr Lys Leu Glu Ile
            100                 105                 110

Lys

<210> SEQ ID NO 7
<211> LENGTH: 113
<212> TYPE: PRT
<213> ORGANISM: Artificial Sequence
<220> FEATURE:
<223> OTHER INFORMATION: 277-48_VL, (humanized) variable light chain

<400> SEQUENCE: 7

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gln Gly Thr Lys Leu Glu Ile
            100                 105                 110

Lys

<210> SEQ ID NO 8
<211> LENGTH: 113
<212> TYPE: PRT
```

```
<213> ORGANISM: Artificial Sequence
<220> FEATURE:
<223> OTHER INFORMATION: 277-51_VL, (humanized) variable light chain

<400> SEQUENCE: 8

Asp Ile Val Met Thr Gln Ser Pro Asp Ser Leu Ala Val Ser Leu Gly
1               5                   10                  15

Glu Arg Ala Thr Ile Ser Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys

<210> SEQ ID NO 9
<211> LENGTH: 113
<212> TYPE: PRT
<213> ORGANISM: Artificial Sequence
<220> FEATURE:
<223> OTHER INFORMATION: 277-64_VL, (humanized) variable light chain

<400> SEQUENCE: 9

Asp Ile Val Met Thr Gln Ser Pro Asp Ser Leu Ala Val Ser Leu Gly
1               5                   10                  15

Glu Arg Ala Thr Ile Ser Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gln Gly Thr Lys Leu Glu Ile
            100                 105                 110

Lys

<210> SEQ ID NO 10
<211> LENGTH: 113
<212> TYPE: PRT
<213> ORGANISM: Artificial Sequence
<220> FEATURE:
<223> OTHER INFORMATION: 277-67_VL, (humanized) variable light chain

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Tyr Ser
            20                  25                  30

Ser Asn Gln Lys Asn Tyr Leu Ala Trp Tyr Gln Gln Lys Pro Gly Gln
```

```
                35                  40                  45
Ser Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Tyr Pro Tyr Thr Phe Gly Gln Gly Thr Lys Leu Glu Ile
                100                 105                 110

Lys

<210> SEQ ID NO 11
<211> LENGTH: 115
<212> TYPE: PRT
<213> ORGANISM: Mus <mouse, genus>
<220> FEATURE:
<223> OTHER INFORMATION: D003_VH, (murine lead) variable heavy chain

<400> SEQUENCE: 11

Gln Val Gln Leu Gln Gln Ser Gly Ala Glu Leu Ala Lys Pro Gly Ala
 1               5                  10                  15

Ser Val Lys Met Ser Cys Lys Ala Ser Gly Tyr Thr Phe Thr Gly Tyr
                 20                  25                  30

Trp Met His Trp Val Lys Gln Arg Pro Gly Gln Gly Leu Glu Trp Ile
             35                  40                  45

Gly Tyr Ile Asn Pro Ser Thr Asp Tyr Thr Glu Tyr Asn Gln Lys Phe
 50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Arg Thr Gly Asn Tyr Trp Gly Gln Gly Thr Thr Leu Thr
                100                 105                 110

Val Ser Ser
        115

<210> SEQ ID NO 12
<211> LENGTH: 115
<212> TYPE: PRT
<213> ORGANISM: Artificial Sequence
<220> FEATURE:
<223> OTHER INFORMATION: 277-gr_VH, (humanized) variable heavy chain

<400> SEQUENCE: 12

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                 20                  25                  30

Trp Met His Trp Val Arg Gln Ala Pro Gly Gln Gly Leu Glu Trp Met
             35                  40                  45

Gly Tyr Ile Asn Pro Ser Thr Asp Tyr Thr Glu Tyr Asn Gln Lys Phe
 50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Arg Thr Gly Asn Tyr Trp Gly Gln Gly Thr Leu Val Thr
```

Val Ser Ser
    115

<210> SEQ ID NO 13
<211> LENGTH: 115
<212> TYPE: PRT
<213> ORGANISM: Artificial Sequence
<220> FEATURE:
<223> OTHER INFORMATION: 277-33_VH, (humanized) variable heavy chain

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Val Thr Leu Thr Arg Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Ser Arg Thr Gly Asn Tyr Trp Gly Gln Gly Thr Thr Val Thr
            100                 105                 110

Val Ser Ser
    115

<210> SEQ ID NO 14
<211> LENGTH: 115
<212> TYPE: PRT
<213> ORGANISM: Artificial Sequence
<220> FEATURE:
<223> OTHER INFORMATION: 277-35_VH, (humanized) variable heavy chain

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Thr Gly Asn Tyr Trp Gly Gln Gly Thr Thr Val Thr
            100                 105                 110

Val Ser Ser
    115

<210> SEQ ID NO 15
<211> LENGTH: 115
<212> TYPE: PRT
<213> ORGANISM: Artificial Sequence
<220> FEATURE:

<223> OTHER INFORMATION: 277-42_VH, (humanized) variable heavy chain

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Thr Gly Asn Tyr Trp Gly Gln Gly Thr Thr Val Thr
            100                 105                 110

Val Ser Ser
        115

<210> SEQ ID NO 16
<211> LENGTH: 115
<212> TYPE: PRT
<213> ORGANISM: Artificial Sequence
<220> FEATURE:
<223> OTHER INFORMATION: 277-44_VH, (humanized) variable heavy chain

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Ala Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Ser Arg Thr Gly Asn Tyr Trp Gly Gln Gly Thr Thr Val Thr
            100                 105                 110

Val Ser Ser
        115

<210> SEQ ID NO 17
<211> LENGTH: 115
<212> TYPE: PRT
<213> ORGANISM: Artificial Sequence
<220> FEATURE:
<223> OTHER INFORMATION: 277-48_VH, (humanized) variable heavy chain

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Arg Pro Gly Gln Gly Leu Glu Trp Ile

```
                35                  40                  45
Gly Tyr Ile Asn Pro Ser Thr Asp Tyr Thr Glu Tyr Asn Gln Lys Phe
 50                  55                  60

Lys Asp Arg Val Thr Met Thr Arg Asp Thr Ser Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Arg Thr Gly Asn Tyr Trp Gly Gln Gly Thr Thr Val Thr
            100                 105                 110

Val Ser Ser
        115

<210> SEQ ID NO 18
<211> LENGTH: 115
<212> TYPE: PRT
<213> ORGANISM: Artificial Sequence
<220> FEATURE:
<223> OTHER INFORMATION: 277-51_VH, (humanized) variable heavy chain

<400> SEQUENCE: 18

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
             20                  25                  30

Trp Met His Trp Val Arg Gln Arg Pro Gly Gln Gly Leu Glu Trp Ile
         35                  40                  45

Gly Tyr Ile Asn Pro Ser Thr Asp Tyr Thr Glu Tyr Asn Gln Lys Phe
 50                  55                  60

Lys Asp Arg Ala Thr Leu Thr Arg Asp Thr Ser Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Arg Thr Gly Asn Tyr Trp Gly Gln Gly Thr Thr Val Thr
            100                 105                 110

Val Ser Ser
        115

<210> SEQ ID NO 19
<211> LENGTH: 115
<212> TYPE: PRT
<213> ORGANISM: Artificial Sequence
<220> FEATURE:
<223> OTHER INFORMATION: 277-64_VH, (humanized) variable heavy chain

<400> SEQUENCE: 19

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
             20                  25                  30

Trp Met His Trp Val Arg Gln Ala Pro Gly Gln Gly Leu Glu Trp Ile
         35                  40                  45

Gly Tyr Ile Asn Pro Ser Thr Asp Tyr Thr Glu Tyr Asn Gln Lys Phe
 50                  55                  60

Lys Asp Arg Val Thr Met Thr Arg Asp Thr Ser Ser Thr Val Tyr
 65                  70                  75                  80

Met Glu Leu Ser Ser Leu Arg Ser Glu Asp Thr Ala Val Tyr Tyr Cys
                 85                  90                  95
```

```
Ala Arg Ser Arg Thr Gly Asn Tyr Trp Gly Gln Gly Thr Thr Val Thr
            100                 105                 110

Val Ser Ser
        115

<210> SEQ ID NO 20
<211> LENGTH: 115
<212> TYPE: PRT
<213> ORGANISM: Artificial Sequence
<220> FEATURE:
<223> OTHER INFORMATION: 277-67_VH, (humanized) variable heavy chain

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Ala Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Thr Gly Asn Tyr Trp Gly Gln Gly Thr Thr Val Thr
            100                 105                 110

Val Ser Ser
        115

<210> SEQ ID NO 21
<211> LENGTH: 220
<212> TYPE: PRT
<213> ORGANISM: Artificial Sequence
<220> FEATURE:
<223> OTHER INFORMATION: 277-gr (Light Chain, IgG1)

<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

```
Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 22
<211> LENGTH: 444
<212> TYPE: PRT
<213> ORGANISM: Artificial Sequence
<220> FEATURE:
<223> OTHER INFORMATION: 277-gr (Heavy Chain, IgG1)

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Ala Pro Gly Gln Gly Leu Glu Trp Met
        35                  40                  45

Gly Tyr Ile Asn Pro Ser Thr Asp Tyr Thr Glu Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Thr Gly Asn Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300
```

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 23
<211> LENGTH: 444
<212> TYPE: PRT
<213> ORGANISM: Artificial Sequence
<220> FEATURE:
<223> OTHER INFORMATION: 277-gr (Heavy Chain, IgG1-KO)

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Ala Pro Gly Gln Gly Leu Glu Trp Met
        35                  40                  45

Gly Tyr Ile Asn Pro Ser Thr Asp Tyr Thr Glu Tyr Asn Gln Lys Phe
    50                  55                  60

Lys Asp Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
            85                  90                  95

Ala Arg Ser Arg Thr Gly Asn Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
                435                 440

<210> SEQ ID NO 24
<211> LENGTH: 220
<212> TYPE: PRT
<213> ORGANISM: Artificial Sequence
<220> FEATURE:
<223> OTHER INFORMATION: 277-33 (Light Chain, IgG1)

<400> SEQUENCE: 24

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 25
<211> LENGTH: 444
<212> TYPE: PRT
<213> ORGANISM: Artificial Sequence
<220> FEATURE:
<223> OTHER INFORMATION: 277-33 (Heavy Chain, IgG1)

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Val Thr Leu Thr Arg Asp Thr Ser Thr Ser Thr Val Tyr
65                  70                  75                  80

Met Glu Leu Ser Ser Leu Thr Ser Glu Asp Thr Ala Val Tyr Tyr Cys
            85                  90                  95

Ala Arg Ser Arg Thr Gly Asn Tyr Trp Gly Gln Gly Thr Thr Val Thr
        100                 105                 110

Val Ser Ser Ala Ser Thr Lys Gly Pro Ser Val Phe Pro Leu Ala Pro
    115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
    195                 200                 205

Val Asp Lys Arg Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

-continued

```
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly
        435                 440
```

<210> SEQ ID NO 26
<211> LENGTH: 444
<212> TYPE: PRT
<213> ORGANISM: Artificial Sequence
<220> FEATURE:
<223> OTHER INFORMATION: 277-33 (Heavy Chain, IgG1-KO)

<400> SEQUENCE: 26

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Trp Met His Trp Val Arg Gln Arg Pro Gly Gln Gly Leu Glu Trp Ile
        35                  40                  45
Gly Tyr Ile Asn Pro Ser Thr Asp Tyr Thr Glu Tyr Asn Gln Lys Phe
    50                  55                  60
Lys Asp Arg Val Thr Leu Thr Arg Asp Thr Ser Thr Ser Thr Val Tyr
65                  70                  75                  80
Met Glu Leu Ser Ser Leu Thr Ser Glu Asp Thr Ala Val Tyr Tyr Cys
                85                  90                  95
Ala Arg Ser Arg Thr Gly Asn Tyr Trp Gly Gln Gly Thr Thr Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
```

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 27
<211> LENGTH: 220
<212> TYPE: PRT
<213> ORGANISM: Artificial Sequence
<220> FEATURE:
<223> OTHER INFORMATION: 277-35 (Light Chain, IgG1)

<400> SEQUENCE: 27

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 28
<211> LENGTH: 444
<212> TYPE: PRT
<213> ORGANISM: Artificial Sequence
<220> FEATURE:
<223> OTHER INFORMATION: 277-35 (Heavy Chain, IgG1)

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Thr Gly Asn Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
    435                 440

<210> SEQ ID NO 29
<211> LENGTH: 444
<212> TYPE: PRT
<213> ORGANISM: Artificial Sequence
<220> FEATURE:
<223> OTHER INFORMATION: 277-35 (Heavy Chain, IgG1-KO)

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Thr Gly Asn Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

```
Thr Gln Thr Tyr Ile Cys Asn Val Asn His Lys Pro Ser Asn Thr Lys
        195                 200                 205
Val Asp Lys Arg Val Glu Pro Lys Ser Cys Asp Lys Thr His Thr Cys
    210                 215                 220
Pro Pro Cys Pro Ala Pro Glu Ala Ala Gly Gly Pro Ser Val Phe Leu
225                 230                 235                 240
Phe Pro Pro Lys Pro Lys Asp Thr Leu Met Ile Ser Arg Thr Pro Glu
            245                 250                 255
Val Thr Cys Val Val Val Asp Val Ser His Glu Asp Pro Glu Val Lys
        260                 265                 270
Phe Asn Trp Tyr Val Asp Gly Val Glu Val His Asn Ala Lys Thr Lys
    275                 280                 285
Pro Arg Glu Glu Gln Tyr Asn Ser Thr Tyr Arg Val Val Ser Val Leu
290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
            325                 330                 335
Ala Lys Gly Gln Pro Arg Glu Pro Gln Val Tyr Thr Leu Pro Pro Ser
        340                 345                 350
Arg Glu Glu Met Thr Lys Asn Gln Val Ser Leu Thr Cys Leu Val Lys
    355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
            405                 410                 415
Gln Gly Asn Val Phe Ser Cys Ser Val Met His Glu Ala Leu His Asn
        420                 425                 430
His Tyr Thr Gln Lys Ser Leu Ser Leu Ser Pro Gly
    435                 440

<210> SEQ ID NO 30
<211> LENGTH: 220
<212> TYPE: PRT
<213> ORGANISM: Artificial Sequence
<220> FEATURE:
<223> OTHER INFORMATION: 277-42 (Light Chain, IgG1)

<400> SEQUENCE: 30

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Leu Tyr Ser
            20                  25                  30
Ser Asn Gln Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
            85                  90                  95
Tyr Tyr Ser Tyr Pro Tyr Thr Phe Gly Gly Gly Thr Lys Leu Glu Ile
        100                 105                 110
```

```
Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 31
<211> LENGTH: 444
<212> TYPE: PRT
<213> ORGANISM: Artificial Sequence
<220> FEATURE:
<223> OTHER INFORMATION: Synthetic Polypeptide

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Thr Gly Asn Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255
```

```
Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 32
<211> LENGTH: 444
<212> TYPE: PRT
<213> ORGANISM: Artificial Sequence
<220> FEATURE:
<223> OTHER INFORMATION: 277-42 (Heavy Chain, IgG1-KO)

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Arg Pro Gly Gln Gly Leu Glu Trp Ile
            35                  40                  45

Gly Tyr Ile Asn Pro Ser Thr Asp Tyr Thr Glu Tyr Asn Gln Lys Phe
    50                  55                  60

Lys Asp Arg Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Ser Arg Thr Gly Asn Tyr Trp Gly Gln Gly Thr Thr Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175
```

```
Leu Tyr Ser Leu Ser Ser Val Thr Val Pro Ser Ser Leu Gly
            180                 185                 190

Thr Gln Thr Tyr Ile Cys Asn Val Asn His Lys Pro Ser Asn Thr Lys
                195                 200                 205

Val Asp Lys Arg Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
                290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
                435                 440

<210> SEQ ID NO 33
<211> LENGTH: 220
<212> TYPE: PRT
<213> ORGANISM: Artificial Sequence
<220> FEATURE:
<223> OTHER INFORMATION: 277-44 (Light Chain, IgG1)

<400> SEQUENCE: 33

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

```
Tyr Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 34
<211> LENGTH: 444
<212> TYPE: PRT
<213> ORGANISM: Artificial Sequence
<220> FEATURE:
<223> OTHER INFORMATION: 277-44 (Heavy Chain, IgG1)

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Ala Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Ser Arg Thr Gly Asn Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 35
<211> LENGTH: 444
<212> TYPE: PRT
<213> ORGANISM: Artificial Sequence
<220> FEATURE:
<223> OTHER INFORMATION: 277-44 (Heavy Chain, IgG1-KO)

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Ala Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Val Thr Met Thr Arg Asp Thr Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Ser Arg Thr Gly Asn Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160
```

```
Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 36
<211> LENGTH: 220
<212> TYPE: PRT
<213> ORGANISM: Artificial Sequence
<220> FEATURE:
<223> OTHER INFORMATION: 277-48 (Light Chain, IgG1)

<400> SEQUENCE: 36

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220
```

<210> SEQ ID NO 37
<211> LENGTH: 444
<212> TYPE: PRT
<213> ORGANISM: Artificial Sequence
<220> FEATURE:
<223> OTHER INFORMATION: 277-48 (Heavy Chain, IgG1)

<400> SEQUENCE: 37

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Thr Gly Asn Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220
```

```
Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly
    435                 440

<210> SEQ ID NO 38
<211> LENGTH: 444
<212> TYPE: PRT
<213> ORGANISM: Artificial Sequence
<220> FEATURE:
<223> OTHER INFORMATION: 277-48 (Heavy Chain, IgG1-KO)

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Ser Arg Thr Gly Asn Tyr Trp Gly Gln Gly Thr Thr Val Thr
        100                 105                 110

Val Ser Ser Ala Ser Thr Lys Gly Pro Ser Val Phe Pro Leu Ala Pro
    115                 120                 125

Ser Ser Lys Ser Thr Ser Gly Gly Thr Ala Ala Leu Gly Cys Leu Val
130                 135                 140
```

```
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
    195                 200                 205

Val Asp Lys Arg Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly
    435                 440

<210> SEQ ID NO 39
<211> LENGTH: 220
<212> TYPE: PRT
<213> ORGANISM: Artificial Sequence
<220> FEATURE:
<223> OTHER INFORMATION: 277-51 (Light Chain, IgG1)

<400> SEQUENCE: 39

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60
```

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

<210> SEQ ID NO 40
<211> LENGTH: 444
<212> TYPE: PRT
<213> ORGANISM: Artificial Sequence
<220> FEATURE:
<223> OTHER INFORMATION: 277-51 (Heavy Chain, IgG1)

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
50                  55                  60

Lys Asp Arg Ala Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Thr Gly Asn Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

```
Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 41
<211> LENGTH: 444
<212> TYPE: PRT
<213> ORGANISM: Artificial Sequence
<220> FEATURE:
<223> OTHER INFORMATION: 277-51 (Heavy Chain, IgG1-KO)

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Ala Thr Leu Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Arg Thr Gly Asn Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125
```

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Arg Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
                435                 440

```
<210> SEQ ID NO 42
<211> LENGTH: 220
<212> TYPE: PRT
<213> ORGANISM: Artificial Sequence
<220> FEATURE:
<223> OTHER INFORMATION: 277-64 (Light Chain, IgG1)

<400> SEQUENCE: 42
```

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

```
Pro Pro Lys Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 43
<211> LENGTH: 444
<212> TYPE: PRT
<213> ORGANISM: Artificial Sequence
<220> FEATURE:
<223> OTHER INFORMATION: 277-64 (Heavy Chain, IgG1)

<400> SEQUENCE: 43

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Trp Met His Trp Val Arg Gln Ala Pro Gly Gln Gly Leu Glu Trp Ile
         35                  40                  45

Gly Tyr Ile Asn Pro Ser Thr Asp Tyr Thr Glu Tyr Asn Gln Lys Phe
     50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Arg Thr Gly Asn Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190
```

```
Thr Gln Thr Tyr Ile Cys Asn Val Asn His Lys Pro Ser Asn Thr Lys
        195                 200                 205
Val Asp Lys Arg Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly
        435                 440

<210> SEQ ID NO 44
<211> LENGTH: 444
<212> TYPE: PRT
<213> ORGANISM: Artificial Sequence
<220> FEATURE:
<223> OTHER INFORMATION: 277-64 (Heavy Chain, IgG1-KO)

<400> SEQUENCE: 44

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Trp Met His Trp Val Arg Gln Ala Pro Gly Gln Gly Leu Glu Trp Ile
        35                  40                  45
Gly Tyr Ile Asn Pro Ser Thr Asp Tyr Thr Glu Tyr Asn Gln Lys Phe
    50                  55                  60
Lys Asp Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Ser Arg Thr Gly Asn Tyr Trp Gly Gln Gly Thr Thr Val Thr
            100                 105                 110
```

```
Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 45
<211> LENGTH: 220
<212> TYPE: PRT
<213> ORGANISM: Artificial Sequence
<220> FEATURE:
<223> OTHER INFORMATION: 277-67 (Light Chain, IgG1)

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30
```

```
Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Gln Gly Thr Lys Leu Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
 130                 135                 140

Phe Tyr Pro Arg Glu Ala Lys Val Gln Trp Lys Val Asp Asn Ala Leu
 145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 46
<211> LENGTH: 444
<212> TYPE: PRT
<213> ORGANISM: Artificial Sequence
<220> FEATURE:
<223> OTHER INFORMATION: 277-67 (Heavy Chain, IgG1)

<400> SEQUENCE: 46

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

Trp Met His Trp Val Arg Gln Ala Pro Gly Gln Gly Leu Glu Trp Ile
            35                  40                  45

Gly Tyr Ile Asn Pro Ser Thr Asp Tyr Thr Glu Tyr Asn Gln Lys Phe
 50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Ser Arg Thr Gly Asn Tyr Trp Gly Gln Gly Thr Thr Val Thr
                100                 105                 110

Val Ser Ser Ala Ser Thr Lys Gly Pro Ser Val Phe Pro Leu Ala Pro
                115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
 145                 150                 155                 160

Leu Thr Ser Gly Val His Thr Phe Pro Ala Val Leu Gln Ser Ser Gly
                165                 170                 175
```

```
Leu Tyr Ser Leu Ser Ser Val Thr Val Pro Ser Ser Leu Gly
            180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 47
<211> LENGTH: 444
<212> TYPE: PRT
<213> ORGANISM: Artificial Sequence
<220> FEATURE:
<223> OTHER INFORMATION: 277-67 (Heavy Chain, IgG1-KO)

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Trp Met His Trp Val Arg Gln Ala Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

Ala Arg Ser Arg Thr Gly Asn Tyr Trp Gly Gln Gly Thr Thr Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
            210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 48
<211> LENGTH: 17
<212> TYPE: PRT
<213> ORGANISM: Mus <mouse, genus>
<220> FEATURE:
<223> OTHER INFORMATION: 277 L-CDR1

<400> SEQUENCE: 48

Lys Ser Ser Gln Ser Leu Leu Tyr Ser Ser Asn Gln Lys Asn Tyr Leu
1               5                   10                  15

Ala

<210> SEQ ID NO 49
<211> LENGTH: 7
<212> TYPE: PRT
<213> ORGANISM: Mus <mouse, genus>
<220> FEATURE:
<223> OTHER INFORMATION: 277 L-CDR2

<400> SEQUENCE: 49

Trp Ala Ser Thr Arg Glu Ser
1               5

<210> SEQ ID NO 50
<211> LENGTH: 9
<212> TYPE: PRT
<213> ORGANISM: Mus <mouse, genus>
<220> FEATURE:
<223> OTHER INFORMATION: 277 L-CDR3

<400> SEQUENCE: 50

Gln Gln Tyr Tyr Ser Tyr Pro Tyr Thr
1               5

<210> SEQ ID NO 51
<211> LENGTH: 10
<212> TYPE: PRT
<213> ORGANISM: Mus <mouse, genus>
<220> FEATURE:
<223> OTHER INFORMATION: 277 H-CDR1

<400> SEQUENCE: 51

Gly Tyr Thr Phe Thr Gly Tyr Trp Met His
1               5                   10

<210> SEQ ID NO 52
<211> LENGTH: 17
<212> TYPE: PRT
<213> ORGANISM: Mus <mouse, genus>
<220> FEATURE:
<223> OTHER INFORMATION: 277 H-CDR2

<400> SEQUENCE: 52

Tyr Ile Asn Pro Ser Thr Asp Tyr Thr Glu Tyr Asn Gln Lys Phe Lys
1               5                   10                  15

Asp

<210> SEQ ID NO 53
<211> LENGTH: 6
<212> TYPE: PRT
<213> ORGANISM: Mus <mouse, genus>
<220> FEATURE:
<223> OTHER INFORMATION: 277 H-CDR3

<400> SEQUENCE: 53

Ser Arg Thr Gly Asn Tyr
1               5

<210> SEQ ID NO 54
<211> LENGTH: 399
<212> TYPE: PRT
<213> ORGANISM: Homo sapiens
<220> FEATURE:
<223> OTHER INFORMATION: Extracellular domain of human TrkB

<400> SEQUENCE: 54

Cys Pro Thr Ser Cys Lys Cys Ser Ala Ser Arg Ile Trp Cys Ser Asp
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Phe Ile Ala Asn Gln Lys Arg Leu
        35                  40                  45

Glu Ile Ile Asn Glu Asp Val Glu Ala Tyr Val Gly Leu Arg Asn
    50                  55                  60

Leu Thr Ile Val Asp Ser Gly Leu Lys Phe Val Ala His Lys Ala Phe
65                  70                  75                  80

Leu Lys Asn Ser Asn Leu Gln His Ile Asn Phe Thr Arg Asn Lys Leu
                85                  90                  95

Thr Ser Leu Ser Arg Lys His Phe Arg His Leu Asp Leu Ser Glu Leu
            100                 105                 110

Ile Leu Val Gly Asn Pro Phe Thr Cys Ser Cys Asp Ile Met Trp Ile
            115                 120                 125

Lys Thr Leu Gln Glu Ala Lys Ser Ser Pro Asp Thr Gln Asp Leu Tyr
    130                 135                 140

Cys Leu Asn Glu Ser Ser Lys Asn Ile Pro Leu Ala Asn Leu Gln Ile
145                 150                 155                 160

Pro Asn Cys Gly Leu Pro Ser Ala Asn Leu Ala Ala Pro Asn Leu Thr
                165                 170                 175

Val Glu Glu Gly Lys Ser Ile Thr Leu Ser Cys Ser Val Ala Gly Asp
            180                 185                 190

Pro Val Pro Asn Met Tyr Trp Asp Val Gly Asn Leu Val Ser Lys His
    195                 200                 205

Met Asn Glu Thr Ser His Thr Gln Gly Ser Leu Arg Ile Thr Asn Ile
210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
            245                 250                 255

Thr Ile Thr Phe Leu Glu Ser Pro Thr Ser Asp His His Trp Cys Ile
            260                 265                 270

Pro Phe Thr Val Lys Gly Asn Pro Lys Pro Ala Leu Gln Trp Phe Tyr
    275                 280                 285

Asn Gly Ala Ile Leu Asn Glu Ser Lys Tyr Ile Cys Thr Lys Ile His
    290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Ile Ala Lys Asn Glu Tyr
                325                 330                 335

Gly Lys Asp Glu Lys Gln Ile Ser Ala His Phe Met Gly Trp Pro Gly
            340                 345                 350

Ile Asp Asp Gly Ala Asn Pro Asn Tyr Pro Asp Val Ile Tyr Glu Asp
            355                 360                 365

Tyr Gly Thr Ala Ala Asn Asp Ile Gly Asp Thr Thr Asn Arg Ser Asn
    370                 375                 380

Glu Ile Pro Ser Thr Asp Val Thr Asp Lys Thr Gly Arg Glu His
385                 390                 395

<210> SEQ ID NO 55
<211> LENGTH: 5

```
<212> TYPE: PRT
<213> ORGANISM: Homo sapiens

<400> SEQUENCE: 55

Gly Tyr Trp Met His
1               5

<210> SEQ ID NO 56
<211> LENGTH: 17
<212> TYPE: PRT
<213> ORGANISM: Mus <mouse, genus>
<220> FEATURE:
<223> OTHER INFORMATION: 277 H-CDR2

<400> SEQUENCE: 56

Tyr Ile Asn Pro Ser Thr Asp Tyr Thr Glu Tyr Asn Gln Lys Phe Lys
1               5                   10                  15

Asp

<210> SEQ ID NO 57
<211> LENGTH: 6
<212> TYPE: PRT
<213> ORGANISM: Mus <mouse, genus>
<220> FEATURE:
<223> OTHER INFORMATION: 277 H-CDR3

<400> SEQUENCE: 57

Ser Arg Thr Gly Asn Tyr
1               5

<210> SEQ ID NO 58
<211> LENGTH: 7
<212> TYPE: PRT
<213> ORGANISM: Mus <mouse, genus>
<220> FEATURE:
<223> OTHER INFORMATION: 277 H-CDR1

<400> SEQUENCE: 58

Gly Tyr Thr Phe Thr Gly Tyr
1               5

<210> SEQ ID NO 59
<211> LENGTH: 6
<212> TYPE: PRT
<213> ORGANISM: Mus <mouse, genus>
<220> FEATURE:
<223> OTHER INFORMATION: 277 H-CDR2

<400> SEQUENCE: 59

Asn Pro Ser Thr Asp Tyr
1               5

<210> SEQ ID NO 60
<211> LENGTH: 6
<212> TYPE: PRT
<213> ORGANISM: Mus <mouse, genus>
<220> FEATURE:
<223> OTHER INFORMATION: 277 H-CDR3 Chothia

<400> SEQUENCE: 60

Ser Arg Thr Gly Asn Tyr
1               5

<210> SEQ ID NO 61
<211> LENGTH: 409
<212> TYPE: PRT
```

<213> ORGANISM: Homo sapiens
<220> FEATURE:
<223> OTHER INFORMATION: Extracellular domain of human TrkB

<400> SEQUENCE: 61

```
Cys Pro Thr Ser Cys Lys Cys Ser Ala Ser Arg Ile Trp Cys Ser Asp
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Phe Ile Ala Asn Gln Lys Arg Leu
        35                  40                  45

Glu Ile Ile Asn Glu Asp Val Glu Ala Tyr Val Gly Leu Arg Asn
    50                  55                  60

Leu Thr Ile Val Asp Ser Gly Leu Lys Phe Val Ala His Lys Ala Phe
65                  70                  75                  80

Leu Lys Asn Ser Asn Leu Gln His Ile Asn Phe Thr Arg Asn Lys Leu
                85                  90                  95

Thr Ser Leu Ser Arg Lys His Phe Arg His Leu Asp Leu Ser Glu Leu
            100                 105                 110

Ile Leu Val Gly Asn Pro Phe Thr Cys Ser Cys Asp Ile Met Trp Ile
            115                 120                 125

Lys Thr Leu Gln Glu Ala Lys Ser Ser Pro Asp Thr Gln Asp Leu Tyr
        130                 135                 140

Cys Leu Asn Glu Ser Ser Lys Asn Ile Pro Leu Ala Asn Leu Gln Ile
145                 150                 155                 160

Pro Asn Cys Gly Leu Pro Ser Ala Asn Leu Ala Ala Pro Asn Leu Thr
                165                 170                 175

Val Glu Glu Gly Lys Ser Ile Thr Leu Ser Cys Ser Val Ala Gly Asp
            180                 185                 190

Pro Val Pro Asn Met Tyr Trp Asp Val Gly Asn Leu Val Ser Lys His
        195                 200                 205

Met Asn Glu Thr Ser His Thr Gln Gly Ser Leu Arg Ile Thr Asn Ile
    210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255

Thr Ile Thr Phe Leu Glu Ser Pro Thr Ser Asp His His Trp Cys Ile
            260                 265                 270

Pro Phe Thr Val Lys Gly Asn Pro Lys Pro Ala Leu Gln Trp Phe Tyr
        275                 280                 285

Asn Gly Ala Ile Leu Asn Glu Ser Lys Tyr Ile Cys Thr Lys Ile His
    290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Ile Ala Lys Asn Glu Tyr
                325                 330                 335

Gly Lys Asp Glu Lys Gln Ile Ser Ala His Phe Met Gly Trp Pro Gly
            340                 345                 350

Ile Asp Asp Gly Ala Asn Pro Asn Tyr Pro Asp Val Ile Tyr Glu Asp
        355                 360                 365

Tyr Gly Thr Ala Ala Asn Asp Ile Gly Asp Thr Thr Asn Arg Ser Asn
    370                 375                 380

Glu Ile Pro Ser Thr Asp Val Thr Asp Lys Thr Gly Arg Glu His Ala
```

-continued

```
        385                 390                 395                 400
Gly Ser Ala His His His His His His
                            405
```

ANTI-TRKB ANTIBODIES

SEQUENCE LISTING

The instant application contains a Sequence Listing which has been submitted electronically in ASCII format and is hereby incorporated by reference in its entirety. Said ASCII file, created on Jun. 30, 2020, is named 01-3274-US-2-2020-08-26-SL.txt and is 116,412 bytes in size.

FIELD OF THE INVENTION

This invention generally relates to agonistic anti-TrkB antibodies for diagnostic and therapeutic use and in particular to humanized agonistic anti-TrkB antibodies. More specifically, agonistic anti-TrkB antibodies and methods of use for the treatment of various diseases or disorders are disclosed. Pharmaceutical compositions and kits comprising the agonistic anti-TrkB antibody are also disclosed.

BACKGROUND OF THE INVENTION

Tropomyosin receptor kinase B (TrkB), also known as tyrosine receptor kinase B, or BDNF/NT-3 growth factors receptor or neurotrophic tyrosine kinase, receptor, type 2, is a protein that in humans is encoded by the NTRK2 gene (Genbank ID: 4915). TrkB is a receptor for brain-derived neurotrophic factor (BDNF).

The neurotrophic tyrosine kinase receptor B (TrkB; gene symbol: NTRK2) is expressed by retinal neurons and glial cells. In the normal retina, TrkB signaling counteracts cell stress and promotes cell survival. In the diseased eye, such as in diabetic retinopathy or geographic atrophy, loss and functional impairments of retinal neurons and glial cells occur which cause visual impairments and vision loss. Activating TrkB signaling above the basal level (which is reduced in diabetic retinopathy), can counteract the loss and functional impairments of neurons and glial cells, thus improving visual function. Furthermore, TrkB activation has the potential to regenerate lost synaptic connections in the diseased eye, thereby promoting the regain of visual function. Upon ligand binding, TrkB undergoes homodimerization followed by autophosphorylation. Dependent on the phosphorylation sites (Y516, Y702, Y706, Y707 or Y817) different signal transduction pathways are activated, including the activity of PLCγ1 or different subforms of AKT and ERK which regulate distinct overlapping signalling cascades inducing axonal/neurite outgrowth, increasing synaptic plasticity, or increasing cell survival.

Agonistic anti-TrkB antibodies have been described in the US20100196390 and US20100150914 as well as their proposed use in the treatment of e.g. Charcot-Marie-Tooth disease or diabetes.

However, there remains a significant need for new potent agonistic anti-TrkB antibodies that can be used to activate the TrkB pathway and thereby allow their use in therapeutic interventions of e.g. neurodegenerative and psychiatric disorders.

SUMMARY OF THE INVENTION

The present invention provides monoclonal antibodies that specifically bind to human TrkB. In one aspect, the antibodies of the present invention have agonistic activity and induce TrkB phosphorylation and/or activation. In another aspect, the antibodies of the present invention are useful, for example for the treatment of eye or retinal diseases such as, geographic atrophy secondary to age-related macular degeneration, diabetic retinopathy, glaucoma, and/or diabetic macular edema.

In another aspect, the present invention provides an anti-TrkB antibody, in particular a humanized anti-TrkB antibody, having one or more of the properties described herein below.

In another aspect, an anti-TrkB antibody of the present invention binds with high affinity to human TrkB. In an embodiment relating to this aspect, an anti-TrkB antibody of the present invention binds to human TrkB at a $K_D$<10 nM. In another embodiment, an anti-TrkB antibody of the present invention binds to human TrkB at a $K_D$<5 nM.

In another aspect, an anti-TrkB antibody of the present invention activates TrkB with high potency. In an embodiment relating to this aspect, an anti-TrkB antibody of the present invention activates human TrkB with an $EC_{50}$<100 pM. In a further embodiment, an anti-TrkB antibody of the present invention activates human TrkB with an $EC_{50}$<50 pm.

In another aspect, an anti-TrkB antibody of the present invention is more potent in inducing activation of TrkB downstream signaling pathways than the natural TrkB ligand, BDNF. In a further aspect, an anti-TrkB antibody of the present invention regulates gene expression through TrkB-mediated signaling pathways in a comparable pattern to that of BDNF.

In a further aspect, an anti-TrkB antibody of the present invention binds a novel epitope in the extracellular domain of human TrkB. In a further aspect, an anti-TrkB antibody of the present invention does not cross-react with TrkB from other species, in particular does not cross-react with rodent TrkB.

In one aspect, an anti-TrkB antibody of the present invention can be formulated to high concentrations for intravitreal injections into the eye.

In a further aspect, an anti-TrkB antibody of the present invention has a low immunogenicity risk as measured by the method described in example 5.

In another aspect, the CDR sequences of an anti-TrkB antibody of the present invention have low sequence liabilities as determined by the method described in example 4.

In yet another aspect, an anti-TrkB antibody of the present invention does not reduce BDNF induced ERK phosphorylation.

In a further aspect, an anti-TrkB antibody of the present invention is specific for TrkB phosphorylation and/or activation and does not unspecifically phosphorylate/activate TrkA or TrkC. In another aspect, an anti-TrkB antibody does not bind unspecifically to human VEGF.

Further aspects encompass polynucleotide(s) molecule(s) encoding antibodies of the present invention, expression vectors and viral vectors as well as host cells comprising such polynucleotide(s) molecule(s), and methods of making antibodies of the present invention. The present invention further provides therapeutic uses for the antibodies of the present invention, in particular for retinal/eye diseases.

In one embodiment, the present invention provides an anti-TrkB antibody or an antigen-binding fragment thereof comprising:
 a light chain variable region comprising the amino acid sequence of SEQ ID NO: 48 (L-CDR1); the amino acid sequence of SEQ ID NO: 49 (L-CDR2); and the amino acid sequence of SEQ ID NO: 50 (L-CDR3); and
 a heavy chain variable region comprising the amino acid sequence of SEQ ID NO: 51 (H-CDR1); the amino acid sequence of SEQ ID NO: 52 (H-CDR2); and the amino acid sequence of SEQ ID NO: 53 (H-CDR3), or a heavy chain variable region comprising the amino acid sequence of SEQ ID NO: 55 (H-CDR1); the amino acid sequence of SEQ ID NO: 56 (H-CDR2); and the amino acid sequence of SEQ ID NO: 57 (H-CDR3), or a heavy chain variable region comprising the amino acid sequence of SEQ ID NO: 58 (H-CDR1); the amino acid sequence of SEQ ID NO: 59 (H-CDR2); and the amino acid sequence of SEQ ID NO: 60 (H-CDR3).

In one embodiment, the present invention provides an anti-TrkB antibody or an antigen-binding fragment thereof comprising:

a variable light chain and a variable heavy chain comprising the amino acid sequences of SEQ ID NO: 2 and SEQ ID NO: 12, respectively, a variable light chain and a variable heavy chain comprising the amino acid sequences of SEQ ID NO: 3 and SEQ ID NO: 13, respectively, a variable light chain and a variable heavy chain comprising the amino acid sequences of SEQ ID NO: 4 and SEQ ID NO: 14, respectively, a variable light chain and a variable heavy chain comprising the amino acid sequences of SEQ ID NO: 5 and SEQ ID NO: 15, respectively, a variable light chain and a variable heavy chain comprising the amino acid sequences of SEQ ID NO: 6 and SEQ ID NO: 16, respectively, a variable light chain and a variable heavy chain comprising the amino acid sequences of SEQ ID NO: 7 and SEQ ID NO: 17, respectively, a variable light chain and a variable heavy chain comprising the amino acid sequences of SEQ ID NO: 8 and SEQ ID NO: 18, respectively, a variable light chain and a variable heavy chain comprising the amino acid sequences of SEQ ID NO: 9 and SEQ ID NO: 19, respectively, or a variable light chain and a variable heavy chain comprising the amino acid sequences of SEQ ID NO: 10 and SEQ ID NO: 20, respectively.

In one embodiment, the present invention provides an anti-TrkB antibody or an antigen-binding fragment thereof comprising:

a light chain comprising the amino acid sequence of SEQ ID NO: 21 and a heavy chain comprising the amino acid sequence of SEQ ID NO: 22 or 23, a light chain comprising the amino acid sequence of SEQ ID NO: 24 and a heavy chain comprising the amino acid sequence of SEQ ID NO: 25 or 26, a light chain comprising the amino acid sequence of SEQ ID NO: 27 and a heavy chain comprising the amino acid sequence of SEQ ID NO: 28 or 29, a light chain comprising the amino acid sequence of SEQ ID NO: 30 and a heavy chain comprising the amino acid sequence of SEQ ID NO: 31 or 32, a light chain comprising the amino acid sequence of SEQ ID NO: 33 and a heavy chain comprising the amino acid sequence of SEQ ID NO: 34 or 35, a light chain comprising the amino acid sequence of SEQ ID NO: 36 and a heavy chain comprising the amino acid sequence of SEQ ID NO: 37 or 38, a light chain comprising the amino acid sequence of SEQ ID NO: 39 and a heavy chain comprising the amino acid sequence of SEQ ID NO: 40 or 41, a light chain comprising the amino acid sequence of SEQ ID NO: 42 and a heavy chain comprising the amino acid sequence of SEQ ID NO: 43 or 44, or a light chain comprising the amino acid sequence of SEQ ID NO: 45 and a heavy chain comprising the amino acid sequence of SEQ ID NO: 46 or 47.

In a particular preferred embodiment the anti-TrkB antibody is a humanized anti-TrkB antibody.

In one embodiment, the present invention provides an anti-TrkB antibody or an antigen-binding fragment thereof for use in medicine.

In one embodiment, the present invention provides an anti-TrkB antibody or an antigen-binding fragment thereof for use in the treatment of retinal or eye diseases.

In one embodiment, the present invention provides an anti-TrkB antibody or an antigen-binding fragment thereof for use in the treatment of neural/neuronal eye or retinal diseases.

In one embodiment, the present invention provides an anti-TrkB antibody or an antigen-binding fragment thereof for use in the treatment of geographic atrophy.

In one embodiment, the present invention provides an anti-TrkB antibody or an antigen-binding fragment thereof for use in the treatment of age-related macular degeneration or diabetic retinopathy.

In one embodiment, the present invention provides a pharmaceutical composition comprising an anti-TrkB antibody or an antigen-binding fragment thereof and a pharmaceutically acceptable carrier.

In one embodiment, the present invention provides an anti-TrkB antibody or an antigen-binding fragment thereof or a pharmaceutical composition comprising the anti-TrkB antibody or an antigen-binding fragment thereof, wherein said antibody or antigen-binding fragment thereof is administered by a parenteral route, intravenous route, intravitreal route or subcutaneous route of administration.

In one embodiment, the present invention provides an isolated polynucleotide or polynucleotides comprising a sequence encoding a light chain or light chain variable region of an antibody or antigen-binding fragment thereof and a heavy chain or heavy chain variable region of an antibody or antigen-binding fragment thereof.

In one embodiment, the present invention provides an expression vector comprising an isolated polynucleotide or polynucleotides encoding a light chain or light chain variable region of an antibody or antigen-binding fragment thereof and a heavy chain or heavy chain variable region of an antibody or antigen-binding fragment thereof.

In one embodiment, the present invention provides a viral vector comprising an isolated polynucleotide or polynucleotides encoding a light chain or light chain variable region of an antibody or antigen-binding fragment thereof and a heavy chain or heavy chain variable region of an antibody or antigen-binding fragment thereof.

In one embodiment, the present invention provides a host cell comprising an expression vector or an isolated polynucleotide or polynucleotides encoding a light chain or light chain variable region of an antibody or antigen-binding fragment thereof and a heavy chain or heavy chain variable region of an antibody or antigen-binding fragment thereof.

In one embodiment, the present invention provides a method for producing an anti-TrkB antibody or an antigen-binding fragment thereof comprising:

obtaining a host cell comprising an expression vector or an isolated polynucleotide or polynucleotides encoding a light chain or light chain variable region of an antibody or antigen-binding fragment thereof and a heavy chain or heavy chain variable region of an antibody or antigen-binding fragment thereof; and cultivating the host cell.

In one embodiment, the method for producing an anti-TrkB antibody or antigen-binding fragment thereof further comprises recovering and purifying the anti-TrkB antibody or antigen-binding fragment thereof.

In one embodiment, the present invention provides an anti-TrkB antibody or antigen-binding fragment thereof that binds to at least one amino acid residue within amino acid regions 92-112, 130-143 and/or 205-219 of the extracellular domain of human TrkB with the SEQ ID NO: 54.

In one embodiment, the present invention provides an anti-TrkB antibody or antigen-binding fragment thereof that binds to at least one amino acid residue within amino acid regions 92-112 and 130-143; or 92-112 and 205-219; or 130-143 and 205-219; or 92-112 and 130-143 and 205-219 of the extracellular domain of human TrkB with the SEQ ID NO: 54.

In one embodiment, the present invention provides an anti-TrkB antibody or antigen-binding fragment thereof that binds to at least one amino acid residue within any of the aforementioned combinations and further also to at least one amino acid residue within amino acid regions 313-330 and/or 348-367 of the extracellular domain of human TrkB with the SEQ ID NO: 54.

In one embodiment, the present invention provides an anti-TrkB antibody or antigen-binding fragment thereof that binds to at least one amino acid residue within amino acid regions 92-112, 130-143, 205-219, 313-330 and 348-367 of the extracellular domain of human TrkB with the SEQ ID NO: 54.

BRIEF DESCRIPTION OF THE DRAWINGS

FIG. 1: Epitope mapping of BDNF, 277-antibody, C2 or C20 antibodies to the extracellular domain of human TrkB (SEQ ID NO: 61).

DETAILED DESCRIPTION OF THE INVENTION

Definitions

Figure 2:
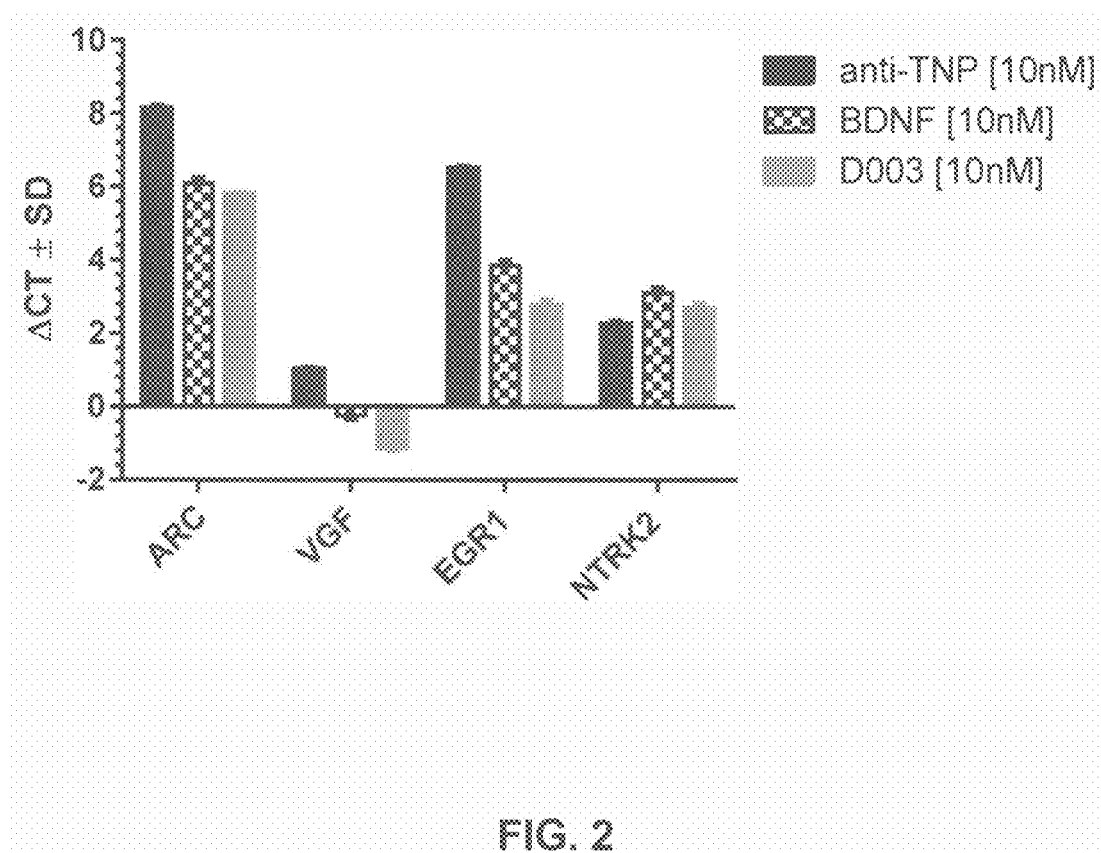
FIG. 2: qPCR expression data (y-axis) for regulated genes (x-axis) with regard to synaptic plasticity in SH-SY5Y cells after treatment with BDNF, control IgG1 (anti-2,4,6-trinitrophenyl, anti-TNP) or D003 antibody.

The generalized structure of antibodies or immunoglobulin is well known to those of skill in the art, these molecules are heterotetrameric glycoproteins, typically of about 150,000 daltons, composed of two identical light (L) chains and two identical heavy (H) chains. Each light chain is covalently linked to a heavy chain by one disulfide bond to form a heterodimer, and the heterotrimeric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain ($V_H$=variable heavy chain), followed by three or four constant domains ($C_{H1}$, $C_{H2}$, $C_{H3}$, and $C_{H4}$), as well as a hinge region between $C_{H1}$ and $C_{H2}$. Each light chain has two domains, an amino-terminal variable domain ($V_L$=variable light chain) and a carboxy-terminal constant domain (CL). The $V_L$ domain associates non-covalently with the $V_H$ domain, whereas the $C_L$ domain is commonly covalently linked to the $C_{H1}$ domain via a disulfide bond. Particular amino acid residues are believed to form an interface between the light and heavy chain variable domains (Chothia et al., 1985, J. Mol. Biol. 186:651-663.)

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5$^{th}$ Ed. Public Health Service, National Institutes of Health, Bethesda, Md., whereas HVLs are structurally defined according to the three-dimensional structure of the variable domain, as described by Chothia and Lesk, 1987, J. Mol. Biol. 196: 901-917. Where these two methods result in slightly different identifications of a CDR, the structural definition is preferred. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

FR residues and Ig constant domains are not directly involved in antigen binding, but contribute to antigen binding and/or mediate antibody effector function. Some FR residues are thought to have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody-dependent cellular cytotoxicity (ADCC), complement-dependent cytotoxicity (CDC) and antibody-dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, $IgG_4$, $IgA_1$, and $IgA_2$, respectively. The heavy chain constant domains that correspond to the different classes of immunoglobulins are called α, δ, ε, γ, and μ, respectively. The subunit structures and three-dimensional configurations of the classes of native immunoglobulins are well known.

The terms, "antibody", "anti-TrkB antibody", "humanized anti-TrkB antibody", and "variant humanized anti-TrkB antibody" are used herein in the broadest sense and specifically encompass monoclonal antibodies (including full length monoclonal antibodies), multispecific antibodies (e.g., bispecific antibodies), antibodies with minor modifications such as N- or C-terminal truncations and antibody fragments such as variable domains and other portions of antibodies that exhibit a desired biological activity, e.g., TrkB binding.

The term "monoclonal antibody" (mAb) refers to an antibody of a population of substantially homogeneous antibodies; that is, the individual antibodies in that population are identical except for naturally occurring mutations that may be present in minor amounts. Monoclonal antibodies are highly specific, being directed against a single antigenic determinant, an "epitope". Therefore, the modifier "monoclonal" is indicative of a substantially homogeneous population of antibodies directed to the identical epitope and is not to be construed as requiring production of the antibody by any particular method. It should be understood that monoclonal antibodies can be made by any technique or methodology known in the art; including e.g., the hybridoma method (Kohler et al., 1975, Nature 256:495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus or germline sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The terms, "antibody fragment", "antigen binding fragment", "anti-TrkB antibody fragment", "humanized anti-TrkB antibody fragment", "variant humanized anti-TrkB antibody fragment" refer to a portion of a full length anti-TrkB antibody, in which a variable region or a functional capability is retained, for example, specific TrkB epitope binding. Examples of antibody fragments include, but are not limited to, a Fab, Fab', $F(ab')_2$, Fd, Fv, scFv and scFv-Fc fragment, a diabody, a linear antibody, a single-chain antibody, a minibody, a diabody formed from antibody fragments, and multispecific antibodies formed from antibody fragments.

Full length antibodies can be treated with enzymes such as papain or pepsin to generate useful antibody fragments. Papain digestion is used to produce two identical antigen-binding antibody fragments called "Fab" fragments, each with a single antigen-binding site, and a residual "Fc" fragment. The Fab fragment also contains the constant domain of the light chain and the $C_{H1}$ domain of the heavy chain. Pepsin treatment yields a $F(ab')_2$ fragment that has two antigen-binding sites and is still capable of cross-linking antigen.

Fab' fragments differ from Fab fragments by the presence of additional residues including one or more cysteines from the antibody hinge region at the C-terminus of the $C_{H1}$ domain. $F(ab')_2$ antibody fragments are pairs of Fab' fragments linked by cysteine residues in the hinge region. Other chemical couplings of antibody fragments are also known.

"Fv" fragment contains a complete antigen-recognition and binding site consisting of a dimer of one heavy and one light chain variable domain in tight, non-covalent association. In this configuration, the three CDRs of each variable domain interact to define an antigen-biding site on the surface of the $V_H$-$V_L$ dimer. Collectively, the six CDRs confer antigen-binding specificity to the antibody.

A "single-chain Fv" or "scFv" antibody fragment is a single chain Fv variant comprising the $V_H$ and $V_L$ domains of an antibody where the domains are present in a single polypeptide chain. The single chain Fv is capable of recognizing and binding antigen. The scFv polypeptide may optionally also contain a polypeptide linker positioned between the $V_H$ and $V_L$ domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

Other recognized antibody fragments include those that comprise a pair of tandem Fd segments ($V_H$-$C_{H1}$-$V_H$-$C_{H1}$) to form a pair of antigen binding regions. These "linear antibodies" can be bispecific or monospecific as described in, for example, Zapata et al. 1995, Protein Eng. 8(10):1057-1062.

A humanized antibody or a humanized antibody fragment is a specific type of chimeric antibody which includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or HVLs of a non-human antibody, inserted between the FRs of a human heavy or light chain variable domain.

The present invention describes specific humanized anti-TrkB antibodies which contain CDRs derived from the murine lead D003 inserted between the FRs of human germline sequence heavy and light chain variable domains. It will be understood that certain murine FR residues may be important to the function of the humanized antibodies and therefore certain of the human germline sequence heavy and light chain variable domains residues are modified to be the same as those of the corresponding murine sequence.

In one aspect, a humanized anti-TrkB antibody comprises substantially all of at least one, and typically two, variable domains (such as contained, for example, in Fab, Fab', F(ab')$_2$, Fabc, and Fv fragments) in which all, or substantially all, of the CDRs correspond to those of a non-human immunoglobulin, and specifically herein, the CDRs are murine sequences of the lead D003, and the FRs are those of a human immunoglobulin consensus or germline sequence. In another aspect, a humanized anti-TrkB antibody also includes at least a portion of an immunoglobulin Fc region, typically that of a human immunoglobulin. Ordinarily, the antibody will contain both the light chain as well as at least the variable domain of a heavy chain. The antibody also may include one or more of the $C_{H1}$, hinge, $C_{H2}$, $C_{H3}$, and/or $C_{H4}$ regions of the heavy chain, as appropriate.

A humanized anti-TrkB antibody can be selected from any class of immunoglobulins, including IgM, IgG, IgD, IgA and IgE, and any isotype, including $IgG_1$, $IgG_2$, $IgG_3$, $IgG_4$, $IgA_1$ and $IgA_2$. For example, the constant domain can be a complement fixing constant domain where it is desired that the humanized antibody exhibit cytotoxic activity, and the isotype is typically $IgG_1$. Where such cytotoxic activity is not desirable, the constant domain may be of another isotype, e.g., $IgG_2$. An alternative humanized anti-TrkB antibody can comprise sequences from more than one immunoglobulin class or isotype, and selecting particular constant domains to optimize desired effector functions is within the ordinary skill in the art. In specific embodiments, the present invention provides antibodies that are $IgG_1$ antibodies and more particularly, are $IgG_1$ antibodies in which there is a knock-out of effector functions.

The FRs and CDRs, or HVLs, of a humanized anti-TrkB antibody need not correspond precisely to the parental sequences. For example, one or more residues in the import CDR, or HVL, or the consensus or germline FR sequence may be altered (e.g., mutagenized) by substitution, insertion or deletion such that the resulting amino acid residue is no longer identical to the original residue in the corresponding position in either parental sequence but the antibody nevertheless retains the function of binding to TrkB. Such alteration typically will not be extensive and will be conservative alterations. Usually, at least 75% of the humanized antibody residues will correspond to those of the parental consensus or germline FR and import CDR sequences, more often at least 90%, and most frequently greater than 95%, or greater than 98% or greater than 99%.

Immunoglobulin residues that affect the interface between heavy and light chain variable regions ("the $V_L$-$V_H$ interface") are those that affect the proximity or orientation of the two chains with respect to one another. Certain residues that may be involved in interchain interactions include $V_L$ residues 34, 36, 38, 44, 46, 87, 89, 91, 96, and 98 and $V_H$ residues 35, 37, 39, 45, 47, 91, 93, 95, 100, and 103 (utilizing the numbering system set forth in Kabat et al., Sequences of Proteins of Immunological Interest (National Institutes of Health, Bethesda, Md., 1987)). U.S. Pat. No. 6,407,213 also discusses that residues such as $V_L$ residues 43 and 85, and $V_H$ residues 43 and 60 also may be involved in this interaction. While these residues are indicated for human IgG only, they are applicable across species. Important antibody residues that are reasonably expected to be involved in interchain interactions are selected for substitution into the consensus sequence.

The terms "consensus sequence" and "consensus antibody" refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Kabat et al., 1991, Sequences of Proteins of Immunological Interest, 5th Ed. Public Health Service, National Institutes of Health, Bethesda, Md., and variants thereof. The FRs of heavy and light chain consensus sequences, and variants thereof, provide useful sequences for the preparation of humanized anti-TrkB antibodies. See, for example, U.S. Pat. Nos. 6,037,454 and 6,054,297.

Human germline sequences are found naturally in human population. A combination of those germline genes generates antibody diversity. Germline antibody sequences for the light chain of the antibody come from conserved human germline kappa or lambda v-genes and j-genes. Similarly the heavy chain sequences come from germline v-, d- and j-genes (LeFranc, M-P, and LeFranc, G, "The Immunoglobulin Facts Book" Academic Press, 2001).

An "isolated" antibody is one that has been identified and separated and/or recovered from a component of its natural environment. Contaminant components of the antibody's natural environment are those materials that may interfere with diagnostic or therapeutic uses of the antibody, and can be enzymes, hormones, or other proteinaceous or nonproteinaceous solutes. In one aspect, the antibody will be purified to at least greater than 95% isolation by weight of antibody.

An isolated antibody includes an antibody in situ within recombinant cells in which it is produced, since at least one component of the antibody's natural environment will not be present. Ordinarily however, an isolated antibody will be prepared by at least one purification step in which the recombinant cellular material is removed.

The term "antibody performance" refers to factors/properties that contribute to antibody recognition of antigen or the effectiveness of an antibody in vivo. Changes in the amino acid sequence of an antibody can affect antibody properties such as folding, and can influence physical factors such as initial rate of antibody binding to antigen ($k_a$), dissociation constant of the antibody from antigen ($k_d$), affinity constant of the antibody for the antigen (Kd), conformation of the antibody, protein stability, and half life of the antibody.

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers can be used.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers.

The term "mammal" for purposes of treatment refers to any animal classified as a mammal, including humans, domesticated and farm animals, and zoo, sports, or pet animals, such as dogs, horses, cats, cows, and the like. Preferably, the mammal is human.

A "disorder", as used herein, is any condition that would benefit from treatment with a humanized anti-TrkB antibody described herein. This includes chronic and acute disorders or diseases including those pathological conditions that predispose the mammal to the disorder in question. Non-limiting examples or disorders to be treated herein include eye or retinal disorders.

As used herein, the term "TrkB-associated disorder" or "TrkB-associated disease" refers to a condition in which modification or activation of cells expressing TrkB is indicated. A TrkB-associated disorder includes diseases and disorders such as age-related macular degeneration, geographic atrophy, diabetic retinopathy, diabetic macular edema, retinitis pigmentosa, inherited retinal dystrophy, inherited macular dystrophy, myopic degeneration, retinal vein occlusions, retinal artery occlusions, endophthalmitis, uveitis, cystoid macular edema, choroidal neovascular membrane secondary to any retinal diseases, optic neuropathies, glaucoma, retinal detachment, toxic retinopathy, radiation retinopathy, and traumatic retinopathy as well as prodromal and mild-to-moderate alzheimer's diseases, delaying disease progression of patients with Alzheimer's disease, Huntington's disease, Parkinson's disease, major depressive disorder, schizophrenia, cognitive impairment associated with schizophrenia, prevention of first-episode psychosis in individuals with attenuated psychosis syndrome, prevention of relapse in patients with schizophrenia, treatment-resistant depression, and metabolic diseases like hyperphagia, obesity or metabolic syndrome.

The term "intravitreal injection" has its normal meaning in the art and refers to introduction of an anti-TrkB antibody or antigen-binding fragment thereof into the vitreous of a patient.

The term "subcutaneous administration" refers to introduction of an anti-TrkB antibody or antigen-binding fragment thereof under the skin of an animal or human patient, preferable within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue.

The term "therapeutically effective amount" is used to refer to an amount of an anti-TrkB antibody or antigen-binding fragment thereof that relieves or ameliorates one or more of the symptoms of the disorder being treated. In doing so it is that amount that has a beneficial patient outcome. In one aspect, the therapeutically effective amount has a neuroprotective or neuroregenerative effect. In another aspect, the therapeutically effective amount refers to a target serum concentration that has been shown to be effective in, for example, slowing disease progression. Efficacy can be measured in conventional ways, depending on the condition to be treated. For example, in eye/retinal diseases or disorders characterized by cells expressing TrkB, efficacy can be measured by determining the response rates, e.g. restoration of vision or by assessing the time of delay until disease progression.

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an anti-TrkB antibody or antigen-binding fragment thereof prior to or following the onset of a symptom of a disease or disorder thereby preventing or removing one or more signs of the disease or disorder. As another example, the term includes the administration of an anti-TrkB antibody or antigen-binding fragment thereof after clinical manifestation of the disease to combat the symptoms of the disease. Further, administration of an anti-TrkB antibody or antigen-binding fragment thereof after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the anti-TrkB antibody composition or antigen-binding fragment thereof, the result should be considered an effective treatment of the underlying disorder regardless of whether all the symptoms of the disorder are alleviated or not.

The term "package insert" is used to refer to instructions customarily included in commercial packages of therapeutic products, that contain information about the indications, usage, administration, contraindications and/or warnings concerning the use of such therapeutic products.

Antibodies

Described and disclosed herein are anti-TrkB antibodies, in particular humanized anti-TrkB antibodies as well as compositions and articles of manufacture comprising anti-TrkB antibodies of the present invention. Also described are antigen-binding fragments of an anti-TrkB antibody. The anti-TrkB antibodies and antigen-binding fragments thereof can be used in the treatment of a variety of diseases or disorders characterized by reduced activity of the TrkB pathway. An anti-TrkB antibody and an antigen-binding fragment thereof each include at least a portion that specifically recognizes a TrkB epitope.

In an initial characterization the anti-TrkB murine lead D003 was selected based on its superior antibody performance. A library of variants was generated by placing the CDRs of the murine lead into FRs of the human consensus heavy and light chain variable domains and furthermore by engineering the FRs with different alterations.

This resulted in various humanized heavy and light chain variable sequences as shown below:

VL Sequences

```
D003_VL (murine lead), variable light chain,
                                                    SEQ ID NO: 1
DIVMSQSPSSLAVSVGEKVTMSCKSSQSLLYSSNQKNYLAWYQQKPGQSPKLLIYWASTRES
GVP DRFTGSGSGTDFTLTISSVKAEDLAVYYCQQYYSYPYTFGGGTKLEIK 277-gr_VL, (humanized) variable light chain,
                                                    SEQ ID NO: 2
DIVMTQSPDSLAVSLGERATINCKSSQSLLYSSNQKNYLAWYQQKPGQPPKLLIYWASTRESG
VPDRFSGSGSGTDFTLTISSLQAEDVAVYYCQQYYSYPYTFGQGTKLEIK 277-33_VL: (humanized) variable light chain,
                                                    SEQ ID NO: 3
DIVMTQSPDSLAVSLGERATISCKSSQSLLYSSNQKNYLAWYQQKPGQPPKLLIYWASTRESG
VPDRFSGSGSGTDFTLTISSLQAEDVAVYYCQQYYSYPYTFGGGTKLEIK 277-35_VL: (humanized) variable light chain,
                                                    SEQ ID NO: 4
DIVMTQSPDSLAVSLGERATISCKSSQSLLYSSNQKNYLAWYQQKPGQPPKLLIYWASTRESG
VPDRFSGSGSGTDFTLTISSLQAEDVAVYYCQQYYSYPYTFGGGTKLEIK
```

-continued 277-42_VL, (humanized) variable light chain,
SEQ ID NO: 5
DIVMTQSPDSLAVSLGERATINCKSSQSLLYSSNQKNYLAWYQQKPGQPPKLLIYWASTRESG
VPDRFSGSGSGTDFTLTISSLQAEDVAVYYCQQYYSYPYTFGGGTKLEIK 277-44_VL, (humanized) variable light chain,
SEQ ID NO: 6
DIVMTQSPDSLAVSLGERATINCKSSQSLLYSSNQKNYLAWYQQKPGQSPKLLIYWASTRESG
VPDRFSGSGSGTDFTLTISSLQAEDVAVYYCQQYYSYPYTFGQGTKLEIK 277-48_VL, (humanized) variable light chain,
SEQ ID NO: 7
DIVMTQSPDSLAVSLGERATINCKSSQSLLYSSNQKNYLAWYQQKPGQPPKLLIYWASTRESG
VPDRFSGSGSGTDFTLTISSLQAEDVAVYYCQQYYSYPYTFGQGTKLEIK 277-51_VL, (humanized) variable light chain,
SEQ ID NO: 8
DIVMTQSPDSLAVSLGERATISCKSSQSLLYSSNQKNYLAWYQQKPGQPPKLLIYWASTRESG
VPDRFSGSGSGTDFTLTISSLQAEDVAVYYCQQYYSYPYTFGGGTKLEIK 277-64_VL, (humanized) variable light chain,
SEQ ID NO: 9
DIVMTQSPDSLAVSLGERATISCKSSQSLLYSSNQKNYLAWYQQKPGQPPKLLIYWASTRESG
VPDRFSGSGSGTDFTLTISSLQAEDVAVYYCQQYYSYPYTFGQGTKLEIK 277-67_VL, (humanized) variable light chain,
SEQ ID NO: 10
DIVMTQSPDSLAVSLGERATINCKSSQSLLYSSNQKNYLAWYQQKPGQSPKLLIYWASTRESG
VPDRFSGSGSGTDFTLTISSLQAEDVAVYYCQQYYSYPYTFGQGTKLEIK VH Sequences D003_VH, (murine lead) variable heavy chain,
SEQ ID NO: 11
QVQLQQSGAELAKPGASVKMSCKASGYTFTGYWMHWVKQRPGQGLEWIGYINPSTDYTEYN
QKFKDKATLTADKSSSTAYMQLSSLTSEDSAVYYCARSRTGNYWGQGTTLTVSS 277-gr_VH, (humanized) variable heavy chain,
SEQ ID NO: 12
QVQLVQSGAEVKKPGASVKVSCKASGYTFTGYWMHWVRQAPGQGLEWMGYINPSTDYTEY
NQKFKDRVTMTRDTSTSTVYMELSSLRSEDTAVYYCARSRTGNYWGQGTLVTVSS 277-33_VH, (humanized) variable heavy chain,
SEQ ID NO: 13
QVQLVQSGAEVKKPGASVKVSCKASGYTFTGYWMHWVRQRPGQGLEWIGYINPSTDYTEYN
QKFKDRVTLTRDTSTSTVYMELSSLTSEDTAVYYCARSRTGNYWGQGTTVTVSS 277-35_VH, (humanized) variable heavy chain,
SEQ ID NO: 14
QVQLVQSGAEVKKPGASVKVSCKASGYTFTGYWMHWVRQRPGQGLEWIGYINPSTDYTEYN
QKFKDRVTLTRDTSTSTVYMELSSLRSEDTAVYYCARSRTGNYWGQGTTVTVSS 277-42_VH, (humanized) variable heavy chain,
SEQ ID NO: 15
QVQLVQSGAEVKKPGASVKVSCKASGYTFTGYWMHWVRQRPGQGLEWIGYINPSTDYTEYN
QKFKDRVTLTRDTSTSTVYMELSSLRSEDTAVYYCARSRTGNYWGQGTTVTVSS 277-44_VH, (humanized) variable heavy chain,
SEQ ID NO: 16
QVQLVQSGAEVKKPGASVKVSCKASGYTFTGYWMHWVRQAPGQGLEWIGYINPSTDYTEYN
QKFKDRVTMTRDTSTSTVYMELSSLTSEDTAVYYCARSRTGNYWGQGTTVTVSS 277-48_VH, (humanized) variable heavy chain,
SEQ ID NO: 17
QVQLVQSGAEVKKPGASVKVSCKASGYTFTGYWMHWVRQRPGQGLEWIGYINPSTDYTEYN
QKFKDRVTMTRDTSTSTVYMELSSLRSEDTAVYYCARSRTGNYWGQGTTVTVSS 277-51_VH, (humanized) variable heavy chain,
SEQ ID NO: 18
QVQLVQSGAEVKKPGASVKVSCKASGYTFTGYWMHWVRQRPGQGLEWIGYINPSTDYTEYN
QKFKDRATLTRDTSTSTVYMELSSLRSEDTAVYYCARSRTGNYWGQGTTVTVSS 277-64_VH, (humanized) variable heavy chain,
SEQ ID NO: 19
QVQLVQSGAEVKKPGASVKVSCKASGYTFTGYWMHWVRQAPGQGLEWIGYINPSTDYTEYN
QKFKDRVTMTRDTSTSTVYMELSSLRSEDTAVYYCARSRTGNYWGQGTTVTVSS -continued 277-67_VH, (humanized) variable heavy chain,
SEQ ID NO: 20
QVQLVQSGAEVKKPGASVKVSCKASGYTFTGYWMHWVRQAPGQGLEWIGYINPSTDYTEYN
QKFKDRVTMTRDTSTSTVYMELSSLRSEDTAVYYCARSRTGNYWGQGTTVTVSS The underlined sequences correspond to the CDR regions of the variable light and heavy chain regions.

Humanized anti-TrkB antibodies of the present invention are those that have the light and heavy chain sequences as set forth in the following table. IgG1-KO mutants have been made by introducing two mutations in the Fc region, Leu232Ala and Leu233Ala to reduce effector function.

TABLE 1

| Antibody | Sequence | SEQ ID NO: |
|---|---|---|
| 277-gr (Light Chain, IgG1) | DIVMTQSPDSLAVSLGERATINCKSSQSLLYSSNQKNY LAWYQQKPGQPPKLLIYWASTRESGVPDRFSGSGSGTD FTLTISSLQAEDVAVYYCQQYYSYPYTFGQGTKLEIKR TVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC | 21 |
| 277-gr (Heavy Chain, IgG1) | QVQLVQSGAEVKKPGASVKVSCKASGYTFTGYWMHWVR QAPGQGLEWMGYINPSTDYTEYNQKFKDRVTMTRDTST STVYMELSSLRSEDTAVYYCARSRTGNYWGQGTLVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 22 |
| 277-gr (Heavy Chain, IgG1-KO) | QVQLVQSGAEVKKPGASVKVSCKASGYTFTGYWMHWVR QAPGQGLEWMGYINPSTDYTEYNQKFKDRVTMTRDTST STVYMELSSLRSEDTAVYYCARSRTGNYWGQGTLVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APEAAGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 23 |
| 277-33 (Light Chain, IgG1) | DIVMTQSPDSLAVSLGERATISCKSSQSLLYSSNQKNY LAWYQQKPGQPPKLLIYWASTRESGVPDRFSGSGSGTD FTLTISSLQAEDVAVYYCQQYYSYPYTFGGGTKLEIKR TVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC | 24 |
| 277-33 (Heavy Chain, IgG1) | QVQLVQSGAEVKKPGASVKVSCKASGYTFTGYWMHWVR QRPGQGLEWIGYINPSTDYTEYNQKFKDRVTLTRDTST STVYMELSSLTSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 25 |
| 277-33 (Heavy Chain, IgG1-KO) | QVQLVQSGAEVKKPGASVKVSCKASGYTFTGYWMHWVR QRPGQGLEWIGYINPSTDYTEYNQKFKDRVTLTRDTST STVYMELSSLTSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APEAAGGPSVFLFPPKPKDTLMISRTPEVTCVVVDVSH | 26 |

TABLE 1-continued

| Antibody | Sequence | SEQ ID NO: |
|---|---|---|
| | EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | |
| 277-35 (Light Chain, IgG1) | DIVMTQSPDSLAVSLGERATISCKSSQSLLYSSNQKNY LAWYQQKPGQPPKLLIYWASTRESGVPDRFSGSGSGTD FTLTISSLQAEDVAVYYCQQYYSYPYTFGGGTKLEIKR TVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC | 27 |
| 277-35 (Heavy Chain, IgG1) | QVQLVQSGAEVKKPGASVKVSCKASGYTFTGYWMHWVR QRPGQGLEWIGYINPSTDYTEYNQKFKDRVTLTRDTST STVYMELSSLRSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 28 |
| 277-35 (Heavy Chain, IgG1-KO) | QVQLVQSGAEVKKPGASVKVSCKASGYTFTGYWMHWVR QRPGQGLEWIGYINPSTDYTEYNQKFKDRVTLTRDTST STVYMELSSLRSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APEAAGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 29 |
| 277-42 (Light Chain, IgG1) | DIVMTQSPDSLAVSLGERATINCKSSQSLLYSSNQKNY LAWYQQKPGQPPKLLIYWASTRESGVPDRFSGSGSGTD FTLTISSLQAEDVAVYYCQQYYSYPYTFGGGTKLEIKR TVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC | 30 |
| 277-42 (Heavy Chain, IgG1) | QVQLVQSGAEVKKPGASVKVSCKASGYTFTGYWMHWVR QRPGQGLEWIGYINPSTDYTEYNQKFKDRVTLTRDTST STVYMELSSLRSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 31 |
| 277-42 (Heavy Chain, IgG1-KO) | QVQLVQSGAEVKKPGASVKVSCKASGYTFTGYWMHWVR QRPGQGLEWIGYINPSTDYTEYNQKFKDRVTLTRDTST STVYMELSSLRSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APEAAGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 32 |
| 277-44 (Light Chain, IgG1) | DIVMTQSPDSLAVSLGERATINCKSSQSLLYSSNQKNY LAWYQQKPGQSPKLLIYWASTRESGVPDRFSGSGSGTD FTLTISSLQAEDVAVYYCQQYYSYPYTFGQGTKLEIKR TVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC | 33 |

TABLE 1-continued

| Antibody | Sequence | SEQ ID NO: |
|---|---|---|
| 277-44 (Heavy Chain, IgG1) | QVQLVQSGAEVKKPGASVKVSCKASGYTFTGYWMHWVR QAPGQGLEWIGYINPSTDYTEYNQKFKDRVTMTRDTST STVYMELSSLTSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 34 |
| 277-44 (Heavy Chain, IgG1-KO) | QVQLVQSGAEVKKPGASVKVSCKASGYTFTGYWMHWVR QAPGQGLEWIGYINPSTDYTEYNQKFKDRVTMTRDTST STVYMELSSLTSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APEAAGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 35 |
| 277-48 (Light Chain, IgG1) | DIVMTQSPDSLAVSLGERATINCKSSQSLLYSSNQKNY LAWYQQKPGQPPKLLIYWASTRESGVPDRFSGSGSGTD FTLTISSLQAEDVAVYYCQQYYSYPYTFGQGTKLEIKR TVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC | 36 |
| 277-48 (Heavy Chain, IgG1) | QVQLVQSGAEVKKPGASVKVSCKASGYTFTGYWMHWVR QRPGQGLEWIGYINPSTDYTEYNQKFKDRVTMTRDTST STVYMELSSLRSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 37 |
| 277-48 (Heavy Chain, IgG1-KO) | QVQLVQSGAEVKKPGASVKVSCKASGYTFTGYWMHWVR QRPGQGLEWIGYINPSTDYTEYNQKFKDRVTMTRDTST STVYMELSSLRSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APEAAGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 38 |
| 277-51 (Light Chain, IgG1) | DIVMTQSPDSLAVSLGERATISCKSSQSLLYSSNQKNY LAWYQQKPGQPPKLLIYWASTRESGVPDRFSGSGSGTD FTLTISSLQAEDVAVYYCQQYYSYPYTFGGGTKLEIKR TVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC | 39 |
| 277-51 (Heavy Chain, IgG1) | QVQLVQSGAEVKKPGASVKVSCKASGYTFTGYWMHWVR QRPGQGLEWIGYINPSTDYTEYNQKFKDRATLTRDTST STVYMELSSLRSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR | 40 |

TABLE 1-continued

| Antibody | Sequence | SEQ ID NO: |
|---|---|---|
| | EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | |
| 277-51 (Heavy Chain, IgG1-KO) | QVQLVQSGAEVKKPGASVKVSCKASGYTFTGYWMHWVR QRPGQGLEWIGYINPSTDYTEYNQKFKDRATLTRDTST STVYMELSSLRSEDTAVYYCARSRTGNYWGQGTTVTS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APEAAGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 41 |
| 277-64 (Light Chain, IgG1) | DIVMTQSPDSLAVSLGERATISCKSSQSLLYSSNQKNY LAWYQQKPGQPPKLLIYWASTRESGVPDRFSGSGSGTD FTLTISSLQAEDVAVYYCQQYYSYPYTFGQGTKLEIKR TVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC | 42 |
| 277-64 (Heavy Chain, IgG1) | QVQLVQSGAEVKKPGASVKVSCKASGYTFTGYWMHWVR QAPGQGLEWIGYINPSTDYTEYNQKFKDRVTMTRDTST STVYMELSSLRSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 43 |
| 277-64 (Heavy Chain, IgG1-KO) | QVQLVQSGAEVKKPGASVKVSCKASGYTFTGYWMHWVR QAPGQGLEWIGYINPSTDYTEYNQKFKDRVTMTRDTST STVYMELSSLRSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APEAAGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 44 |
| 277-67 (Light Chain, IgG1) | DIVMTQSPDSLAVSLGERATINCKSSQSLLYSSNQKNY LAWYQQKPGQSPKLLIYWASTRESGVPDRFSGSGSGTD FTLTISSLQAEDVAVYYCQQYYSYPYTFGQGTKLEIKR TVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC | 45 |
| 277-67 (Heavy Chain, IgG1) | QVQLVQSGAEVKKPGASVKVSCKASGYTFTGYWMHWVR QAPGQGLEWIGYINPSTDYTEYNQKFKDRVTMTRDTST STVYMELSSLRSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APELLGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | 46 |
| 277-67 (Heavy Chain, IgG1-KO) | QVQLVQSGAEVKKPGASVKVSCKASGYTFTGYWMHWVR QAPGQGLEWIGYINPSTDYTEYNQKFKDRVTMTRDTST STVYMELSSLRSEDTAVYYCARSRTGNYWGQGTTVTVS SASTKGPSVFPLAPSSKSTSGGTAALGCLVKDYFPEPV TVSWNSGALTSGVHTFPAVLQSSGLYSLSSVVTVPSSS LGTQTYICNVNHKPSNTKVDKRVEPKSCDKTHTCPPCP APEAAGGPSVFLFPPKPKDTLMISRTPEVTCVVVDVSH EDPEVKFNWYVDGVEVHNAKTKPREEQYNSTYRVVSVL | 47 |

TABLE 1-continued

| Antibody | Sequence | SEQ ID NO: |
|---|---|---|
| | TVLHQDWLNGKEYKCKVSNKALPAPIEKTISKAKGQPR EPQVYTLPPSREEMTKNQVSLTCLVKGFYPSDIAVEWE SNGQPENNYKTTPPVLDSDGSFFLYSKLTVDKSRWQQG NVFSCSVMHEALHNHYTQKSLSLSPG | |
| 277 L-CDR1 | *KSSQSLLYSSNQKNYLA* | 48 |
| 277 L-CDR2 | *WASTRES* | 49 |
| 277 L-CDR3 | *QQYYSYPYT* | 50 |
| 277 H-CDR1 (CCG) | GYTFTGYWMH | 51 |
| 277 H-CDR2 (CCG) | YINPSTDYTEYNQKFKD | 52 |
| 277 H-CDR3 (CCG) | SRTGNY | 53 |
| 277 H-CDR1 (Kabat) | GYWMH | 55 |
| 277 H-CDR2 (Kabat) | YINPSTDYTEYNQKFKD | 56 |
| 277 H-CDR3 (Kabat) | SRTGNY | 57 |
| 277 H-CDR1 (Chothia) | *GYTFTGY* | 58 |
| 277 H-CDR2 (Chothia) | *NPSTDY* | 59 |
| 277 H-CDR3 (Chothia) | *SRTGNY* | 60 |

Above CDRs as per the Chemical Computing Group (CCG) numbering are underlined (Almagro et al., Proteins 2011; 79:3050-3066 and Maier et al, Proteins 2014; 82:1599-1610). The Kabat numbering for the sequences is denoted by the bold text and the Chothia numbering system by the italicized text.

In one aspect, an anti-TrkB antibody of the present invention binds to human TrkB at a $K_D<10$ nM. In a further aspect, an anti-TrkB antibody of the present invention binds to human TrkB at a $K_D<5$ nM. In yet a further aspect, an anti-TrkB antibody of the present invention binds to human TrkB at a $K_D$ of about 1 nM. Binding affinities of anti-TrkB antibodies can be determined according to the method described in example 6.

In another aspect, an anti-TrkB antibody of the present invention induces TrkB phosphorylation and/or activation with high potency. In one aspect, an anti-TrkB antibody of the present invention phosphorylates human TrkB with an $EC_{50}<100$ pM. In a further aspect, an anti-TrkB antibody of the present invention phosphorylates human TrkB with an $EC_{50}<50$ pM. In a further aspect, an anti-TrkB antibody of the present invention phosphorylates human TrkB with an $EC_{50}<40$ pM. In a further aspect, an anti-TrkB antibody of the present invention phosphorylates human TrkB with an $EC_{50}<30$ pM. In a further aspect, an anti-TrkB antibody of the present invention phosphorylates human TrkB with an $EC_{50}$ of about 20 pM.

In another aspect, an anti-TrkB antibody of the present invention is more potent in inducing activation of TrkB downstream signaling pathways than the natural TrkB ligand BDNF. Potency of anti-TrkB antibodies can be determined in differentiated SH-SY5Y cells according to the method described in example 8.

In a further aspect, an anti-TrkB antibody of the present invention induces a gene expression comparably to the natural TrkB ligand BDNF. Stimulation with agonistic anti-TrkB antibodies increases the mRNA expression of ARC, VGF, EGR1 which are markers for increased synaptic plasticity and therefore indicators that anti-TrkB antibodies act like the natural ligand BDNF in modulating neuronal function, i.e. the increase of neuronal survival and/or synaptic plasticity. Gene expression patterns can be determined according to the method described in example 10.

In yet a further aspect an anti-TrkB antibody of the present invention protects neurons, glial cells and/or the neurovascular unit in the retina of patients with e.g. age-related macular degeneration, geographic atrophy or diabetic retinopathy by stimulating TrkB-dependent survival signaling pathways and thereby providing neuroprotection.

In another aspect an anti-TrkB antibody of the present invention regenerates axons/dendrites and/or synapses in the retina after disease onset in e.g. age-related macular degeneration, geographic atrophy or diabetic retinopathy and thereby resulting in neuroregeneration.

In a further aspect, an anti-TrkB antibody of the present invention has a low immunogenicity risk and low sequence liabilities with respect to its CDR sequences. Immunogenicity and heterogeneity are two important aspects of a therapeutic antibody. Measurement of such aspects can be done by the methods as described in examples 4 and 5. The antibodies of the present invention have been carefully engineered to have a minimum or no immunogenicity and/or heterogeneity.

In yet another aspect, an anti-TrkB antibody of the present invention does not reduce BDNF induced ERK phosphorylation. For this purpose, ERK phosphorylation can be measured e.g. in CHO cells expressing human TrkB as described in Example 13. This could mean that the ERK phosphorylation induced by endogenously expressed BDNF is not reduced when the anti-TrkB antibody of the invention is administered. It could also mean that the anti-TrkB antibody of the invention does not reduce ERK phosphorylation when administered prior, concurrently or subsequently after exogenously administered BDNF. In some instances, an anti-TrkB antibody does not compete with or lower BDNF induced ERK phosphorylation compared to BDNF induction alone.

In a further aspect, an anti-TrkB antibody of the present invention is specific for TrkB phosphorylation and/or activation and does not unspecifically phosphorylate and/or activate TrkA or TrkC.

In another aspect, an anti-TrkB antibody does not bind unspecifically to human VEGF and/or rat VEGF. Binding unspecifically in this context means that the inventive anti-TrkB antibody does not bind to human VEGF, as measured e.g. in an ELISA as described in Example 14. In one embodiment, the lack of unspecific binding of an anti-TrkB antibody can be determined by measuring a statistically significant difference (e.g. unpaired t-test, p<0.05) in binding to human VEGF between an anti-TrkB antibody and an appropriate IgG isotype control antibody. In particular, the lack of unspecific binding of the inventive anti-TrkB antibody can be measured by determining any differences in binding to human VEGF between an anti-TrkB antibody and an IgG1 isotype control antibody. An inventive anti-TrkB antibody will not differ significantly in lack of binding to human VEGF compared to an equally concentrated IgG1 isotype control antibody up to a concentration of about 0.3 nM, 0.4 nM, 0.5 nM, 0.6 nM, 0.7 nM, 0.8 nM, 0.9 nM, 1 nM, 5 nM, 10 nM, 20 nM, 30 nM, 40 nM, 50 nM, 60 nM, 70 nM, 80 nM, 90 nM, 100 nM, 110 nM, 120 nM, 130 nM, 140 nM, 150 nM, 160 nM, 170 nM, 180 nM, 190 nM or 200 nM. In an alternative embodiment the lack of unspecific binding of the inventive anti-TrkB antibody can be measured by determining the $IC_{50}$ binding value of the anti-TrkB antibody to either one of human or rat VEGF. In particular, an inventive anti-TrkB antibody will exhibit an $IC_{50}$ binding-value to human or rat VEGF of about above 0.9 µM, preferably above 1 µM, above 2 µM, above 30, above 50, above 10 µM, above 20 µM, above 30 µM, above 40 µM, above 50 µM, above 100 µM, above 150 µM, above 200 µM, above 250 µM, above 300 µM, above 350 µM, above 400 µM, above 450 µM, above 500 µM, above 550 µM, above 600 µM, above 650 µM, above 700 µM, above 750 µM, above 800 µM, above 850 µM, or above 900 µM.

Humanization and Amino Acid Sequence Variants

Further variant anti-TrkB antibodies and antibody fragments can be engineered based on the set of CDRs identified in the murine lead D003. It is to be understood that in said variant anti-TrkB antibodies and antibody fragments the amino acid sequence of the CDRs remain unchanged but the surrounding regions e.g. FR regions can be engineered. Amino acid sequence variants of the anti-TrkB antibody can be prepared by introducing appropriate nucleotide changes into the anti-TrkB antibody DNA, or by peptide synthesis. Such variants include, for example, deletions from, and/or insertions into and/or substitutions of, residues within the amino acid sequences of the anti-TrkB antibodies of the examples herein. Any combination of deletions, insertions, and substitutions is made to arrive at the final construct, provided that the final construct possesses the desired characteristics. The amino acid changes also may alter post-translational processes of the humanized or variant anti-TrkB antibody, such as changing the number or position of glycosylation sites.

In some embodiments, the present invention includes anti-TrkB antibodies or antibody fragments thereof having a variable light chain and a variable heavy chain, wherein the variable light chain amino acid sequence and the variable heavy chain amino acid sequence are at least 80%, at least 90%, at least 95%, at least 98%, or at least 99% identical to the amino acid sequences of SEQ ID NO: 2 and 12, or 3 and 13, or 4 and 14, or 5 and 15, or 6 and 16, or 7 and 17, or 8 and 18, or 9 and 19, or 10 and 20, respectively.

In some embodiments, the present invention includes anti-TrkB antibodies or antibody fragments thereof having a light chain and a heavy chain, wherein the light chain amino acid sequence and the heavy chain amino acid sequence are at least 80%, at least 90%, at least 95%, at least 98%, or at least 99% identical to the amino acid sequences of SEQ ID NO: 21 and 22 or 23; 24 and 25 or 26; 27 and 28 or 29; 30 and 31 or 32; 33 and 34 or 35; 36 and 37 or 38; 39 and 40 or 41; 42 and 43 or 44; 45 and 46 or 47, respectively.

In a further embodiment, the present invention includes anti-TrkB antibodies that compete for binding to TrkB with any one of the following antibodies:

An antibody having a light chain comprising the amino acid sequence of SEQ ID NO: 21 and a heavy chain comprising the amino acid sequence of SEQ ID NO: 22 or 23, An antibody having a light chain comprising the amino acid sequence of SEQ ID NO: 24 and a heavy chain comprising the amino acid sequence of SEQ ID NO: 25 or 26, An antibody having a light chain comprising the amino acid sequence of SEQ ID NO: 27 and a heavy chain comprising the amino acid sequence of SEQ ID NO: 28 or 29, An antibody having a light chain comprising the amino acid sequence of SEQ ID NO: 30 and a heavy chain comprising the amino acid sequence of SEQ ID NO: 31 or 32, An antibody having a light chain comprising the amino acid sequence of SEQ ID NO: 33 and a heavy chain comprising the amino acid sequence of SEQ ID NO: 34 or 35, An antibody having a light chain comprising the amino acid sequence of SEQ ID NO: 36 and a heavy chain comprising the amino acid sequence of SEQ ID NO: 37 or 38, An antibody having a light chain comprising the amino acid sequence of SEQ ID NO: 39 and a heavy chain comprising the amino acid sequence of SEQ ID NO: 40 or 41, An antibody having a light chain comprising the amino acid sequence of SEQ ID NO: 42 and a heavy chain comprising the amino acid sequence of SEQ ID NO: 43 or 44, or An antibody having a light chain comprising the amino acid sequence of SEQ ID NO: 45 and a heavy chain comprising the amino acid sequence of SEQ ID NO: 46 or 47.

Another type of amino acid variant of the antibody involves altering the original glycosylation pattern of the antibody. The term "altering" in this context means deleting one or more carbohydrate moieties found in the antibody, and/or adding one or more glycosylation sites that were not previously present in the antibody.

In some aspects, the present invention includes nucleic acid molecules that encode the amino acid sequence variants of the anti-TrkB antibodies described herein. Nucleic acid molecules encoding amino acid sequence variants of the anti-TrkB antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-TrkB antibody.

In certain embodiments, the anti-TrkB antibody is an antibody fragment. There are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from E. coli and chemically coupled to form F(ab')₂ fragments (see, e.g., Carter et al., 1992, Bio/Technology 10:163-167). By another approach, F(ab')₂ fragments can be isolated directly from recombinant host cell culture. Other techniques for the production of antibody fragments will be apparent to the skilled practitioner.

The anti-TrkB antibodies and antigen-binding fragments thereof can include modifications.

In certain embodiments, it may be desirable to use an anti-TrkB antibody fragment, rather than an intact antibody. It may be desirable to modify the antibody fragment in order to increase its serum half life. This can be achieved, for example, by incorporation of a salvage receptor binding epitope into the antibody fragment. In one method, the appropriate region of the antibody fragment can be altered (e.g., mutated), or the epitope can be incorporated into a peptide tag that is then fused to the antibody fragment at either end or in the middle, for example, by DNA or peptide synthesis. See, e.g., WO 96/32478.

In other embodiments, the present invention includes covalent modifications of the anti-TrkB antibodies. Covalent modifications include modification of cysteinyl residues, histidyl residues, lysinyl and amino-terminal residues, arginyl residues, tyrosyl residues, carboxyl side groups (aspartyl or glutamyl), glutaminyl and asparaginyl residues, or seryl, or threonyl residues. Another type of covalent modification involves chemically or enzymatically coupling glycosides to the antibody. Such modifications may be made by chemical synthesis or by enzymatic or chemical cleavage of the antibody, if applicable. Other types of covalent modifications of the antibody can be introduced into the molecule by reacting targeted amino acid residues of the antibody with an organic derivatizing agent that is capable of reacting with selected side chains or the amino- or carboxy-terminal residues.

Removal of any carbohydrate moieties present on the antibody can be accomplished chemically or enzymatically. Chemical deglycosylation is described by Hakimuddin et al., 1987, Arch. Biochem. Biophys. 259:52 and by Edge et al., 1981, Anal. Biochem., 118:131. Enzymatic cleavage of carbohydrate moieties on antibodies can be achieved by the use of a variety of endo- and exo-glycosidases as described by Thotakura et al., 1987, Meth. Enzymol 138:350.

Another type of useful covalent modification comprises linking the antibody to one of a variety of nonproteinaceous polymers, e.g., polyethylene glycol, polypropylene glycol, or polyoxyalkylenes, in the manner set forth in one or more of U.S. Pat. Nos. 4,640,835, 4,496,689, 4,301,144, 4,670, 417, 4,791,192 and 4,179,337.

Epitope Binding

The antibodies of the invention specifically bind to native or recombinant human TrkB. The antibodies of the present invention recognize specific "TrkB antigen epitope" and "TrkB epitope". In particular, the antibodies of the invention bind to an epitope in the extracellular domain of human TrkB with the SEQ ID NO: 54.

The extracellular domain of human TrkB essentially comprises the following sequence (SEQ ID NO.54):

CPTSCKCSASRIWCSDPSPGIVAFPRLEPNSVDPENITEIFIANQKRL
EIINEDDVEAYVGLRNLTIVDSGLKFVAHKAFLKNSNLQHINFTRNKL
TSLSRKHFRHLDLSELILVGNPFTCSCDIMWIKTLQEAKSSPDTQDLY
CLNESSKNIPLANLQIPNCGLPSANLAAPNLTVEEGKSITLSCSVAGD
PVPNMYWDVGNLVSKHMNETSHTQGSLRITNISSDDSGKQISCVAENL
VGEDQDSVNLTVHFAPTITFLESPTSDHHWCIPFTVKGNPKPALQWFY
NGAILNESKYICTKIHVTNHTEYHGCLQLDNPTHMNNGDYTLIAKNEY
GKDEKQISAHFMGWPGIDDGANPNYPDVIYEDYGTAANDIGDTTNRSN
EIPSTDVTDKTGREH

As used herein, the terms "TrkB antigen epitope" and "TrkB epitope" refer to a molecule (e.g., a peptide) or a fragment of a molecule capable of binding to an anti-TrkB antibody or antigen-binding fragment thereof. These terms further include, for example, a TrkB antigenic determinant recognized by any of the antibodies or antibody fragments of the present invention, which has a light and heavy chain CDR combination selected from light chain CDRs of the SEQ ID NOs 48 to 50 and heavy chain CDRs of the SEQ ID NOs: 51 to 53.

TrkB antigen epitopes can be included in proteins, protein fragments, peptides or the like. The epitopes are most commonly proteins, short oligopeptides, oligopeptide mimics (i.e., organic compounds that mimic antibody binding properties of the TrkB antigen), or combinations thereof.

It has been found that the antibodies or antibody fragments of the present invention bind to unique epitopes in the extracellular domain of human TrkB. Preferably, an anti-TrkB antibody or antigen-binding fragment thereof binds to at least one amino acid residue within amino acid regions 92-112, 130-143 and/or 205-219 of the extracellular domain of human TrkB with the SEQ ID NO: 54.

In one embodiment, the present invention provides an anti-TrkB antibody or antigen-binding fragment thereof that binds to at least one amino acid residue within amino acid regions 92-112 and 130-143; or 92-112 and 205-219; or 130-143 and 205-219; or 92-112 and 130-143 and 205-219 of the extracellular domain of human TrkB with the SEQ ID NO: 54.

In one embodiment, the present invention provides an anti-TrkB antibody or antigen-binding fragment thereof that binds to at least one amino acid residue within any of the aforementioned combinations of amino acid regions and further also to at least one amino acid residue within amino acid regions 313-330 and/or 348-367 of the extracellular domain of human TrkB with the SEQ ID NO: 54.

In one embodiment, the present invention provides an anti-TrkB antibody or antigen-binding fragment thereof that binds to at least one amino acid residue within amino acid regions 92-112, 130-143, 205-219, 313-330 and 348-367 of the extracellular domain of human TrkB with the SEQ ID NO: 54.

Thus, in the context of epitope binding, the phrase "binds within amino acid regions X-Y . . ." means that the anti-TrkB antibody or antigen-binding fragment thereof binds to at least one amino acid residue within the amino acid region specified in the sequence.

If for example, the anti-TrkB antibody or antigen-binding fragment thereof binds to at least one amino acid residue within amino acid regions 92-112 or 130-143, this has the meaning that the anti-TrkB antibody or antigen-binding fragment thereof binds to at least one amino acid residue either within amino acid regions 92-112 or 130-143.

In a further example, if the anti-TrkB antibody or antigen-binding fragment thereof binds to at least one amino acid residue within amino acid regions 92-112 and 130-143, this has the meaning that the anti-TrkB antibody or antigen-binding fragment thereof binds to at least one amino acid residue within amino acid region 92-112 and also binds to at least one amino acid residue within amino acid region 130-143 of SEQ ID NO: 54.

In another aspect, an anti-TrkB antibody or antigen-binding fragment thereof binds to at least 10%, 20%, 30%, 40%, 50%, 60%, 70%, 80%, 85%, 90%, 95%, or 100% of the amino acid residues within amino acid regions 92-112, 130-143 and/or 205-219 of the extracellular domain of human TrkB with the SEQ ID NO: 54.

In one embodiment, the present invention provides an anti-TrkB antibody or antigen-binding fragment thereof that binds to at least 10%, 20%, 30%, 40%, 50%, 60%, 70%, 80%, 85%, 90%, 95%, or 100% of the amino acid residues within amino acid regions 92-112 and 130-143; or 92-112 and 205-219; or 130-143 and 205-219; or 92-112 and 130-143 and 205-219 of the extracellular domain of human TrkB with the SEQ ID NO: 54.

In one embodiment, the present invention provides an anti-TrkB antibody or antigen-binding fragment thereof that binds to at least 10%, 20%, 30%, 40%, 50%, 60%, 70%, 80%, 85%, 90%, 95%, or 100% of the amino acid residues within any of the aforementioned combinations of amino acid regions and further also to at least 10%, 20%, 30%, 40%, 50%, 60%, 70%, 80%, 85%, 90%, 95%, or 100% of the amino acid residues within amino acid regions 313-330 and/or 348-367 of the extracellular domain of human TrkB with the SEQ ID NO: 54.

In one embodiment, the present invention provides an anti-TrkB antibody or antigen-binding fragment thereof that binds to at least 10%, 20%, 30%, 40%, 50%, 60%, 70%, 80%, 85%, 90%, 95%, or 100% of the amino acid residues within amino acid regions 92-112, 130-143, 205-219, 313-330 and 348-367 of the extracellular domain of human TrkB with the SEQ ID NO: 54.

If for example, the anti-TrkB antibody or antigen-binding fragment thereof binds to at least 10%, 20%, 30%, 40%, 50%, 60%, 70%, 80%, 85%, 90%, 95%, or 100% amino acid residues within amino acid regions 92-112 or 130-143, this has the meaning that the anti-TrkB antibody or antigen-binding fragment thereof binds to at least 10%, 20%, 30%, 40%, 50%, 60%, 70%, 80%, 85%, 90%, 95%, or 100% of the amino acid residues within amino acid region 92-112 or binds to at least 10%, 20%, 30%, 40%, 50%, 60%, 70%, 80%, 85%, 90%, 95%, or 100% of the amino acid residues within amino acid region 130-143.

In a further example, if the anti-TrkB antibody or antigen-binding fragment thereof binds to at least 10%, 20%, 30%, 40%, 50%, 60%, 70%, 80%, 85%, 90%, 95%, or 100% amino acid residues within amino acid regions 92-112 and 130-143, this has the meaning that the anti-TrkB antibody or antigen-binding fragment thereof binds to at least 10%, 20%, 30%, 40%, 50%, 60%, 70%, 80%, 85%, 90%, 95%, or 100% of the amino acid residues within amino acid region 92-112 and also binds to at least 10%, 20%, 30%, 40%, 50%, 60%, 70%, 80%, 85%, 90%, 95%, or 100% amino acid residues within amino acid region 130-143.

Without wishing to be bound by any theory, it is believed that due to the binding to the novel epitopes the TrkB antibody exerts its superior effects in activating TrkB.

Polynucleotides, Vectors, Host Cells, and Recombinant Methods

Other embodiments encompass isolated polynucleotides that comprise a sequence encoding an anti-TrkB antibody, vectors, and host cells comprising the polynucleotides, and recombinant techniques for production of the antibody. The isolated polynucleotides can encode any desired form of the anti-TrkB antibody including, for example, full length monoclonal antibodies, Fab, Fab', F(ab')$_2$, and Fv fragments, diabodies, linear antibodies, single-chain antibody molecules, and multispecific antibodies formed from antibody fragments.

The polynucleotide(s) that comprise a sequence encoding an anti-TrkB antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The anti-TrkB antibodies can also be produced as fusion polypeptides, in which the antibody is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the anti-TrkB antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO90/13646.

In mammalian cells, mammalian signal sequences as well as viral secretory leaders, for example, the herpes simplex gD signal, can be used. The DNA for such precursor region is ligated in reading frame to DNA encoding the humanized anti-TrkB antibody.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-D. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin. Common selectable markers for mammalian cells are those that enable the identification of cells competent to take up a nucleic acid encoding a humanized anti-TrkB antibody, such as DHFR (dihydrofolate reductase), thymidine kinase, metallothionein-I and -II (such as primate metallothionein genes), adenosine deaminase, ornithine decarboxylase, and the like. Cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., DG44).

Alternatively, host cells (particularly wild-type hosts that contain endogenous DHFR) transformed or co-transformed with DNA sequences encoding anti-TrkB antibody, wild-type DHFR protein, and another selectable marker such as aminoglycoside 3'-phosphotransferase (APH), can be selected by cell growth in medium containing a selection agent for the selectable marker such as an aminoglycosidic antibiotic, e.g., kanamycin, neomycin, or G418. See, e.g., U.S. Pat. No. 4,965,199.

Where the recombinant production is performed in a yeast cell as a host cell, the TRP1 gene present in the yeast plasmid YRp7 (Stinchcomb et al., 1979, Nature 282: 39) can be used as a selectable marker. The TRP1 gene provides a selection marker for a mutant strain of yeast lacking the ability to grow in tryptophan, for example, ATCC No. 44076 or PEP4-1 (Jones, 1977, Genetics 85:12). The presence of the trp1 lesion in the yeast host cell genome then provides an effective environment for detecting transformation by growth in the absence of tryptophan. Similarly, Leu2p-deficient yeast strains such as ATCC 20,622 and 38,626 are complemented by known plasmids bearing the LEU2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis* (Van den Berg, 1990, Bio/Technology 8:135). Stable multi-copy expression vectors for secretion of mature recombinant human serum albumin by industrial strains of *Kluyveromyces* have also been disclosed (Fleer et al., 1991, Bio/Technology 9:968-975).

Expression and cloning vectors usually contain a promoter that is recognized by the host organism and is operably linked to the nucleic acid molecule encoding an anti-TrkB antibody or polypeptide chain thereof. Promoters suitable for use with prokaryotic hosts include phoA promoter, β-lactamase and lactose promoter systems, alkaline phosphatase, tryptophan (trp) promoter system, and hybrid promoters such as the tac promoter. Other known bacterial promoters are also suitable. Promoters for use in bacterial systems also will contain a Shine-Dalgarno (S.D.) sequence operably linked to the DNA encoding the humanized anti-TrkB antibody.

Many eukaryotic promoter sequences are known. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Inducible promoters have the additional advantage of transcription controlled by growth conditions. These include yeast promoter regions for alcohol dehydrogenase 2, isocytochrome C, acid phosphatase, derivative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-TrkB antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., 1982, Nature 297:598-601, disclosing expression of human p-interferon cDNA in mouse cells under the control of a thymidine kinase promoter from herpes simplex virus. Alternatively, the rous sarcoma virus long terminal repeat can be used as the promoter.

Another useful element that can be used in a recombinant expression vector is an enhancer sequence, which is used to increase the transcription of a DNA encoding an anti-TrkB antibody by higher eukaryotes. Many enhancer sequences are now known from mammalian genes (e.g., globin, elastase, albumin, α-fetoprotein, and insulin). Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, Nature 297:17-18 for a description of enhancing elements for activation of eukaryotic promoters. The enhancer may be spliced into the vector at a position 5' or 3' to the anti-TrkB antibody-encoding sequence, but is preferably located at a site 5' from the promoter.

Expression vectors used in eukaryotic host cells (yeast, fingi, insect, plant, animal, human, or nucleated cells from other multicellular organisms) can also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-TrkB antibody. One useful transcription termination component is the bovine growth hormone polyadenylation region. See WO94/11026 and the expression vector disclosed therein. In some embodiments, anti-TrkB antibodies can be expressed using the CHEF system. (See, e.g., U.S. Pat. No. 5,888,809; the disclosure of which is incorporated by reference herein.)

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-TrkB antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosopharum* (ATCC 36,906), *K. thermotolerans*, and *K. marxianus; yarrowia* (EP 402,226); *Pichia pastors* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger*.

Suitable host cells for the expression of glycosylated anti-TrkB antibody are derived from multicellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, *petunia*, tomato, and tobacco can also be utilized as hosts.

The inventive anti-TrkB antibodies or antigen-binding fragments thereof can also be incorporated in viral vectors, i.e. the polynucleotide encoding for the anti-TrkB antibody or antigen-binding fragment thereof is introduced into the viral vector and then expressed in the body of the patient after infection with the virus.

In another aspect, expression of anti-TrkB is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36: 59), baby hamster kidney cells (BHK, ATCC CCL 10), Chinese hamster ovary cells/–DHFR1 (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383: 44-68), MRC 5 cells, FS4 cells, and human hepatoma line (Hep G2).

Host cells are transformed with the above-described expression or cloning vectors for anti-TrkB antibody production and cultured in conventional nutrient media modified as appropriate for inducing promoters, selecting transformants, or amplifying the genes encoding the desired sequences.

The host cells used to produce anti-TrkB antibody described herein may be cultured in a variety of media. Commercially available media such as Ham's F10 (Sigma-Aldrich Co., St. Louis, Mo.), Minimal Essential Medium ((MEM), (Sigma-Aldrich Co.), RPMI-1640 (Sigma-Aldrich Co.), and Dulbecco's Modified Eagle's Medium ((DMEM), Sigma-Aldrich Co.) are suitable for culturing the host cells. In addition, any of the media described in one or more of Ham et al., 1979, Meth. Enz. 58: 44, Barnes et al., 1980, Anal. Biochem. 102: 255, U.S. Pat. Nos. 4,767,704, 4,657, 866, 4,927,762, 4,560,655, 5,122,469, WO 90/103430, and WO 87/00195 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, the cells may be disrupted to release protein as a first step. Particulate debris, either host cells or lysed fragments, can be removed, for example, by centrifugation or ultrafiltration. Carter et al., 1992, Bio/Technology 10:163-167 describes a procedure for isolating antibodies that are secreted to the periplasmic space of E. coli. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. A variety of methods can be used to isolate the antibody from the host cell.

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 J. Immunol. Meth. 62:1-13). Protein G is recommended for all mouse isotypes and for human gamma3 (see, e.g., Guss et al., 1986 EMBO J. 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25M salt).

Also included are nucleic acids that hybridize under low, moderate, and high stringency conditions, as defined herein, to all or a portion (e.g., the portion encoding the variable region) of the nucleotide sequence represented by isolated polynucleotide sequence(s) that encode an TrkB-antibody or antibody fragment. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-TrkB polypeptide (e.g., a heavy chain or light chain variable region), or its complement. Hybridizing nucleic acids of the type described herein can be used, for example, as a cloning probe, a primer, e.g., a PCR primer, or a diagnostic probe.

In some embodiments, the present invention includes isolated polynucleotide(s) including sequences that encode an antibody or antibody fragment having a variable light chain and a variable heavy chain, wherein the variable light chain amino acid sequence and the variable heavy chain amino acid sequence are at least 80%, at least 90%, at least 95%, at least 98%, or at least 99% identical to the amino acid sequences of SEQ ID NO: 2 and 12, or 3 and 13, or 4 and 14, or 5 and 15, or 6 and 16, or 7 and 17, or 8 and 18, or 9 and 19, or 10 and 20, respectively.

In some embodiments, the present invention includes isolated polynucleotide(s) including sequences that encode an antibody or antibody fragment having a light chain and a heavy chain, wherein the light chain amino acid sequence and the heavy chain amino acid sequence are at least 80%, at least 90%, at least 95%, at least 98%, or at least 99% identical to the amino acid sequences of SEQ ID NO: 21 and 22 or 23; 24 and 25 or 26; 27 and 28 or 29; 30 and 31 or 32; 33 and 34 or 35; 36 and 37 or 38; 39 and 40 or 41; 42 and 43 or 44; 45 and 46 or 47, respectively.

It is to be understood that in said anti-TrkB antibodies and antibody fragments the nucleic acid sequence coding for the CDRs remain unchanged (unchanged with respect to the amino acid they encode, equivalents of the DNA sequence due to the degeneracy of codons are possible) but the surrounding regions e.g. FR regions can be engineered.

Non-Therapeutic Uses

The antibodies described herein are useful as affinity purification agents. In this process, the antibodies are immobilized on a solid phase such a Protein A resin, using methods well known in the art. The immobilized antibody is contacted with a sample containing the TrkB protein (or fragment thereof) to be purified, and thereafter the support is washed with a suitable solvent that will remove substantially all the material in the sample except the TrkB protein, which is bound to the immobilized antibody. Finally, the support is washed with another suitable solvent that will release the TrkB protein from the antibody.

Anti-TrkB antibodies are also useful in diagnostic assays to detect and/or quantify TrkB protein, for example, detecting TrkB expression in specific cells, tissues, or serum.

It will be advantageous in some embodiments, for example, for diagnostic purposes to label the antibody with a detectable moiety. Numerous detectable labels are available, including radioisotopes, fluorescent labels, enzyme substrate labels and the like. The label may be indirectly conjugated with the antibody using various known techniques. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody can be conjugated with a small hapten (such as digoxin) and one of the different types of labels mentioned above is conjugated with an anti-hapten antibody (e.g., anti-digoxin antibody). Thus, indirect conjugation of the label with the antibody can be achieved.

Exemplary radioisotopes labels include $^{35}S$, $^{14}C$, $^{125}I$, $^{3}H$, and $^{131}I$. The antibody can be labeled with the radioisotope, using the techniques described in, for example, Current Protocols in Immunology, Volumes 1 and 2, 1991, Coligen et al., Ed. Wiley-Interscience, New York, N.Y., Pubs. Radioactivity can be measured, for example, by scintillation counting.

Exemplary fluorescent labels include labels derived from rare earth chelates (europium chelates) or fluorescein and its derivatives, rhodamine and its derivatives, dansyl, Lissamine, phycoerythrin, and Texas Red are available. The fluorescent labels can be conjugated to the antibody via known techniques, such as those disclosed in Current Protocols in Immunology, supra, for example. Fluorescence can be quantified using a fluorimeter.

There are various well-characterized enzyme-substrate labels known in the art (see, e.g., U.S. Pat. No. 4,275,149 for a review). The enzyme generally catalyzes a chemical alteration of the chromogenic substrate that can be measured using various techniques. For example, alteration may be a color change in a substrate that can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured, using a chemiluminometer, for example, or donates energy to a fluorescent acceptor.

Examples of enzymatic labels include luciferases such as firefly luciferase and bacterial luciferase (U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (such as glucose oxidase, galactose oxidase, and glucose-6-phosphate dehydrogenase), heterocydic oxidases (such as uricase and xanthine oxidase), lactoperoxidase, microperoxidase, and the like. Techniques for conjugating enzymes to antibodies are described, for example, in O'Sullivan et al., 1981, Methods for the Preparation of Enzyme-Antibody Conjugates for use in Enzyme Immunoassay, in Methods in Enzym. (J. Langone & H. Van Vunakis, eds.), Academic press, N.Y., 73: 147-166.

Examples of enzyme-substrate combinations include, for example: Horseradish peroxidase (HRPO) with hydrogen peroxidase as a substrate, wherein the hydrogen peroxidase oxidizes a dye precursor such as orthophenylene diamine (OPD) or 3,3',5,5'-tetramethyl benzidine hydrochloride (TMB); alkaline phosphatase (AP) with para-Nitrophenyl phosphate as chromogenic substrate; and β-D-galactosidase (β-D-Gal) with a chromogenic substrate such as p-nitrophenyl-β-D-galactosidase or fluorogenic substrate 4-methyl-umbelliferyl-β-D-galactosidase.

Numerous other enzyme-substrate combinations are available to those skilled in the art. For a general review of these, see U.S. Pat. Nos. 4,275,149 and 4,318,980.

In another embodiment, the anti-TrkB antibody is used unlabeled and detected with a labeled antibody that binds the anti-TrkB antibody.

The antibodies described herein may be employed in any known assay method, such as competitive binding assays, direct and indirect sandwich assays, and immunoprecipitation assays. See, e.g., Zola, Monoclonal Antibodies: A Manual of Techniques, pp. 147-158 (CRC Press, Inc. 1987).

Diagnostic Kits

An anti-TrkB antibody can be used in a diagnostic kit, i.e., a packaged combination of reagents in predetermined amounts with instructions for performing the diagnostic assay. Where the antibody is labeled with an enzyme, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration.

Therapeutic Uses & TrkB-Associated Disorders

In another embodiment, an anti-TrkB antibody (or a functional fragment thereof) disclosed herein is useful in the treatment of various disorders associated with the expression of TrkB as described herein.

The anti-TrkB antibody or antigen-binding fragment thereof is administered by any suitable means, including intravitreal, oral, parenteral, subcutaneous, intraperitoneal, intrapulmonary, and intranasal. Parenteral infusions include intramuscular, intravenous, intraarterial, intraperitoneal, or subcutaneous administration. In addition, the anti-TrkB antibody is suitably administered by pulse infusion, particularly with declining doses of the antibody. In one aspect, the dosing is given by injections, most preferably intravenous or subcutaneous injections, depending in part on whether the administration is brief or chronic. Preferably, the anti-TrkB antibody is given through an intravitreal injection into the eye.

For the prevention or treatment of disease, the appropriate dosage of antibody will depend on a variety of factors such as the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

The term "suppression" is used herein in the same context as "amelioration" and "alleviation" to mean a lessening or diminishing of one or more characteristics of the disease.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat the disorder associated with TrkB expression.

The antibody need not be, but is optionally, formulated with one or more agents currently used to prevent or treat the disorder in question. The effective amount of such other agents depends on the amount of anti-TrkB antibody present in the formulation, the type of disorder or treatment, and other factors discussed above. These are generally used in the same dosages and with administration routes as used hereinbefore or about from 1 to 99% of the heretofore employed dosages.

The agonistic anti-TrkB antibodies of the present invention stimulate TrkB signaling. Without wishing to be bound to theory it is believed that TrkB signaling is beneficial to protect photoreceptors, other retinal neurons including ganglion cells and retinal pigment epithelial cells from cell death in the retina. Therefore, agonistic anti-TrkB antibodies can protect retinal neurons such as photoreceptors from degeneration, i.e. prevent neuro-degeneration, and also increase neuronal survival and/or plasticity, ultimately counteracting vision loss associated with either reduced TrkB activity and/or increased cell stress or apoptotic activity. Thus, the antibodies are useful for treatment of diseases of the eye or retinal diseases, in particular neurodegenerative retinal or eye diseases. Such diseases comprise but are not limited to age-related macular degeneration, geographic atrophy, diabetic retinopathy, diabetic macular edema, retinitis pigmentosa, inherited retinal dystrophy, inherited macular dystrophy, myopic degeneration, retinal vein occlusions, retinal artery occlusions, endophthalmitis, uveitis, cystoid macular edema, choroidal neovascular membrane secondary to any retinal diseases, optic neuropathies, glaucoma, retinal detachment, toxic retinopathy, radiation retinopathy, and traumatic retinopathy.

The antibodies are furthermore useful for treatment of diseases of the central nervous system such as prodromal and mild-to-moderate alzheimer's diseases, delaying disease progression of patients with Alzheimer's disease, Huntington's disease, Parkinson's disease, major depressive disorder, schizophrenia, cognitive impairment associated with schizophrenia, prevention of first-episode psychosis in individuals with attenuated psychosis syndrome, prevention of relapse in patients with schizophrenia or treatment-resistant depression.

In another embodiment the antibodies may be useful for treatment of hearing loss, in particular for cis platin induced hearing loss as well as noise and age-related hearing loss.

In particular, the agonistic anti-TrkB antibodies of the present invention are indicated for treatment of non-proliferative and/or proliferative diabetic retinopathy and/or diabetic macular edema in addition to standard of care: Dysfunction of retinal neurons and neurodegeneration are one of the major pathological events in diabetic retinopathy and diabetic macular edema (at all stages of the disease) that ultimately cause vision loss and visual dysfunction. TrkB activation will counteract the loss and functional impairments of retinal neurons and thereby help to maintain normal vision, to reduce the loss of visual function during the disease and potentially help to regain visual function.

Furthermore, there is the potential use of TrkB activation as an add-on to anti-VEGF treatment which will greatly enhance the therapeutic benefits of the latter since anti-VEGF targets only vascular dysfunction in the eye but not the neuron/glial cells system; in addition, long-term anti-VEGF treatment might cause neurodegenerative side-effects. A TrkB activating approach as an add-on to anti-VEGF will reduce such neurodegenerative side-effects.

The anti-TrkB antibodies or antigen-binding fragments thereof are in particular useful for treating or preventing retinal disorders, such as diabetic retinopathy, diabetic macular edema, geographic atrophy and glaucoma.

In a further aspect, the anti-TrkB antibodies or antigen-binding fragments thereof are also useful for the treatment of metabolic diseases such as hyperphagia, obesity and metabolic syndrome.

In another aspect, TrkB-antibodies of the present invention can be used in a method for treating and/or preventing a TrkB-associated disorder, in particular geographic atrophy, comprising administering a therapeutically effective amount of an inventive TrkB-antibody to an individual suffering from geographic atrophy, thereby ameliorating one or more symptoms of geographic atrophy.

In yet a further aspect, agonistic TrkB-antibodies can be used in a method for treating and/or preventing geographic atrophy, comprising administering a therapeutically effective amount of an agonistic TrkB-antibody to an individual suffering from geographic atrophy, thereby ameliorating one or more symptoms of geographic atrophy.

Pharmaceutical Compositions and Administration Thereof

A composition comprising an anti-TrkB antibody or an antigen-binding fragment thereof can be administered to a subject having or at risk of having an eye or retinal disease. The invention further provides for the use of an anti-TrkB antibody or an antigen-binding fragment thereof in the manufacture of a medicament for prevention or treatment of a TrkB disease. The term "subject" as used herein means any mammalian patient to which an anti-TrkB antibody or an antigen-binding fragment thereof can be administered, including, e.g., humans and non-human mammals, such as primates, rodents, and dogs. Subjects specifically intended for treatment using the methods described herein include humans. The anti-TrkB antibody or an antigen-binding fragment thereof can be administered either alone or in combination with other compositions.

Preferred antibodies for use in such pharmaceutical compositions are those that comprise humanized antibody or antibody fragments having a variable light chain and a variable heavy chain amino acid sequence of SEQ ID NO: 2 and 12, or 3 and 13, or 4 and 14, or 5 and 15, or 6 and 16, or 7 and 17, or 8 and 18, or 9 and 19, or 10 and 20, respectively.

Also contemplated are antibodies for use in such pharmaceutical compositions that comprise humanized antibody or antibody fragments having a variable light chain and a variable heavy chain amino acid sequence at least 80%, at least 90%, at least 95%, at least 98%, or at least 99% identical to the amino acid sequence of SEQ ID NO: 2 and 12, or 3 and 13, or 4 and 14, or 5 and 15, or 6 and 16, or 7 and 17, or 8 and 18, or 9 and 19, or 10 and 20, respectively.

Further preferred antibodies for use in such pharmaceutical compositions are those that comprise humanized antibody or antibody fragments having a light chain and a heavy chain amino acid sequence of SEQ ID NO: 21 and 22 or 23; 24 and 25 or 26; 27 and 28 or 29; 30 and 31 or 32; 33 and 34 or 35; 36 and 37 or 38; 39 and 40 or 41; 42 and 43 or 44; 45 and 46 or 47, respectively.

Further preferred antibodies for use in such pharmaceutical compositions that comprise humanized antibody or antibody fragments having a light chain and a heavy chain amino acid sequence at least 80%, at least 90%, at least 95%, at least 98%, or at least 99% identical to the amino acid sequence of SEQ ID NO: 21 and 22 or 23; 24 and 25 or 26; 27 and 28 or 29; 30 and 31 or 32; 33 and 34 or 35; 36 and 37 or 38; 39 and 40 or 41; 42 and 43 or 44; 45 and 46 or 47, respectively.

It is to be understood that in said anti-TrkB antibodies and antibody fragments the amino acid sequence of the CDRs remain unchanged but the surrounding regions e.g. FR regions can be engineered.

Various delivery systems are known and can be used to administer the anti-TrkB antibody or an antigen-binding fragment thereof. Methods of introduction include but are not limited to intravitreal, eye drops, intradermal, intramuscular, intraperitoneal, intravenous, subcutaneous, intranasal, epidural, and oral routes. The anti-TrkB antibody or an antigen-binding fragment thereof can be administered, for example by infusion, bolus or injection, and can be administered together with other biologically active agents. Administration can be systemic or local. In preferred embodiments, the administration is by intravitreal injection. Formulations for such injections may be prepared in, for example, prefilled syringes.

An anti-TrkB antibody or an antigen-binding fragment thereof can be administered as pharmaceutical compositions comprising a therapeutically effective amount of the anti-TrkB antibody or an antigen-binding fragment thereof and one or more pharmaceutically compatible ingredients.

In typical embodiments, the pharmaceutical composition is formulated in accordance with routine procedures as a pharmaceutical composition adapted for intravenous or subcutaneous administration to human beings. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing an anti-TrkB antibody or an antigen-binding fragment thereof in lyophilized form and (b) a second container containing a pharmaceutically acceptable diluent (e.g., sterile water) for injection. The pharmaceutically acceptable diluent can be used for reconstitution or dilution of the lyophilized anti-TrkB antibody or antigen-binding fragment thereof. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the anti-TrkB antibody or antigen-binding fragment thereof that is effective in the treatment or prevention of a TrkB-related disorder can be determined by standard clinical techniques. In addition, in vitro assays may optionally be employed to help identify optimal dosage ranges. The precise dose to be employed in the formulation will also depend on the route of administration, and the stage of disorder, and should be decided according to the judgment of the practitioner and each patient's circumstances. Effective doses may be extrapolated from dose-response curves derived from in vitro or animal model test systems.

For example, toxicity and therapeutic efficacy of the anti-TrkB antibody or antigen-binding fragment thereof can be determined in cell cultures or experimental animals by standard pharmaceutical procedures for determining the $ED_{50}$ (the dose therapeutically effective in 50% of the population). An anti-TrkB antibody or antigen-binding fragment thereof that exhibits a large therapeutic index is preferred.

The data obtained from the cell culture assays and animal studies can be used in formulating a range of dosage for use in humans. The dosage of the anti-TrkB antibody or antigen-binding fragment thereof typically lies within a range of circulating concentrations that include the $ED_{50}$ with little or no toxicity. The dosage may vary within this range depending upon the dosage form employed and the route of administration utilized. For any anti-TrkB antibody or antigen-binding fragment thereof used in the method, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography, ELISA and the like.

For intravitreal injection of the TrkB-antibody generally longer intervals between treatments are preferred. Due to its improved potency the TrkB antibodies of the present invention can be administered in longer intervals.

In one embodiment the TrkB-antibody is administered every 6 weeks, preferably every 7 weeks, also preferred every 8 weeks, further preferred every 9 weeks, more preferred every 10 weeks, further preferred every 11 weeks, and more preferred every 12 weeks. In a further preferred embodiment the TrkB-antibody is administered once every 3 months.

In an embodiment, the TrkB-antibody is administered to subject in need thereof at an initial dose of 1-2000 mg. In another embodiment, optionally one or more subsequent doses are administered, each of which comprising 1-2000 mg of the TrkB-antibody.

Since the volume that can be administered to the eye is strictly limited it is very important that an anti-TrkB antibody can be formulated to high concentrations. Furthermore, potency of the anti-TrkB antibody is of great importance as a potent antibody can exert its effect at even lower doses and thereby prolong activity and also intervals between treatments.

Antibodies of the present invention can be formulated to very high doses which include, but are not limited to 20 mg/ml, 30 mg/ml, 40 mg/ml, 50 mg/ml, 60 mg/ml, 70 mg/ml, 80 mg/ml, 90 mg/ml, or 100 mg/ml.

A typical dosage that can be administered to a patient is about 3 mg/eye. Typical buffer components that can be used for such a formulation comprise e.g. Sodium Acetate, PS20, and Trehalose Dihydrate.

In one embodiment, the anti-TrkB antibody is formulated with 10 mM histidine buffer, 240 mM sucrose, 0.02 w/v % polysorbate 20 at pH 5.5 with a final protein concentration of 60 mg/mL.

In some embodiments, the pharmaceutical compositions comprising the anti-TrkB antibody or antigen-binding fragment thereof can further comprise a therapeutic agent, either conjugated or unconjugated to the binding agent. The anti-TrkB antibody or antigen-binding fragment thereof can be co-administered in combination with one or more therapeutic agents for the treatment or prevention of a TrkB-related disease. For example, combination therapy can include anti-VEGF, anti-PDGF, or anti-ANG2.

Such combination therapy administration can have an additive or synergistic effect on disease parameters (e.g., severity of a symptom, the number of symptoms, or frequency of relapse).

With respect to therapeutic regimens for combinatorial administration, in a specific embodiment, an anti-TrkB antibody or antigen-binding fragment thereof is administered concurrently with a therapeutic agent. In another specific embodiment, the therapeutic agent is administered prior or subsequent to administration of the anti-TrkB antibody or antigen-binding fragment thereof, by at least an hour and up to several months, for example at least an hour, five hours, 12 hours, a day, a week, a month, or three months, prior or subsequent to administration of the anti-TrkB antibody or antigen-binding fragment thereof.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the anti-TrkB antibody or the antigen-binding fragment thereof. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

The invention is further described in the following examples, which are not intended to limit the scope of the invention.

EXAMPLES

1. Antibody Generation (Immunization)

B-cells from mice through immunization campaign were subjected to screening using the in-house developed Single B-cell platform technology. Anti-TrkB binders were further narrowed down after testing for activity, efficacy and potency in TrkB in-vitro phosphorylation assay.

2. Production of Humanized Antibodies

The murine lead D003 was selected for further optimization. The murine lead had a variable light chain corresponding to SEQ ID NO: 1 and a variable heavy chain corresponding to SEQ ID NO: 11.

To sequence optimize the TrkB murine lead D003, the most similar human germ-line antibody sequences were selected, IGKV4-1*01, KJ2 for the light chain and IGHV1-46*03, HJ6 for the heavy chain. A library of variants was generated. This resulted in the humanized light chain variable sequences of SEQ ID NOs: 2-10 and heavy chain variable sequences of SEQ ID NOs: 12-20.

TABLE 2

| | |
|---|---|
| 277-gr__VL, (humanized) variable light chain | SEQ ID NO: 2 |
| 277-33__VL: (humanized) variable light chain | SEQ ID NO: 3 |
| 277-35__VL: (humanized) variable light chain | SEQ ID NO: 4 |
| 277-42__VL, (humanized) variable light chain | SEQ ID NO: 5 |
| 277-44__VL, (humanized) variable light chain | SEQ ID NO: 6 |
| 277-48__VL, (humanized) variable light chain | SEQ ID NO: 7 |
| 277-51__VL, (humanized) variable light chain | SEQ ID NO: 8 |
| 277-64__VL, (humanized) variable light chain | SEQ ID NO: 9 |
| 277-67__VL, (humanized) variable light chain | SEQ ID NO: 10 |
| 277-gr__VH, (humanized) variable heavy chain | SEQ ID NO: 12 |
| 277-33__VH: (humanized) variable heavy chain | SEQ ID NO: 13 |
| 277-35__VH: (humanized) variable heavy chain | SEQ ID NO: 14 |
| 277-42__VH, (humanized) variable heavy chain | SEQ ID NO: 15 |
| 277-44__VH, (humanized) variable heavy chain | SEQ ID NO: 16 |
| 277-48__VH, (humanized) variable heavy chain | SEQ ID NO: 17 |
| 277-51__VH, (humanized) variable heavy chain | SEQ ID NO: 18 |
| 277-64__VH, (humanized) variable heavy chain | SEQ ID NO: 19 |
| 277-67__VH, (humanized) variable heavy chain | SEQ ID NO: 20 |

Exemplary humanized antibodies of the present invention are those that have the light and heavy chain sequences as set forth in the following table. IgG1-KO has two mutations in the Fc region, Leu234Ala and Leu235Ala to reduce effector function.

TABLE 3

| | |
|---|---|
| 277-gr (Light Chain, IgG1) | 21 |
| 277-gr (Heavy Chain, IgG1) | 22 |
| 277-gr (Heavy Chain, IgG1-KO) | 23 |
| 277-33 (Light Chain, IgG1) | 24 |
| 277-33 (Heavy Chain, IgG1) | 25 |
| 277-33 (Heavy Chain, IgG1-KO) | 26 |
| 277-35 (Light Chain, IgG1) | 27 |
| 277-35 (Heavy Chain, IgG1) | 28 |
| 277-35 (Heavy Chain, IgG1-KO) | 29 |
| 277-42 (Light Chain, IgG1) | 30 |
| 277-42 (Heavy Chain, IgG1) | 31 |
| 277-42 (Heavy Chain, IgG1-KO) | 32 |
| 277-44 (Light Chain, IgG1) | 33 |
| 277-44 (Heavy Chain, IgG1) | 34 |
| 277-44 (Heavy Chain, IgG1-KO) | 35 |
| 277-48 (Light Chain, IgG1) | 36 |
| 277-48 (Heavy Chain, IgG1) | 37 |
| 277-48 (Heavy Chain, IgG1-KO) | 38 |
| 277-51 (Light Chain, IgG1) | 39 |
| 277-51 (Heavy Chain, IgG1) | 40 |
| 277-51 (Heavy Chain, IgG1-KO) | 41 |
| 277-64 (Light Chain, IgG1) | 42 |
| 277-64 (Heavy Chain, IgG1) | 43 |
| 277-64 (Heavy Chain, IgG1-KO) | 44 |
| 277-67 (Light Chain, IgG1) | 45 |
| 277-67 (Heavy Chain, IgG1) | 46 |
| 277-67 (Heavy Chain, IgG1-KO) | 47 |
| 277 L-CDR1 | 48 |
| 277 L-CDR2 | 49 |
| 277 L-CDR3 | 50 |
| 277 H-CDR1 | 51 |
| 277 H-CDR2 | 52 |
| 277 H-CDR3 | 53 |

3. Epitope Information

Materials

Water (Sigma Aldrich, P/N 37877-4L)

Acetonitrile (Sigma Aldrich, P/N 34998-4L)

Formic acid (Fluka, P/N 94318)

Urea (Sigma Aldrich, P/N 51456-500G)

TCEP-HCl—10 g (Thermo Scientific—Pierce, P/N 20491)

Sodium Phosphate Disbasic (Sigma Aldrich, P/N 57907-100G)

Sodium Phosphate Monobasic (Sigma Aldrich, P/N S8282-500G)

ACQUITY UPLC BEH C18 VanGuard Pre-column, 130 Å, 1.7 µm, 2.1 mm×5 mm (Waters Technologies Corp, 186003975)

Poroszyme® Immobilized Pepsin Cartridge, 2.1 mm×30 mm (Life Technologies Corp, 2313100)

Acquity UPLC BEH C18 Column 1.7 um, 1 mm×50 mm (Waters, 186002344)

Solvent A: 0.1% Formic acid/99% water/1% acetonitrile
Solvent B: 0.1% Formic acid/5% water/95% acetonitrile
Water Buffer: $H_2O$ 10 mM sodium phosphate pH 7.4
Deuterium Buffer: $D_2O$ 10 mM sodium phosphate pH 7.4
Quench Buffer: Water 8 M Urea, 0.4M TCEP-HCl In epitope mapping control samples, the antigen is run with and without antibody. To determine the list of antigen peptides, this protocol is first run using Water buffer in place of Deuterium buffer. 4 uL of sample is mixed with 40 uL of Deuterium buffer. This mixture was incubated at 20° C. for multiple time points (1, 2, and 4 minutes). Then 40 uL of the mixture was transferred to 40 uL of 4° C. quench buffer (4M Urea, 0.4M Tcep-HCl) and mixed. 60 uL of the quenched protein is injected, where it's digested on the pepsin column for 2 minutes by flowing 200 uL/mL of solvent A: 0.1% Formic acid/99% water/1% acetonitrile. The subsequent peptides are desalted on the Vanguard Pre-column for 3 minutes. The peptic peptides are sent to a BEH C18 reversed phase column inside the column/valve temperature controlled compartment. A gradient solvent system consisting of solvent A: 0.1% Formic acid/99% water/1% acetonitrile and solvent B: 0.1% Formic acid/5% water/95% acetonitrile is utilized. The percentage of solvent B is increased from 10% to 15% at 5.1 minute, to 50% at 11 minutes, to 90% at 11.5 minutes held to 12.5 minutes, to 0% B at 13 minutes held to 14 minutes. The chromatographic separation took place at 4° C. at a flow rate of 180 µl/min. After chromatographic separation the sample entered the Thermo Scientific Orbitrap Fusion mass spectrometer operated in positive electrospray ionization mode. The employed method included activation types of CID and ETD when identifying control peptides, utilizing a resolution of 120,000, a minimum signal of 10,000, an isolation width of 1.0 and a normalized collision energy of 35.0V. The S-lens RF level was set at 60%. For control peptides data collection type is profile for the full MS scan and centroid for the CID MS/MS data. For Deuterated samples, no MS/MS is collected. Data is collected over a mass range of 280-1800 Da. For raw LC-MS/MS fragmentation data analysis, control samples (with CID and ETD MS/MS) were analyzed using Proteome Discover 1.4 (Thermo Scientific) and PMi Byonic (Protein Metrics) against the given sequence to generate a list of peptides and retention times. Raw data files were preprocessed and converted to ASCII format using proprietary in-house SHARC software. Identified peptides were then matched and summarized using proprietary in-house SHAFT software. Epitopes were determined by differences in average mass shift induced by binding after Deuterium labeling. On a peptide level, protection greater than 0.4 Da was considered significant.

Figure 1:
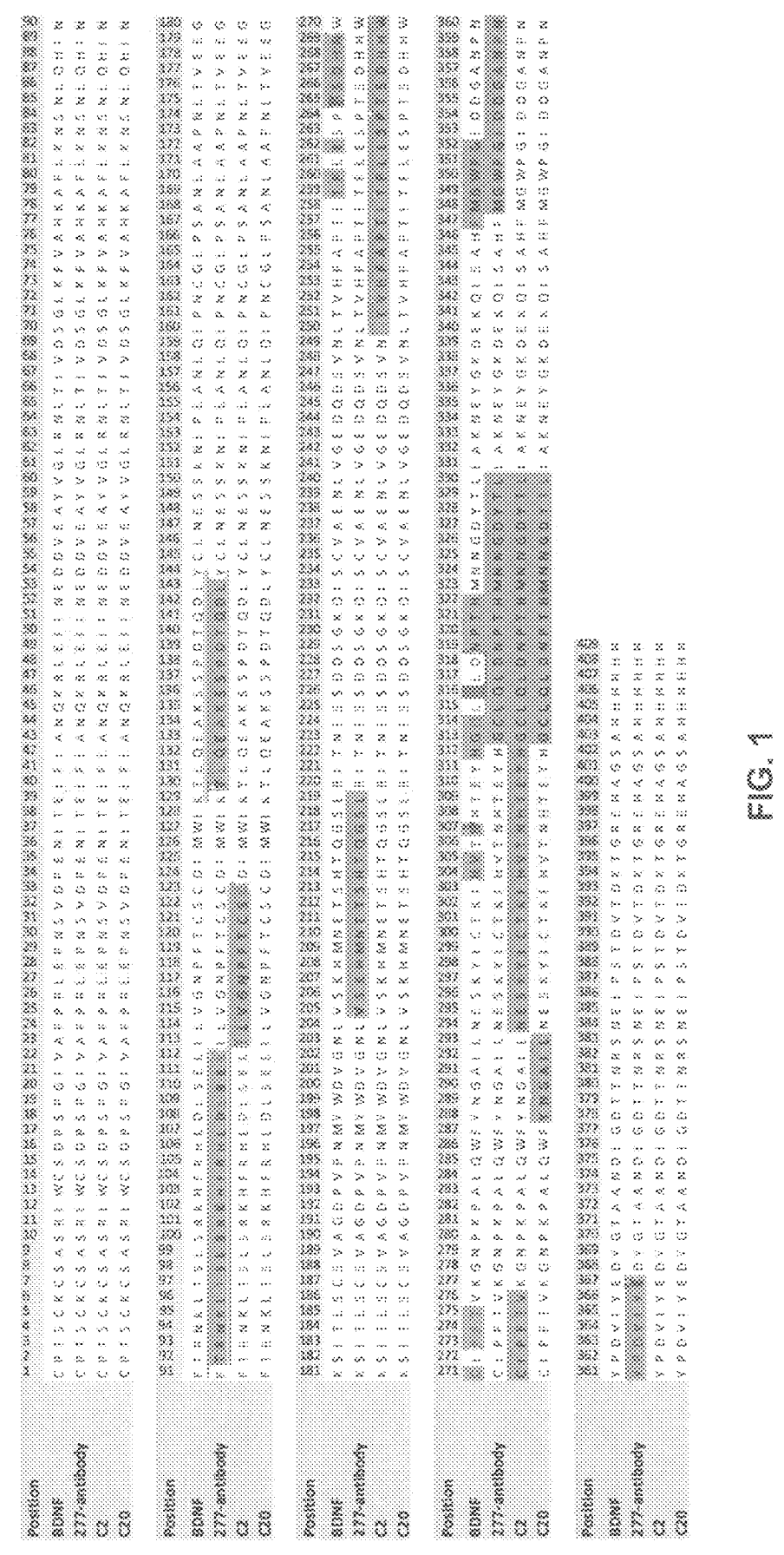

Results of the epitope mapping are shown for BDNF, 277-antibodies, (C2) (US20100196390), and (C20) (US20100150914) in FIG. 1. Specific binding sites for each molecule to the extracellular domain of human TrkB with SEQ ID NO: 54 are highlighted in dark grey. Compared to the natural ligand BDNF the 277-antibodies bind to distinct new epitopes.

4. Sequence Liabilities in the CDRs

Sequences of the CDRs are checked for the presence for any potential liabilities such as N-glycosylation sites, strong Deamidation motifs (NG, NS, NH, NA, ND, NT, NN), Aspartate isomerization motifs (DG), Fragmentation motifs (DG, DS), Cysteine. These amino acids or motifs can undergo chemical reaction and confer undesired heterogeneity to the product, also with the possibility of negatively impacting target binding and function. For these reason, it is preferred to remove such amino acids or motifs (if any) from the CDRs.

The CDRs of the mouse lead and humanized sequences are free of such potential liability motifs.

TABLE 4

| Antibody | D003/277 | C2 | C20 | 29D7 or TAM-163 |
|---|---|---|---|---|
| Liabilities | 0 | 2 | 3 | 6 |

5. Immunogenicity

Immunogenicity of sequences is evaluated in silico with an algorithm provided through a license by the company Epivax. EpiMatrix Treg-adj Score take into consideration T cell epitopes and Treg epitopes. The lower the immunogenicity score, the less likely a sequence to be immunogenic. In general, a negative score is considered low risk of immunogenicity, while a positive score is viewed as indication for potential immunogenicity.

TABLE 5

| VLs | Epivax score | VHs | Epivax score |
|---|---|---|---|
| 277-gr_VL | −24 | 277-gr_VH | −46 |
| 277-33_VL | −31 | 277-33_VH | −32 |
| 277-35_VL | −31 | 277-35_VH | −26 |
| 277-42_VL | −27 | 277-42_VH | −26 |
| 277-44_VL | −14 | 277-44_VH | −49 |
| 277-48_VL | −24 | 277-48_VH | −29 |
| 277-51_VL | −31 | 277-51_VH | −22 |
| 277-64_VL | −28 | 277-64_VH | −44 |
| 277-67_VL | −14 | 277-67_VH | −44 |
| C2_VL | −2 | C2_VH | −21 |
| C20_VL | +9 | C20_VH | +20 |
| TAM163_VL | −51 | TAM163_VH | −19 |

6. Affinity:

Surface Plasmon Resonance (SPR) technology was used to to determine the binding affinity of 277-antibodies, C2 (US20100196390), and C20 (US20100150914), and TAM-163 (WO2015173756) to Hu-TrkB-His. The experiment was performed on PrateOn XPR36 instrument.

Method: The running buffer for this experiment and all dilutions (except where stated) were done in PBS-T-EDTA with 0.01% Tween20 [100 µl of 100% Tween20 was added to 2 L of PBS-T-EDTA to make final Tween 20 concentration of 0.01%]. The GLM sensorchip was normalized and preconditioned as per the manufacturer's recommendations. The sensorchip was activated with equal mixture of EDC/s-NHS in the horizontal direction for 300 sec at a flow rate of 30 µl/min and immobilized with Recombinant Protein A/G (60 µg/ml in 10 mM acetate pH 4.5) in the horizontal direction for 300 sec at a flowrate of 30 µl/min resulting in ~7100-7130 RU of Protein A/G on the surface. The sensorchip was deactivated with 1M ethanolamine HCl in the horizontal direction for 300 sec at a flowrate of 30 µl/min. The sensorchip was stabilized with 18 sec of 0.85% phosphoric acid at a flowrate of 100 µl/min 3 times horizontally and 3 times vertically. 277-antibody (0.6 µg/ml), C2 (2.1 µg/ml), C20 (1.2 µg/ml), and TAM-163 (5 µg/ml) were captured on the Protein A/G surface vertically for 70 sec at a flowrate of 30 µl/min resulting capture levels of ~615, 1390, 780, and 3380 RU, respectively. The baseline was stabilized by injecting PBS-T-EDTA for 60 sec at a flowrate of 100 µl/min horizontally and then a second injection of PBS-T-EDTA for 60 sec at a flowrate 100 µl/min and dissociation 120 sec horizontally. The analyte (Hu-TrkB-His) was injected horizontally over the captured antibody for 600 sec at a flowrate of 30 µl/min and a dissociation for 1800 sec. The concentrations of the analytes were 0 nM, 1.23 nM, 3.7 nM, 11.11 nM, 33.33 nM, and 100 nM. The surface was regenerated by injecting 0.85% phosphoric acid for 18 sec at a flowrate of 100 µl/min one time horizontally and one time vertically. PBS-T-EDTA was injected for 60 sec at a flowrate of 100 µl/min one time vertically. The interspot (interactions with sensor surface) and blank (PBS-T-EDTA with 0.01% Tween20 or 0 nM analyte) were subtracted from the raw data. Sensorgrams were then fit globally to 1:1 Langmuir binding to provide on-rate (ka), off-rate (kd), and affinity ($K_D$) values.

277-antibodies bind to Hu-TrkB-His with a ka of $1.93 \times 10^5$ 1/Ms, a kd of $3.51 \times 10^{-4}$ 1/s, and $K_D$ of 1.2 nM. C2 binds to Hu-TrkB-His with a ka of $2.32 \times 10^4$ 1/Ms, a kd of $3.39 \times 10^{-4}$ 1/s, and $K_D$ of 10.5 nM. C20 binds to Hu-TrkB-His with a ka of $1.29 \times 10^5$ 1/Ms, a kd of $6.13 \times 10^{-3}$ 1/s, and $K_D$ of 47.7 nM. TAM-163 does not bind to 100 nM Hu-TrkB-His.

TABLE 6

| mAb | human TrkB | | |
|---|---|---|---|
| | $k_a$ (1/Ms) | $k_d$ (1/s) | $K_D$ (nM) |
| TAM-163_anti-TrkB | no binding at 100 nM | | |
| C20_chimeric anti-TrkB huIgG1-KO_EX00077781 | 1.29E+05 | 6.13E-03 | 47.7 |
| anti-TrkB C2_HuIgG1ko (EX00077780) | 2.32E+04 | 3.39E-04 | 10.5 |
| Anti-TRKB 277 antibodies | 1.93E+05 | 3.51E-04 | 1.19 |

7. Non-Specific Binding:

A non-specific binding assay was developed using biosensor technology to determine if new biological entity (NBE) candidates have significant binding to unrelated charged proteins. In this assay, the antibodies are passed over two SPR surfaces, one coated with an unrelated negatively charged protein and one coated with an unrelated positively charged protein. When an NBE candidate displays significant non-specific binding to these surfaces, it is likely that the cause of binding is the presence of positive or negative charged surface patches on the candidate. Non-specific binding of NBE candidates may translate to poor pharmacokinetics (PK) and biodistribution and may also have downstream manufacturability impacts. The results of this assay are used in the context of a project specific risk assessment. The purpose of the assay is to reduce the risk of poor PK, lack of tissue target distribution, and difficulty in downstream manufacturing.

Objective is to determine whether or not 277-antibodies exhibit non-specific binding by collecting the binding sensorgrams of 277-antibodies and comparing it to those of the controls to assign a non-specific binding category as either favorable (green), acceptable (yellow), or unfavorable (red).

Method:

The experiment was performed on Biacore T200. The dilution, surface preparation, and binding experiments were performed at 25° C. in 1×HBS-EP buffer prepared from 10×HBS-EP. The flow rate for both the immobilization protocol and binding experiment was at 5 µL/min.

To prepare the surface for the non-specific binding experiment, chicken egg white lysozyme and trypsin inhibitor type 1-S from soybean were coupled manually to a series S CM5 chip with the surface density of 3000-5000 RU using the amine coupling kit according to the manufacture instructions. FC1 and FC2 were activated by injecting a 1:1 mixture of EDC and NHS for 7 min. The chicken egg white lysozyme surface was prepared on FC2 by injecting 150 µg/mL of chicken egg white lysozyme in 10 mM NaOAc, pH 5.5 for 5 min. FC1 and FC2 were deactivated by injecting 1 M ethanolamine-HCl for 7 min. FC1 was used as the reference surface. FC3 was activated by injecting a 1:1 mixture of EDC and HNS for 7 min. The trypsin inhibitor type 1-S from soybean surface was prepared on FC3 by injecting 300 µg/mL of trypsin inhibitor type 1-S from soybean in 10 mM NaOAc, pH 4.0 buffer for 20 min followed by a 7 min injection of 1 M ethanolamine-HCl to deactivate the flow cell. Anti-lysozyme polyclonal antibody, anti-trypsin inhibitor antibody, and a BI negative control were used as controls in the assay. The controls and antibodies were prepared at 1 µM in 1×HBS-EP buffer. The samples were injected over FC1, FC2, and FC3 surfaces with a 10 min association and 15 min dissociation. The surfaces were regenerated between each binding cycle by injecting 1 min of 0.85% phosphoric acid and 30 s of 50 mM NaOH at a flow rate of 50 µL/min followed by a stabilization period of 2 min with 1×HBS-EP buffer flowing over all surfaces. Anti-lysozyme polyclonal antibody and anti-trypsin inhibitor antibody were injected over the FC1, FC2, and FC3 at the beginning and end of experiment. The data was collected using Biacore T200 Control Software version 2.0.1 and analyzed using Biacore T200 Evaluation Software version 3.0.

The binding sensorgrams of the antibodies were compared to the BI negative control sensorgrams to determine the level of non-specific binding to chicken egg white lysozyme and trypsin inhibitor type 1-S from soybean surfaces.

The data shows that 277-antibody does not significantly bind to unrelated charged proteins; specifically chicken egg white lysozyme and trypsin inhibitor type 1-S from soybean. 277-antibody was classified as favorable (green) when comparing the binding response and shape of the curves in relation to the controls. Therefore, it is postulated that 277-antibody will pose little risk in terms of pharmacokinetics, biodistribution, and manufacturing based on off-targeting of charged species.

TABLE 7

| Sample | ~4400 RU Lysozyme Surface | ~2300 RU Trypsin Inhibitor Surface |
|---|---|---|
| Anti-TRKB 277 antibodies | No binding | No binding |

8. Potency (SY5Y) and Efficacy

Differentiation of SH-SY5Y Cells to a Neuronal Phenotype

SH-SY5Y (ATCC® CRL-2266™) cells are cultured in DMEM:F12 (Lonza #BE12-719F) with 15% Fetal bovine serum in a 175 cm2 tissue culture flask (Corning #353112). For cell seeding the flask is washed one time with D-PBS (Lonza #17-512Q) and the cells are detached with 37° C. pre-warmed Accutase solution (A6964 SIGMA). After 3 min incubation at room temperature cells can be affiliated with a 10 ml pipet and transferred to a 15 ml Falcon tube. Cells are counted and 6000 cells in 100 µl DMEM:F12 with 15% FBS per well are seeded in a collagen-I coated 96-well plate (BD Biosciences #354407). Cells are maintained in a humidified incubator at 37° C., 5% $CO_2$. After 8 hrs, 100 µl of a 6 µM solution of retinoic acid (Sigma #R2625) is added to each well. The final retinoic acid concentration is 3 µM. After 48 hrs and 96 hrs, an additional retinoic acid stimulation is necessary. To this end, 100 µl medium per well is removed and 100 µl fresh medium with 6 µM retinoic acid is added. After 7 days of differentiation the SH-SY5Y cells have a dopaminergic-like phenotype and are ready to use.

Stimulation and Lysis of Differentiated SH-SY5Y Cells

Medium from the wells was exchanged with 80 µl pre-warmed DMEM-F12 with 0.2% BSA. The plate was incubated at room temperature for 15 min. Peptides and antibodies were diluted in DMEM-F12 with 0.2% BSA. All dilutions were prepared with low-binding tips, tubes and plates. The cells were stimulated by adding 20 µl of the corresponding peptide/antibody for 45 min at room temperature. During the incubation time the cell lysis buffer was prepared in a 15 ml Falcon tube on ice: 1 ml 10× Triton X-100 lysis buffer 8.7 ml $H_2O$ 1 tablet complete mini, protease inhibitor 100 µl phosphatase inhibitor cocktail 2 100 µl phosphatase inhibitor cocktail 3 100 µl 1 mM PMSF. After cell stimulation the medium was removed and 30 µl ice cold lysis buffer was added per well. The plate was coated with a top seal and incubated on ice for 20 min. Afterwards the plate was mixed on an Eppendorf plate shaker with 500 rpm for 5 min.

For this step all materials and solutions are stored on ice. The 96-Well plate with lysed cells is centrifuged with 235 g for 10 s and stored on ice. AlphaLISA Immunoassay Buffer (PerkinElmer #AL000C) is prepared by dilution of 260 µl 10× stock solution in 2340 µl $H_2O$. pNTRK2 acceptor beads (PerkinElmer #CUSM81822; beads coated by Perkin Elmer with antibody from CellSignaling CST #4621 clone C50F3) are diluted in AlphaLISA Immunoassay Buffer to a final concentration of 10 µg/ml. NTRK2 biotin antibody (PerkinElmer #CUSM81820; labeled by Perkin Elmer with antibody from CellSignaling CST=#4609 clone C17F1) are diluted in AlphaLISA Immunoassay Buffer to a final concentration of 1 nM and Streptavidin-donor beads (PerkinElmer #6760002S) are diluted in AlphaLISA Immunoassay Buffer to a final concentration of 20 µg/ml. 5 µl of pNTRK2 acceptor beads and 2.5 µl of cell lysate per well is transferred to a white small volume 384-well plate (Greiner #784075) with flat bottom and centrifuged with 235 g for 10 s and stored for 45 min at room temperature in the dark. After the incubation 2.5 µl NTRK2 biotin antibody per well is added and the plate is centrifuged with 235 g for 10 s and stored for 45 min at room temperature in the dark. Finally, 2.5 µl Streptavidin-donor beads per well is added and the plate is centrifuged with 235 g for 10 s and stored for 30 min at room temperature in the dark. Immediately afterwards the plate is measured with an EnVision plate reader using the AlphaScreen protocol (filter 570 nm #244 and mirror #444).

Determination of ERK1/2 Phosphorylation

Measurement of ERK 1/2 (Thr202/Tyr204) phosphorylation were performed with 8 µl cell lysate according manufactures protokoll (AlphaScreen SureFire p-ERK 1/2 (Thr202/Tyr204) Kit (PerkinElmer #TGRES10k))

Determination of AKT1/2/3 Phosphorylation

Measurement of Akt 1/2/3 (Thr308) phosphorylation were performed with 8 µl cell lysate according manufactures protokoll ((AlphaScreen SureFire p-Akt 1/2/3 (Thr308) kit (Perkin Elmer #TGRA3S10K)).

Several TrkB antibodies of the invention were analysed for their potency to activate TrkB as well as initiate downstream signalling. Also included were the natural ligand BDNF and the antibodies C2 and C20. The TrkB antibodies of the present invention were on average ten times more potent in activating TrkB than the natural ligand BDNF. Compared to the antibodies C2 and C20 the TrkB antibodies of the invention were on average three times to fifteen times more potent. The downstream signalling p-ERK and AKT1/2/3 were fully in line with these measurements for the TrkB activation and showed similar improved potency of the inventive TrkB antibodies.

TABLE 8

| Compound | EC50 pM [mean ± SD] |
|---|---|
| | TrkB-P |
| BDNF | 430 [±254] |
| 277-gr (IgG1) | 39 [±18] |
| 277-gr (IgG1-KO) | 46 [±27] |
| 277-64 (IgG1) | 53 [±41] |
| 277-64 (IgG1-KO) | 44 [±23] |
| C2 | 134 [±72] |
| C20 | 654 [±180] |
| | p-ERK 1/2 (Thr202/Tyr204) |
| BDNF | 301 [±279] |
| 277-gr (IgG1) | 30 [±12] |
| 277-gr (IgG1-KO) | 47 [±42] |
| 277-64 (IgG1) | 38 [±11] |
| 277-64 (IgG1-KO) | 56 [±72] |
| C2 | 103 [±56] |
| C20 | 238 [±36] |
| | AKT 1/2/3-P (T308) |
| BDNF | 255 [±179] |
| 277-gr (IgG1) | 23 [±0] |
| 277-gr (IgG1-KO) | 39 [±22] |
| 277-64 (IgG1) | 25 [±3] |
| 277-64 (IgG1-KO) | 22 [±1] |
| C2 | 132 [±76] |
| C20 | 430 [±111] |

9. Gene Expression

A next generation sequencing analysis (data not shown) was performed for differentiated SH-SY5Y cells after stimulation with several TrkB agonists. To validate the results the most regulated genes were chosen with regard to synaptic plasticity and subsequently the changes were analyzed again via qPCR. ARC, VGF, EGR1 are known markers for synaptic plasticity. Synaptic plasticity is the process by which specific patterns of synaptic activity result in changes in synaptic strength. In FIG. 2 the stimulation of differentiated SH-SY5Y cells with BDNF or agonistic antibodies increases the amount of ARC, VGF, EGR1 mRNA expression which can be a marker for increased synaptic plasticity. The mRNA expression of NTRK2 is not affected by stimulation with BDNF or agonistic antibodies. The changes in expression pattern induced by BDNF and D003 are overall very similar. These results confirmed the data from the next generation sequencing analysis.

In specific, SH-SY5Y cells were differentiated for 7 days in 6-well cell culture plate (SIGMA #Corning CLS3516). After differentiation, cells were stimulated in serum free DMEM:F12 with 0.2% BSA with control IgG [10 nM], BDNF [10 nM] and D003 [10 nM] for 6 hrs in a humidified incubator at 37° C., 5% CO2. Afterwards cells were washed once with pre-warmed 1×D-PBS and mRNA isolation was performed followed manufactures instruction (Qiagen #74104 RNeasy Mini Kit). The transcription of the mRNA to cDNA was performed followed manufactures instruction (Qiagen #205310 QuantiTect Rev. Transcription Kit). cDNA was used for TaqMan Real-Time PCR Assays based on 5' Nuclease probes (ThermoFischer Scientific) on a 7900HT Fast Real-Time PCR System (Applied Biosystems). Delta CT values were calculated based on the CT value of ACTB (CT=18.18).

TaqMan Gene Expression assays from ThermoFischer Scientific:
- ACTB—actin beta: Hs01060665_g1; Cat. #4331182
- NTRK2—neurotrophic receptor tyrosine kinase 2: Hs00178811_m1; Cat. #4331182
- ARC—activity regulated cytoskeleton associated protein: Hs01045540_g1; Cat. #4331182
- VGF—nerve growth factor inducible: Hs00705044_s1, Cat. #4331182
- EGR1—early growth response 1: Hs00152928_m1; Cat. #4331182

10. Rabbit Intravitreous (Ivt) Pharmacokinetic Study

New Zealand White female rabbits (1.7-2 kg body weight) were acclimatized >15 days prior to the start of the study. Antibody 277 was prepared sterile at 20 mg/mL and 1 mg (in 50 µL buffer: 60 mM sodium acetate, 150 mM NaCl, pH 5.0) was injected bilaterally into the vitreous of anesthetized animals. At various time points, 2 animals were euthanized and ocular tissues consisting of aqueous humor, vitreous and retina were collected and frozen pending analysis. Blood samples were taken on various time points (FIG. 3), centrifuged and plasma frozen pending analysis.

The quantification of the antibody was performed by ELISA. For each tissue type, a calibration curve of the antibody (triplicates ranging from 0.5-100 ng/mL) was prepared in the same buffer as the samples and included in every plate. Absorption was measured at 405 nm using a SpectraMax 340PC-384 photometer and data analysis performed using SoftMaxPro6.5.

Figure 3:
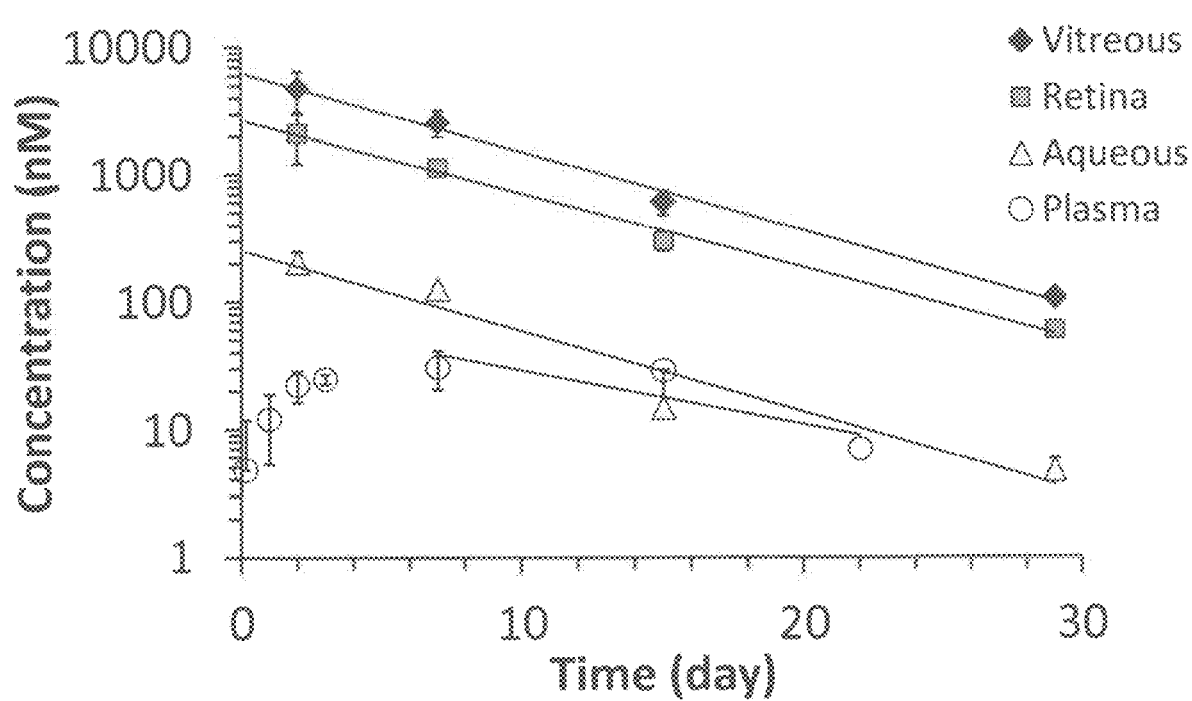
FIG. 3: Plot of the concentration of 277-antibody in ocular compartments as indicated and plasma after ivt injection of 1 mg of 277-antibody into rabbit eyes as a function of time.

The concentration of 277-antibody is depicted in FIG. 3 showing the concentration in various ocular compartments as indicated and plasma after ivt injection of 1 mg of 277-antibody into rabbit eyes as a function of time. The calculated ocular and plasma half-lifes are listed in the Table below.

TABLE 9

| $t_{1/2}$ (days) | | | |
|---|---|---|---|
| Vitreous | Aqueous | Retina | Plasma |
| 4.9 | 4.8 | 5.2 | 7.0 |

The calculated half-lives were 4.9, 4.8, 5.2, and 7.0 days in vitreous, aqueous humor, retina, and plasma, respectively. These half-lives are similar to those reported in the literature for the clinically used recombinant humanized monoclonal IgG1 antibody Avastin (anti-VEGF, bevacizumab, Bakri et al., Opthalmology, 2007), which were also confirmed experimentally in-house. These results were as expected, since the intravitreal clearance of full length IgGs depends mainly on their molecular size, which is similar for our antibody 277 and Avastin. Therefore, the human PK, including the ocular half-life of antibody 277 and Avastin is expected to be similar. The reported human ocular half-life of Avastin is 9.73±1.48 days (Hutton-Smith, 2016).

11. Ivt Injection Frequency of IgG1 Antibodies

Figure 4:
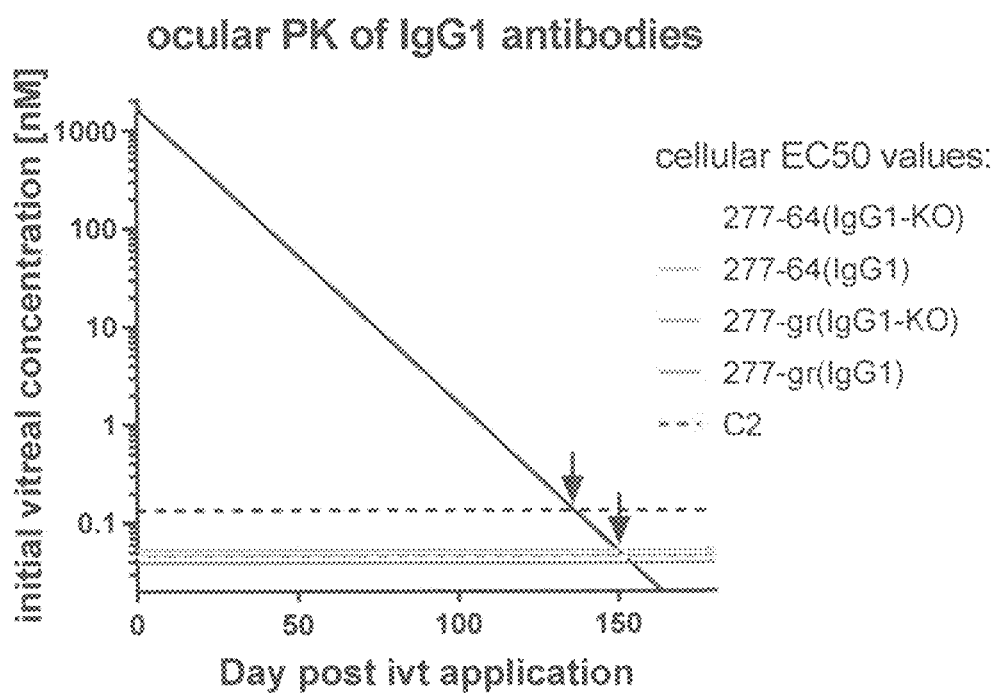
FIG. 4: Calculated ocular PK of IgG1 antibodies. Y-axis shows the vitreal concentration and x-axis the days post ivt application. The time post ivt injection to reach the vitreal concentration equivalent to the $EC_{50}$ is indicated by arrows.

Based on the in vivo data obtained in the pharmacokinetic study (Example 10) as well as the potency data obtained in SH-SY5Y cells the human ocular PK (vitreal concentration over time) of IgG1 antibodies was investigated and calculated based on the well-established one-compartment kinetics regarding ocular clearance of biomolecules. For the calculation, the following parameters were used: a human ocular half-life of $t_{1/2}$=10 days as reported for Avastin and also supported by the in vivo data shown in example 10; a molecular weight of 149 KDa as for full-length IgG1 antibodies, and an amount of ivt injected antibody of 1 mg (see FIG. 4). Since the ocular PK is predominantly driven by the molecular weight, the same plot of ocular PK is obtained for all five antibodies.

To estimate an ivt injection frequency, it was assumed that in vivo efficacy could be maintained at vitreal concentrations≥cellular $EC_{50}$ as determined from the TrkB-phosphorylation assays in SH-SY5Y cells (Example 8). The time post ivt injection to reach the vitreal concentration equivalent to the $EC_{50}$ is indicated by arrows in FIG. 4. Based on this consideration, the time to reach such a vitreal concentration after injection of 1 mg of antibody is summarized in the following table for each antibody:

TABLE 10

| Compound | Time post ivt to reach $C_{vitreous} = EC_{50}$ [days] |
|---|---|
| 277-gr (IgG1) | 154 |
| 277-gr (IgG1-KO) | 151 |
| 277-64 (IgG1) | 150 |
| 277-64 (IgG1-KO) | 152 |
| C2 | 136 |

For example, after injecting 1 mg of C2 into the human eye, a vitreal concentration corresponding to the $EC_{50}$ of C2 (TABLE 10) is reached after 136 days (i.e. after 136 days, the next ivt injection would be needed). For comparison, in case of 277-64 (IgG1), this time would extend to 150 days post ivt injection. In this case, the next ivt injection would be needed 14 days later as for C2. Targeting a minimal efficacious dose of values 10-fold higher than $EC_{50}$ would decrease the time between ivt injections, however, the time difference in injection frequency between C2 and the other antibodies listed in TABLE 10 above would remain the same.

The injection volume that can be administered to the eye is severely limited. At the same time repetitive injections in the eye are needed for treatment of eye conditions. Improving the half-life of the antibody is one way to extend the time between injection intervals but as mentioned is predominantly driven by the molecular weight of the molecule. As has been shown in vivo in example 10 and in SH-SY5Y cells in example 8, by providing an improved and more potent antibody injection intervals can be extended serving the patients need to receive less frequent injections in the eye.

12. Neuroprotective and Neuroregenerative Effects of an Agonistic TrkB Antibody in STZ-Induced Diabetic Rats None of the 277-antibodies are rodent cross-reactive, therefore in vivo proof-of-concept and efficacy studies were performed with the TrkB activating antibody C2 as surrogate-tool antibody to test the hypothesis that a TrkB activating approach i) provides neuroprotection ('neuroprotective approach'), and ii) provides reactivation of dysfunctional neurons/circuitries ('regeneration approach'). Both approaches were addressed in several studies. As animal disease models the streptozotocin (STZ)-induced diabetic rat model was utilized which is characterized by loss of pancreatic beta-cells, low insulin levels, stable hyperglycemia and consequently neuronal dysfunction in the retina.

Animal Study

Male Brown Norway rats (BN rats) were obtained from Charles River (Germany). Animals were housed in groups of 2 in IVCs at controlled temperature and humidity conditions, with a 12 h light/dark cycle (lights out between 6 p.m. and 6 a.m.). They were fed ad libitum with pelleted diet no. 3438 from Provimi Kliba (Switzerland) and had free access to tab water. Animals were acclimatized to their environment for one week before start of the study. The age of the rats was 6-8 weeks at start of the in-life phase of the study. Hyperglycemia was induced by i.p. injections of STZ (65 mg/kg body weight; Sigma #S0130-1G). Non- or poorly responding animals were not included into the study, i.e. animals with blood glucose concentrations <20 mM at day 5 post STZ application. Body weight and blood glucose levels were monitored regularly. Animals were dosed by a single ivt injection of C2 (50 µg in 4.6 µL) or the control antibody anti-2,4,6-trinitrophenyl (anti-TNP) (50 µg in 4.5 µL) at day 36 post STZ application. Retinal function was assessed via electroretinography (ERG) recordings, and animals were sacrificed after the final recording by an overdose of i.p.-administered pentobarbital.

Dosing and Intravitreal Injections

Figure 5:
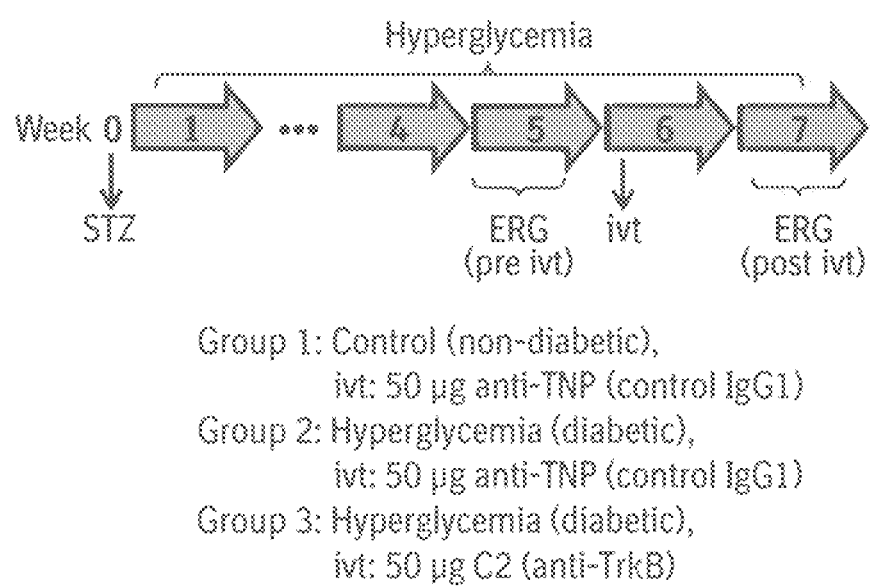
FIG. 5: Study overview including animal groups and time course. At week 5, a baseline ERG assessment (pre ivt application) was performed to evaluate the extent of hyperglycemia-induced neuronal dysfunction in the retina. Group 1 and Group 2 received ivt injections of an IgG1 control antibody anti-2,4,6-trinitrophenyl (anti-TNP) which did not cause any effects on retinal function. Eyes of group 3 were treated with C2 (an anti-TrkB agonistic surrogate antibody). Retinal function was again evaluated at week 7 (post ivt).

The study overview is depicted in FIG. 5. For ivt injections, rats were anesthetized with 2.5-3% isoflurane (Forene; Abbvie). A drop of 4 mg/ml oxybuprocainhydrochlorid (Novesine; Omnivision) was administered as a topical local anesthesia. 4.6 µL of C2 stock solution (10.9 mg/mL; buffer: 20 mM sodium citrate, 115 mM NaCl, pH 6.0) was ivt injected into each eye of hyperglycemic rats (group 3, n=24 eyes, FIG. 5), resulting in an injected dose of ~50 µg/eye. As control, 4.5 µL of anti-anti-2,4,6-trinitrophenyl stock solution (11.2 mg/mL; buffer 20 mM sodium citrate, 115 mM NaCl, pH 6.0) was ivt injected into eyes of non-diabetic and diabetic control rats (group 1, n=24 eyes, and group 2, n=22 eyes, FIG. 5), resulting in an injected dose of ~50 µg/eye. Ivt injections were performed under a dissecting microscope. The antibody solution was delivered with a 34-gauge needle (fitted on a 10 µl Hamilton glass syringe) into the vitreous just behind the limbus, and the general quality of injection was controlled by funduscopy (using the Micron IV Retinal Imaging Microscope, Phoenix Research Labs).

Electroretinography

Electroretinography (ERG) is a non-invasive electrophysiological technique to assess light-induced electrical activity of different retinal neurons, and allows for quantifying different aspects of retinal function such as dim light or color vision. ERGs were measured as the potential change between a corneal and a reference electrode using the Espion E3 ERG recording system (Diagnosys LLC). Prior to ERG recordings, animals were dark-adapted for at least 2 h, and anesthetized by i.p. injection of ketamine (Ketanest, ca. 100 mg/kg) and xylazin (Rompun, ca. 5 mg/kg). The animals were placed on a heated stage to maintain the body temperature constant at 37° C. Pupils were dilated with 1% cyclopentolate-HCl and 2.5% phenylephrine. A drop of Methocel 2% solution (OmniVision) was placed on the cornea to prevent eyes from drying and cataract development during recordings. Recordings were performed simultaneously from both eyes with gold loop electrodes. The reference electrode was a toothless alligator clip wetted with Methocel and attached to the cheek of the animal. For electrical grounding, a clip was attached to the tail of the animal. ERG signals were sampled at 1 kHz and recorded with 0.15 Hz low-frequency and 500 Hz high-frequency cutoffs. The light stimuli consisted of brief full-field flashes delivered by a set of light-emitting diodes (duration, <4 ms). All flashes were produced by a Ganzfeld stimulator (ColorDome; Diagnosys), either in darkness or on steady green or red background light.

ERG Protocols

ERG responses were first recorded from dark-adapted animals (for isolating rod-driven responses), followed by recordings from animals adapted to red background light (50 cd/m2, for isolating UV cone-driven ERG responses) and subsequently adapted to green background light (25.5 cd/m$^2$, for isolating M cone-driven responses). In case of dark-adapted ERGs, responses were evoked by a series of flashes ranging from $1 \cdot 10^{-5}$ to 0.1 cd·s/m$^2$. For flashes with the luminance of $1 \cdot 10^{-5}$ and $3 \cdot 10^{-5}$ cd·s/m$^2$, responses of 20 trials were averaged. For flashes between $1 \cdot 10^{-4}$ up to 0.05 cd·s/m$^2$, responses of 10 trial were averaged, and for the final flash of 0.1 cd·s/m$^2$, 8 trials were averaged. Intervals between individual flashes were chosen to ensure that the retina completely recovered from each flash (no indications of flash-induced reduction of response amplitudes or shortening of implicit times). Based on these criteria, the inter-flash intervals were 2 s for the $1 \cdot 10^{-5}$ and $3 \cdot 10^{-5}$ cd·s/m$^2$ flashes, 5 s for flashes between $1 \cdot 10^{-4}$ up to 0.05 cd·s/m$^2$, and 10 s for the flash of 0.1 cd·s/m$^2$.

For recordings of UV cone-driven responses, animals were light-adapted to the red background light for 2 min. Light responses were evoked by UV flashes of 0.02, 0.04, 0.08, 0.17, 0.35, 0.83, 1.66, 2.90, and 4.15 µW/m$^2$. For recordings of M cone-driven responses, animals were light-adapted to the green background light for 2 min. Light responses were evoked by green flashes of 0.25, 0.1, 1.0, 5.0, 50, and 150 cd·s/m$^2$. For UV and green flashes, responses of 10 trials were averaged with inter-flash intervals of 3 s.

Data Analysis

To determine ERG b-wave amplitudes (positive depolarizing response predominantly originating from bipolar cells), ERG data were processed and analyzed using the MATLAB software (version R2014a; MathWorks). The oscillatory potentials (small high-frequency wavelets superimposing the b-wave) were removed from the signals by 55 Hz fast Fourier transform low-pass frequency filtering because oscillatory potentials can affect the amplitude and position of the b-wave peak, especially under light-adapted conditions. The b-wave amplitude was calculated from the bottom of the a-wave response (negative deflection mostly originating from photoreceptor activity) to the peak of the b-wave peak. The b-wave implicit time was measured as the time after the flash stimulus needed to reach the peak of the b-wave.

The amplitudes of b-wave as a function of the stimulus intensity were fitted by the following equation using a least-square fitting procedure (GraphPad Prism, Version 6.01):

$$R = \frac{R_{max} I^n}{(I^n + I_h^n)} \qquad \text{(Equation 1)}$$

with R as the response amplitude, $R_{max}$ as the saturating response amplitude, I the flash intensity, $I_h$ the semi-saturating flash intensity and n as Hill coefficient.

Light sensitivity, S, was defined as the ratio between saturating response amplitude, $R_{max}$, and semi-saturating flash intensity, $I_h$.

S and $R_{max}$ values were normalized to the mean values of non-diabetic controls obtained for week 5, pre ivt, and for week 7, post ivt treatment, respectively.

For analysis of rod-driven b-wave implicit times, the mean implicit time of non-diabetic control animals was determined for b-waves evoked by flashes of $1\cdot10^{-5}$, $3\cdot10^{-5}$, $1\cdot10^{-4}$ and $2\cdot10^{-4}$ cd·s/m$^2$ (the corresponding implicit times are very similar). For each study group, the relative change to the mean value of controls was calculated for the flash intensities above and averaged, yielding the mean relative change in b-wave implicit time.

For analysis of UV cone-driven b-wave implicit times, the relative changes in implicit time to the mean value of controls were calculated for b-wave responses evoked by flash intensities of 0.042, 0.083, 0.166 and 0.348 μW/cm$^2$, and averaged.

For analysis of M cone-driven b-wave implicit times, the relative changes in implicit time to the mean value of controls were calculated for b-wave responses evoked by flash intensities of 1, 5, 50 and 150 cd·s/m$^2$, and averaged.

The rod-driven a-wave response was determined at the peak of the a-wave (the negative signal deflection immediately following the light stimulus) evoked by the flash of 0.1 cd·s/m$^2$.

Results

At week 5 post diabetes induction, baseline ERG recordings were performed to quantify the extent of neuronal dysfunction in the retina prior to ivt treatment (see also FIG. 5). Based on these ERG results, it was ensured that the two diabetic (hyperglycemic) groups displayed a similar distribution of retinal dysfunction (which received a follow-up ivt treatment either with the control IgG1 anti-2,4,6-trinitrophenyl-group 2—or the TrkB agonistic IgG1 C2—group 3). Generally, all ivt treatments were well tolerated and no adverse events were observed. Blood glucose was stable at ~5 mM in non-diabetic control rats (group 1, n=12) over the course of the study. In STZ-induced diabetic animals (group 2 and 3, each n=12), blood glucose concentrations reached levels >20 mM after ~4 days post STZ treatment, and did not decline below 20 mM over the course of the study. Ivt treatment with C2 or the control IgG1 anti-2,4,6-trinitrophenyl did not have any effects on blood glucose levels.

Figure 6:
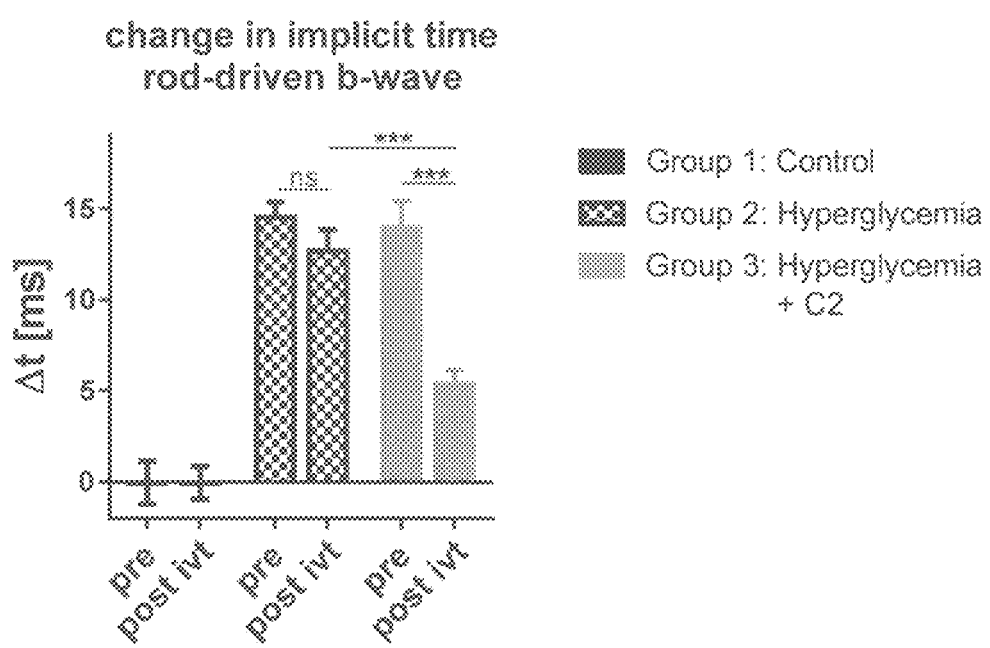
FIG. 6: Changes in rod-driven b-wave implicit times relative to the mean implicit time of the control group, at baseline (pre ivt) and 1 week post ivt application (see FIG. 5 for a study overview). The non-diabetic control group 1 (black, n=23 eyes investigated) and the hyperglycemic group 2 (dotted, n=21 eyes investigated) received ivt injections with a control IgG1. Group 3 received ivt treatment with C2 (n=24 eyes investigated). Data are mean+SEM. ns, not significant; *, $p<0.05$; , $p<0.01$; *, $p<0.001$; pre ivt differences between the hyperglycemic groups 2 and 3 and the control group 1 are significant (statistics omitted for clarity; one-way ANOVA with Tukey's multiple comparisons test).

Rod-Driven b-Wave Implicit Time:

The b-wave implicit time is a measure for the speed of the light-induced electrical response in the retina (predominantly on the level of bipolar cells and photoreceptor-to-bipolar cell synaptic transmission). The implicit time is defined as the time needed to reach the response amplitude after light flash stimulation. The effects of hyperglycemia and ivt treatment are summarized in FIG. 6. Changes in implicit time relative to the mean implicit time measured from control rats were calculated for the data obtained pre ivt treatment (baseline ERG assessment) and post ivt treatment. There was a robust increase in implicit time by ~14 ms in the two hyperglycemic groups pre ivt treatment, indicating a hyperglycemia-induced slow-down of b-wave response kinetics, i.e. a reduced speed of rod-driven retinal processing. Ivt injection of the control IgG1 anti-2,4,6-trinitrophenyl did not have any significant effects on implicit time in the non-diabetic control group and the hyperglycemic group (group 1, black bars, and group 2, dotted bars in FIG. 6, post ivt, respectively). However, ivt treatment with the TrkB activator C2 clearly resulted in a diminished delay in implicit time (group 3, grey bar in FIG. 6, post ivt). On average, ivt treatment with C2 caused a significant speed-up of b-wave responses by ~9 ms (i.e. the delay in implicit time was shortened from 14 ms down to 5 ms).

Figure 7:
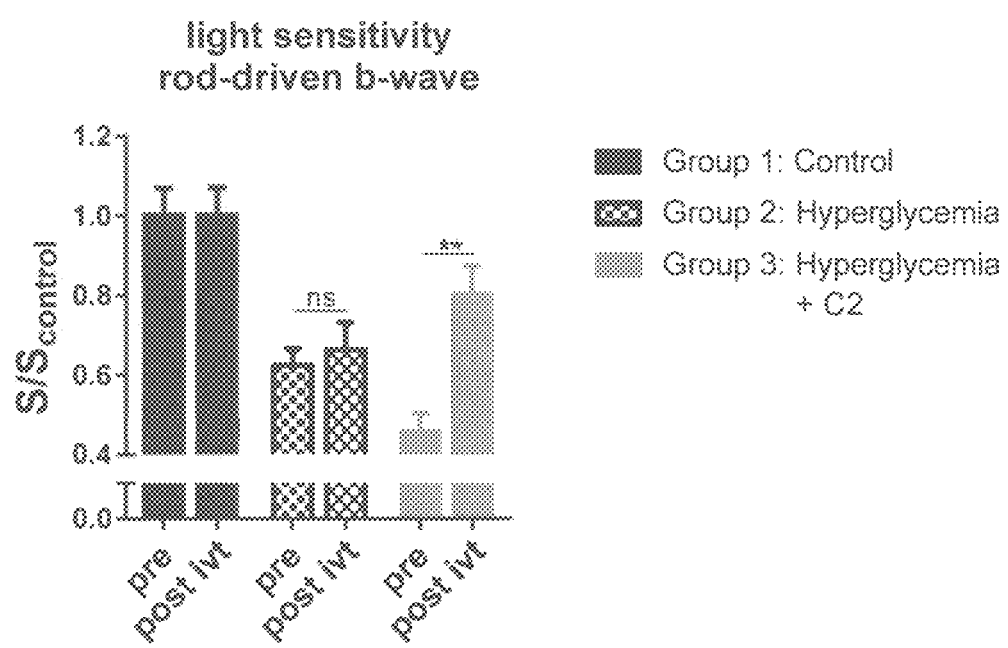
FIG. 7: Light sensitivities, S, of rod-driven b-waves normalized to the mean light sensitivities of the control group, $S_{control}$, at baseline (pre ivt) or 1 week post ivt application (see FIG. 5 for a study overview). The non-diabetic control group 1 (black, n=23 eyes investigated) and the hyperglycemic group 2 (red, n=20 eyes investigated) received ivt injections with a control IgG1. Group 3 received ivt treatment with C2 (n=24 eyes investigated). Data are mean+SEM. ns, not significant; *, $p<0.05$; , $p<0.01$; *, $p<0.001$; pre ivt differences between the hyperglycemic groups 2 and 3 and the control group 1 are significant (statistics omitted for clarity; one-way ANOVA with Tukey's multiple comparisons test).

Rod-Driven b-Wave Light Sensitivity:

The light sensitivity of rod-driven b-wave ERG responses is a measure for the number of neurons participating in the rod-driven retinal pathway, and their sensitivity towards light stimuli in order to produce depolarizing light responses. Light sensitivities were normalized to the mean light sensitivities of control rats (group 1, pre and post ivt treatment) and are plotted in FIG. 7. Normalized light sensitivities were decreased ~40-50% in the hyperglycemic animals (pre ivt treatment, group 2 and 3). Ivt injection of the control IgG1 did not have any significant effects on the light sensitivities of control rats (group 1) or hyperglycemic rats (group 2). Importantly, ivt treatment with the TrkB activator C2 significantly increased the light sensitivity by ~30% (group 3, grey, post ivt compared to pre ivt).

Figure 8:
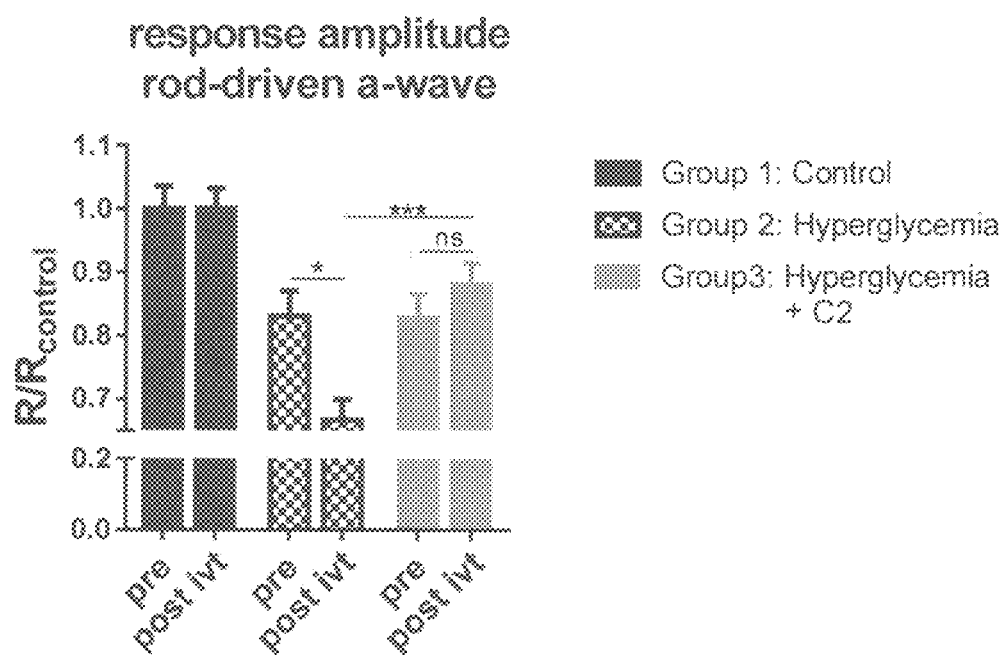
FIG. 8: Rod-driven a-wave responses evoked by a 0.1 $cd \cdot s/m^2$ light flash, R, normalized to the mean response of the controls, at baseline (pre ivt) or 1 week post ivt application (see FIG. 5 for a study overview). The non-diabetic control group 1 (black, n=23 eyes investigated) and the hyperglycemic group 2 (red, n=20 eyes investigated) received ivt injections with a control IgG1. Group 3 received ivt treatment with C2 (n=24 eyes investigated). Data are mean+SEM. ns, not significant; *, $p<0.05$; , $p<0.01$; *, $p<0.001$; pre ivt differences between hyperglycemic groups 2 and 3 and control group 1 are significant (statistics omitted for clarity; one-way ANOVA with Tukey's multiple comparisons test).

Rod-Driven a-Wave Responses:

The rod-driven a-wave response is a measure for the size of rod photoreceptor light responses evoked by a light flash. The rod-driven a-wave responses were normalized to the mean values obtained from control rats (group 1, pre and post ivt treatment) and are plotted in FIG. 8. Normalized saturating response amplitudes were decreased by ~17% in the hyperglycemic animals (group 2 and 3, pre ivt treatment). Ivt injection of the control IgG1 did not have any significant effects on the normalized a-wave responses of control rats (group 1, black) or hyperglycemic rats (group 2, dotted), with the latter displaying a further decline of the a-wave response in the course of the study. However, ivt treatment with the TrkB activator C2 (group 3, grey) could fully prevent the further reduction of a-wave responses as observed for the hyperglycemic group 2.

Figure 9:
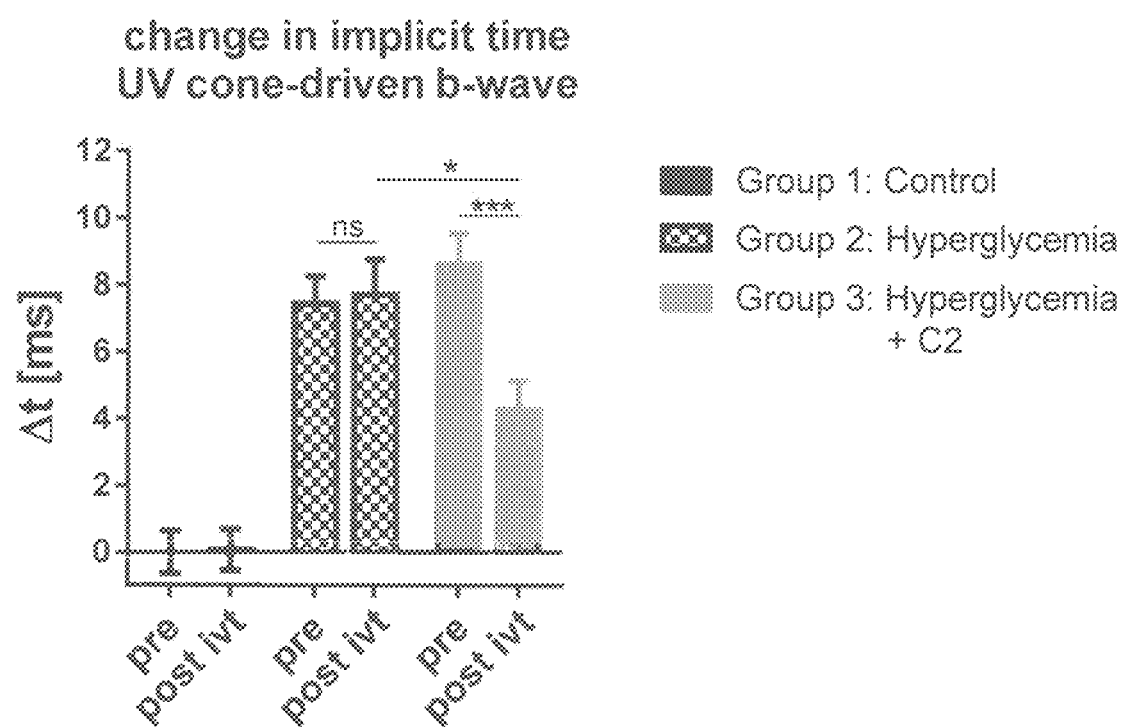
FIG. 9: Changes in UV cone-driven b-wave implicit times relative to the mean implicit time of the control group, at baseline (pre ivt) and 1 week post ivt application (see FIG. 5 for a study overview). The non-diabetic control group 1 (black, n=24 eyes investigated) and the hyperglycemic group 2 (red, n=22 eyes investigated) received ivt injections with a control IgG1. Group 3 received ivt treatment with C2 (n=24 eyes investigated). Data are mean+SEM. ns, not significant; *, $p<0.05$; , $p<0.01$; *, $p<0.001$; pre ivt differences between hyperglycemic groups 2 and 3 and control group 1 are significant (statistics omitted for clarity; one-way ANOVA with Tukey's multiple comparisons test).
Figure 10:
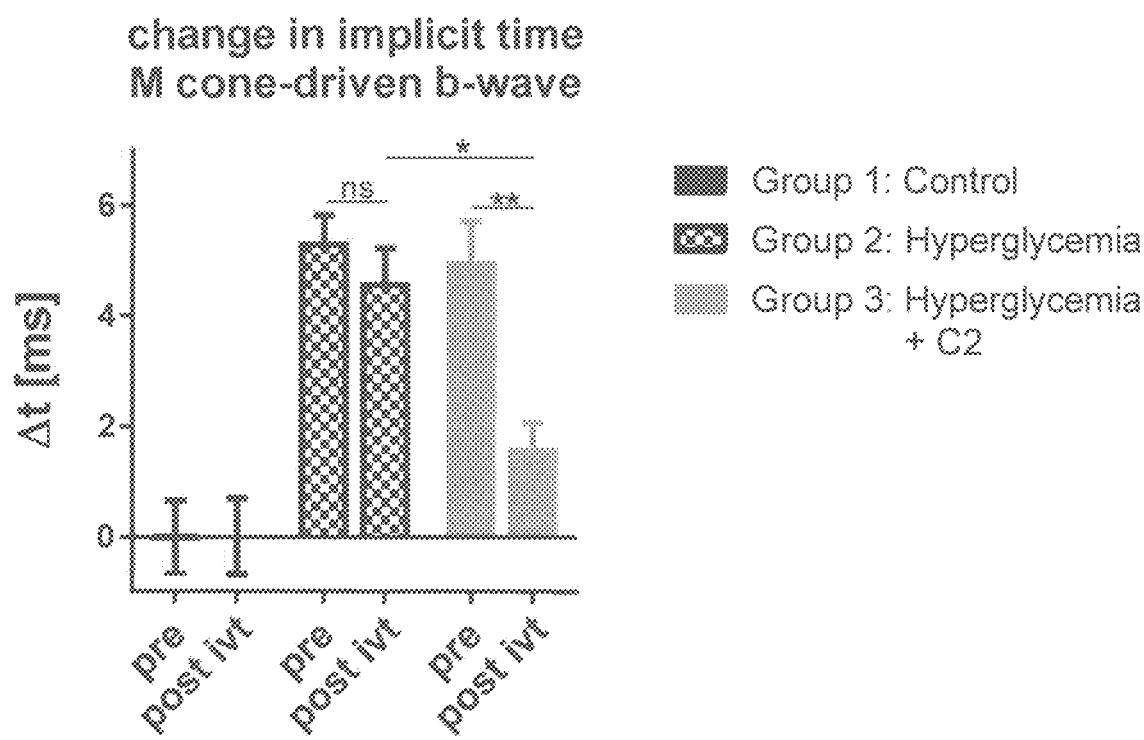
FIG. 10: Changes in M cone-driven b-wave implicit times relative to the mean implicit time of the control group, at baseline (pre ivt) and 1 week post ivt application (see FIG. 5 for a study overview). The non-diabetic control group 1 (black, n=24 eyes investigated) and the hyperglycemic group 2 (red, n=22 eyes investigated) received ivt injections with a control IgG1. Group 3 received ivt treatment with C2 (n=24 eyes investigated). Data are mean+SEM. ns, not significant; *, $p<0.05$; , $p<0.01$; *, $p<0.001$; pre ivt differences between hyperglycemic groups 2 and 3 and control group 1 are significant (statistics omitted for clarity; one-way ANOVA with Tukey's multiple comparisons test).

UV and M Cone-Driven b-Wave Implicit Times:

Changes in implicit time relative to the mean implicit time measured from control rats were calculated for the data obtained pre ivt treatment (baseline ERG assessment) and post ivt treatment. This analysis was performed for UV cone-driven b-wave implicit times (FIG. 9) and M cone-driven b-wave implicit times (FIG. 10). In case of UV cone-driven responses, there was a robust increase in implicit time by ~8 ms in the two hyperglycemic groups pre ivt treatment, whereas the increase of M cone-driven implicit time was ~5 ms in the hyperglycemic. These statistically significant effects indicate a hyperglycemia-induced slow-down of b-wave response kinetics and reduced speed of cone-driven retinal processing. Ivt injections of the control IgG1 did not have any significant effects on implicit time in the non-diabetic control group (group 1, black) or the hyperglycemic group (group 2, dotted), both for UV and M cone-driven b-wave implicit times. Ivt treatment with C2 (group 3, grey) shortened the implicit time by ~5 ms in case of UV cones (corresponding to a ~50% normalization of b-wave response kinetics), and an almost complete restoration of normal b-wave response kinetics in case of M cone-driven b-waves.

Figure 11:
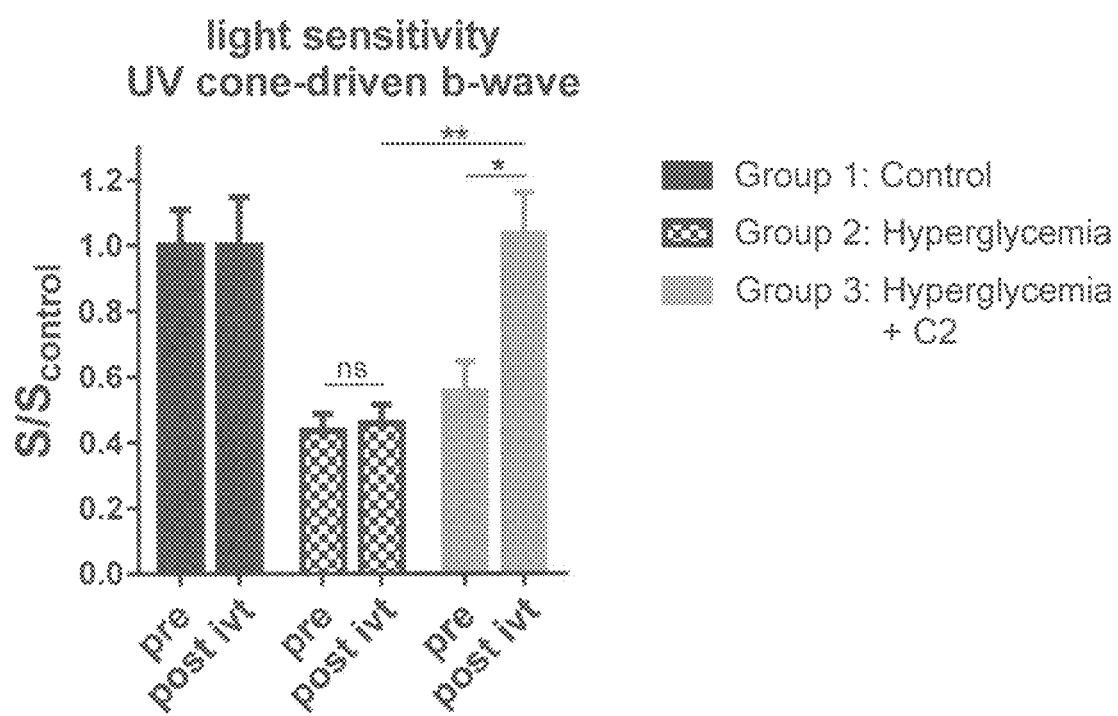
FIG. 11: Light sensitivities, S, of UV cone-driven b-waves normalized to the mean light sensitivities of the control groups, $S_{control}$, at baseline (pre ivt) or 1 week post ivt application (see FIG. 5 for a study overview). The non-diabetic control group 1 (black, n=22 eyes investigated) and the hyperglycemic group 2 (red, n=22 eyes investigated) received ivt injections with a control IgG1. Group 3 received ivt treatment with C2 (n=21 eyes investigated). Data are mean+SEM. ns, not significant; *, $p<0.05$; , $p<0.01$; *, $p<0.001$; pre ivt differences between hyperglycemic groups 2 and 3 and control group 1 are significant (statistics omitted for clarity; one-way ANOVA with Tukey's multiple comparisons test).

UV Cone-Driven b-Wave Light Sensitivity:

The light sensitivity of UV cone-driven b-wave ERG responses were assessed as described for rod-driven ERGs. Light sensitivities were normalized to the mean light sensitivities of control rats (group 1, pre and post ivt treatment) and are plotted in FIG. 11. Normalized light sensitivities were decreased by ~50% in the hyperglycemic animals at baseline (pre ivt). Ivt injection of the control IgG1 did not have any significant effects on the light sensitivities, whereas ivt treatment with C2 significantly increased the light sensitivity to the level observed in healthy control rats (group 3, grey).

M Cone-Driven Saturating b-Wave Response Amplitude

Figure 12:
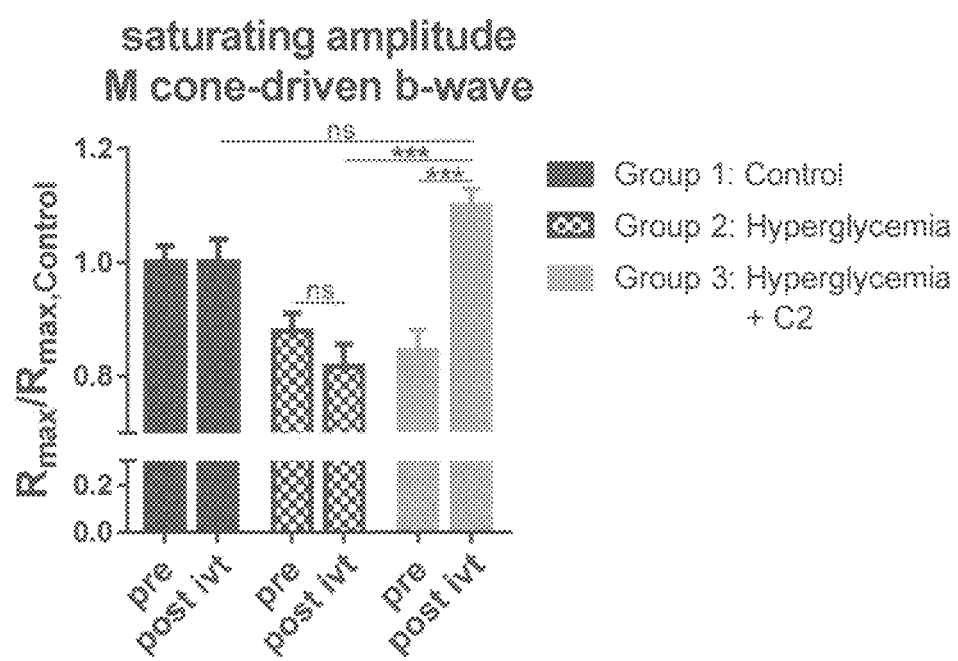
FIG. 12: Saturating response amplitudes, $R_{max}$, of M cone-driven b-waves normalized to the mean saturating response amplitude of controls, $R_{max}$, control, at baseline (pre ivt) or 1 week post ivt application (see FIG. 5 for a study overview). The non-diabetic control group 1 (black, n=24 eyes investigated) and the hyperglycemic group 2 (red, n=22 eyes investigated) received ivt injections with a control IgG1. Group 3 received ivt treatment with C2 (n=24 eyes investigated). Data are mean+SEM. ns, not significant; *, p<0.05; , p<0.01; *, p<0.001; pre ivt differences between hyperglycemic groups 2 and 3 and control group 1 are significant (statistics omitted for clarity; one-way ANOVA with Tukey's multiple comparisons test).

The effect of hyperglycemia on the M cone-driven b-wave light sensitivity is less pronounced than for the UV cone-driven b-waves (at the time points investigated). Yet, a significant impairment of M cone-driven b-wave saturating response amplitude could be observed at week 5 after onset of hyperglycemia (~15% reduction compared to non-diabetic control rats, FIG. 12). Ivt treatment with C2 could restore the saturating response amplitude to the level of controls (group 3, grey), while treatment with the control IgG$_1$ did not have any significant effects (group 2, dotted).

The Key Findings are Summarized Below:

TrkB activation causes neuroprotection and preservation of retinal function. Neuroprotection was shown in the STZ-induced diabetic rat model displaying hyperglycemia-induced neuronal dysfunction. It was shown that TrkB activation prevented the dysfunction of photoreceptors.

TrkB activation induces regain/improvement of neuronal function in the retina in the STZ-induced diabetic rat model after prolonged hyperglycemia, such as improved light response latency (i.e. shortened ERG b-wave implicit times), or improved rod- and cone-driven light sensitivities.

In summary, the pharmacology data provide evidence for the therapeutic concept that TrkB activation can improve/restore function of different neuronal cell types within the eye in different disease conditions.

TrkB activation also protects photoreceptors and the outer retina as demonstrated by the analysis of the ERG a-wave, which is a reflection of photoreceptor light responses. Similar to the results obtained for the ERG a-wave, contrast sensitivity of the eyes of diabetic rats is declining in the course of persisting hyperglycemia, whereas ivt treatment with the TrkB activator C2 fully preserves contrast sensitivity. Furthermore, the improvement in ERG b-wave light sensitivities of rod- and cone-driven light responses described above (reflecting the light sensitivities of the photoreceptor-to-bipolar cell synaptic transmission) further strengthens the concept that TrkB activation can improve/protect outer retina function including the photoreceptors.

13. BDNF Function in Combination Treatments

Cultivation of CHO Cells Expressing Human TrkB Receptor

CHO cells expressing human TrkB (hTrkB) receptor (ThermoFisher Scientific, #K1491) were cultured in DMEM (Lonza, #BE12-604F) supplemented with 10% fetal bovine serum, glutamax, non-essential amino acids, 20 mM HEPES, 5 µg/ml blasticidin and 200 µg/ml zeocin. Twenty four hours before stimulation, 5000 cells (30 µl) were seeded in each cavity of a 384 well clear tissue culture plate (BD Falcon, #353963) and incubated in a humidified incubator at 37° C. and 5% CO$_2$.

Analysis of ERK Phosphorylation in CHO Cells with hTrkB Receptor

Twenty four hours after seeding, the supernatant of the CHO/hTrkB cells was replaced with 40 µl room-temperature DMEM with 0.1% BSA but without other supplements. After 15 minutes, 10 µl DMEM/0.1% BSA with increasing concentrations of BDNF (1E-13 to 3E-8 mol/l), 277-antibody (1E-13 to 2.025E-8 mol/l), or C2-antibody (1E-13 to 2.025E-8 mol/l) alone or a combination of 1 nM BDNF with increasing concentrations of the 277- or C2-antibody (both 1E-13 to 2.025E-8 mol/l) was added in triplicate to stimulate ERK phosphorylation. After incubation for 45 minutes at room temperature, the supernatants were removed and the cells were lysed for 20 minutes on wet ice in 20 µl lysis buffer per well (1× Tryton lysis buffer (CellSignaling #9803-S), supplemented with complete mini protease inhibitor tablets (Roche #04693124001) and phosphatase inhibitor cocktail 2 (Sigma #P5726) and 3 (Sigma #P0044), and 1 mM PMSF (Sigma #93482)). Five microliters of the resulting lysate were used for quantification of ERK1/2 phosphorylation at T202/Y204 using a commercially available assay (Perkin Elmer #TGRES500), according to the manufacturer's instructions. Light emission of the acceptor beads, reflecting ERK phosphorylation, was recorded at 570 nm on a Perking Elmer EnVision microplate reader and prepared for presentation with GraphPad Prism (version 7), including the raw data (mean±SEM) and a non-linear regression (log(agonist) vs. response (three parameters)).

Figure 13A:
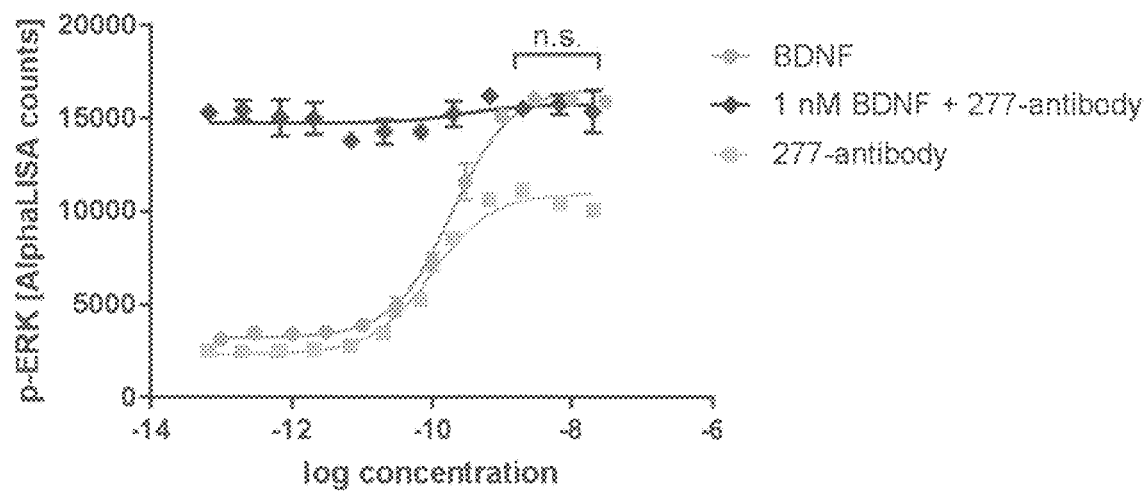
FIG. 13A: ERK-phosphorylation in CHO cells expressing human TrkB receptor after stimulation with BDNF, 277-antibody, or a combination of 1 nM BDNF with increasing concentrations of 277-antibody. Data (symbols) are expressed as mean±SEM (for some points, the error bars are shorter than the height of the symbol); connecting lines reflect non-linear regression (log(agonist) vs. response (three parameters)). One representative experiment of a series of three with independent cell batches is shown; n.s., non-significant difference between 1 nM BDNF alone and 1 nM BDNF with the indicated 277-antibody concentrations. #p<0.001 1 nM BDNF alone vs. 1 nM BDNF with indicated C2-antibody concentrations; one way ANOVA with multiple comparison test.
Figure 13B:
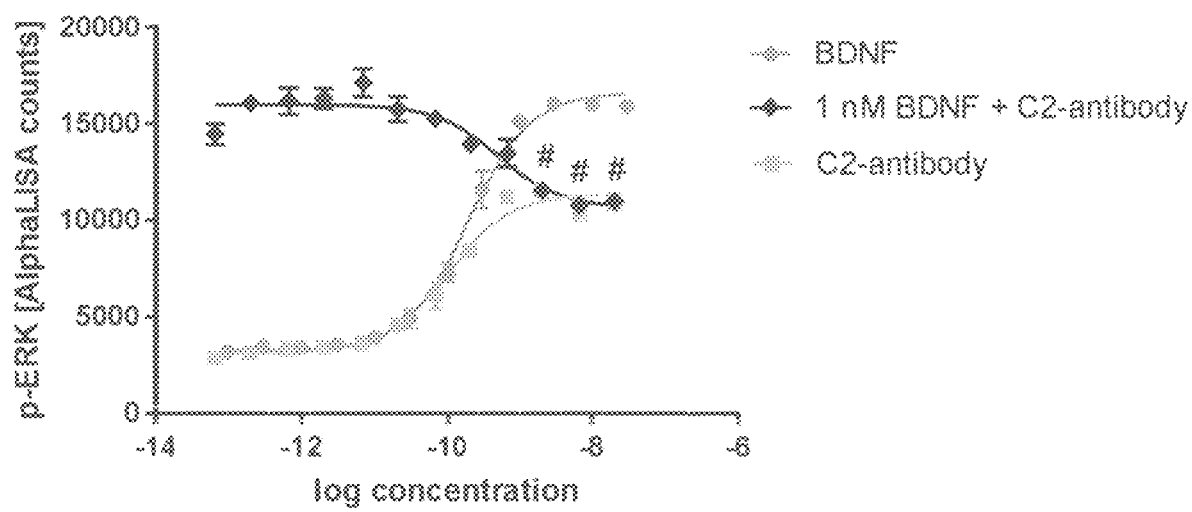
FIG. 13B: ERK-phosphorylation in CHO cells expressing human TrkB receptor after stimulation with BDNF, C2 antibody, or a combination of 1 nM BDNF with increasing concentrations of C2-antibody. Data (symbols) are expressed as mean±SEM (for some points, the error bars are shorter than the height of the symbol); connecting lines reflect non-linear regression (log(agonist) vs. response (three parameters)). One representative experiment of a series of three with independent cell batches is shown; n.s., non-significant difference between 1 nM BDNF alone and 1 nM BDNF with the indicated 277-antibody concentrations. #p<0.001 1 nM BDNF alone vs. 1 nM BDNF with indicated C2-antibody concentrations; one way ANOVA with multiple comparison test.

As shown in FIG. 13 the 277-antibody did not reduce BDNF induced ERK phosphorylation. Rising concentrations of the C2 antibody resulted in reduction of the BDNF induced ERK phosphorylation down to the level of C2 induced ERK phosphorylation. This may have significant impact on dosing of an anti-Trkb antibody in the eye where the antibodies are administered in high saturating concentrations to prolong the time until the next administration is necessary. The 277-antibody can be administered in high doses without interfering with existing BDNF induced ERK phosphorylation whereas the C2 antibody reduces existing BDNF induced ERK phosphorylation down to the level of the antibody.

14. Binding to Human VEGF In Vitro ELISA Assay

For the in vitro binding assay, MaxiSorp 96 well plates (Nunc #437111) were coated over night at 4° C. with 500 ng/ml human VEGF (R&D Systems #293-VE-050) or rat VEGF (R&D Systems #564-RV-050) in carbonate/bicarbonate buffer (3.03 g/l Na$_2$CO$_3$ and 6.00 g/l NaHCO$_3$, pH 9.6). Plates were washed three times with PBS-T (phosphate buffered saline (Invitrogen #70011-036) with 0.05% Tween20 (Sigma #P7949)) and then incubated with 1% BSA (Sigma #A3059) in PBS-T for three hours at room temperature to block unspecific binding. Plates were washed three times with PBS-T and then incubated with a 1:4 serial dilution of 1 µM Avastin (Roche clinic package), C2-antibody, 277-antibody, or a human IgG1 isotype control antibody in PBS-T overnight at 4° C. Plates were washed three times with PBS-T and then incubated with a 1:2000 dilution of Alexa fluor 647 goat anti-human IgG (Invitrogen #A21445) for two hours at room temperature. After three additional rounds of washing with PBS-T, light emission at 647 nm (reflecting antibody binding to VEGF) was recorded on a Perking Elmer EnVision microplate reader. Data were prepared for presentation with GraphPad Prism (version 7), including the raw data (mean±SEM) and a non-linear regression (log(agonist) vs. response (three parameters)).

Figure 14:
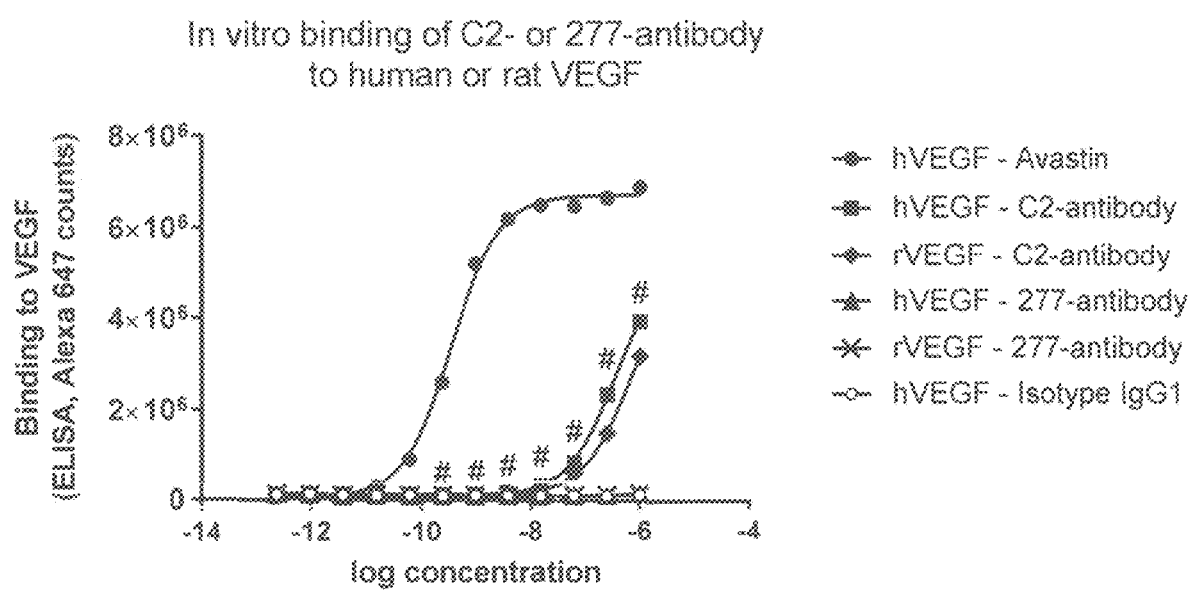
FIG. 14: Binding of 277-antibody or C2 antibody to human or rat VEGF in an in vitro ELISA assay. Data (symbols) are expressed as mean±SEM (note: the error bars are shorter than the height of the symbol); connecting lines reflect non-linear regression (log(agonist) vs. response (three parameters)). One representative experiment of a series of five independent experiments is shown. #p<0.01 hVEGF-C2 vs. hVEGF-Isotype IgG1 at the indicated concentrations (unpaired t-test).

As shown in FIG. 14 there was no statistically significant difference in human VEGF-binding between the 277 anti-TrkB antibody and the IgG1 isotype control antibody at antibody concentrations of up to 0.25 µM (unpaired t-test, $p>0.05$). In contrast, a statistically significant difference in human VEGF binding between C2 and the isotype control antibody was already observed at an antibody concentration of 0.24 nM (unpaired t-test, **$p<0.01$).

Such an unspecific binding to VEGF may cause e.g. unwanted side-effects, make difficult the control of doses for TrkB activation, or increase the amount of antibody needed to achieve the desired effect.

The invention claimed is:

1. A method for treatment of a subject suffering from eye disease, comprising:
   administering to the subject a therapeutically effective amount of an anti-TrkB antibody or the antigen-binding fragment thereof comprising:
   I.a. a light chain variable region comprising the amino acid sequence of SEQ ID NO: 48 (L-CDR1); the amino acid sequence of SEQ ID NO: 49 (L-CDR2); and the amino acid sequence of SEQ ID NO: 50 (L-CDR3); and
   I.b. a heavy chain variable region comprising the amino acid sequence of SEQ ID NO: 51 (H-CDR1); the amino acid sequence of SEQ ID NO: 52 (H-CDR2); and the amino acid sequence of SEQ ID NO: 53 (H-CDR3), or
   I.c. a heavy chain variable region comprising the amino acid sequence of SEQ ID NO: 55 (H-CDR1); the amino acid sequence of SEQ ID NO: 56 (H-CDR2); and the amino acid sequence of SEQ ID NO: 57 (H-CDR3), or
   I.d. a heavy chain variable region comprising the amino acid sequence of SEQ ID NO: 58 (H-CDR1); the amino acid sequence of SEQ ID NO: 59 (H-CDR2); and the amino acid sequence of SEQ ID NO: 60 (H-CDR3), or
   administering to the subject a therapeutically effective amount of an anti-TrkB antibody or the antigen-binding fragment thereof comprising:
   II.a. a variable light chain and a variable heavy chain comprising the amino acid sequences of SEQ ID NO: 2 and SEQ ID NO: 12, respectively, or
   II.b. a variable light chain and a variable heavy chain comprising the amino acid sequences of SEQ ID NO: 3 and SEQ ID NO: 13, respectively, or
   II.c. a variable light chain and a variable heavy chain comprising the amino acid sequences of SEQ ID NO: 4 and SEQ ID NO: 14, respectively, or
   II.d. a variable light chain and a variable heavy chain comprising the amino acid sequences of SEQ ID NO: 5 and SEQ ID NO: 15, respectively, or
   II.e. a variable light chain and a variable heavy chain comprising the amino acid sequences of SEQ ID NO: 6 and SEQ ID NO: 16, respectively, or
   II.f. a variable light chain and a variable heavy chain comprising the amino acid sequences of SEQ ID NO: 7 and SEQ ID NO: 17, respectively, or
   II.g. a variable light chain and a variable heavy chain comprising the amino acid sequences of SEQ ID NO: 8 and SEQ ID NO: 18, respectively, or
   II.h. a variable light chain and a variable heavy chain comprising the amino acid sequences of SEQ ID NO: 9 and SEQ ID NO: 19, respectively, or
   II.i. a variable light chain and a variable heavy chain comprising the amino acid sequences of SEQ ID NO: 10 and SEQ ID NO: 20, respectively, or
   administering to the subject a therapeutically effective amount of an anti-TrkB antibody or the antigen-binding fragment thereof comprising:
   III.a. a light chain comprising the amino acid sequence of SEQ ID NO: 21 and a heavy chain comprising the amino acid sequence of SEQ ID NO: 22 or 23, or
   III.b. a light chain comprising the amino acid sequence of SEQ ID NO: 24 and a heavy chain comprising the amino acid sequence of SEQ ID NO: 25 or 26, or
   III.c. a light chain comprising the amino acid sequence of SEQ ID NO: 27 and a heavy chain comprising the amino acid sequence of SEQ ID NO: 28 or 29, or
   III.d. a light chain comprising the amino acid sequence of SEQ ID NO: 30 and a heavy chain comprising the amino acid sequence of SEQ ID NO: 31 or 32, or
   III.e. a light chain comprising the amino acid sequence of SEQ ID NO: 33 and a heavy chain comprising the amino acid sequence of SEQ ID NO: 34 or 35, or
   III.f. a light chain comprising the amino acid sequence of SEQ ID NO: 36 and a heavy chain comprising the amino acid sequence of SEQ ID NO: 37 or 38, or
   III.g. a light chain comprising the amino acid sequence of SEQ ID NO: 39 and a heavy chain comprising the amino acid sequence of SEQ ID NO: 40 or 41, or
   III.h. a light chain comprising the amino acid sequence of SEQ ID NO: 42 and a heavy chain comprising the amino acid sequence of SEQ ID NO: 43 or 44, or
   III.i. a light chain comprising the amino acid sequence of SEQ ID NO: 45 and a heavy chain comprising the amino acid sequence of SEQ ID NO: 46 or 47,
   wherein the eye disease is geographic atrophy, age-related macular degeneration, diabetic retinopathy, diabetic macular edema, retinitis pigmentosa, inherited retinal dystrophy, inherited macular dystrophy, myopic degeneration, retinal vein occlusions, retinal artery occlusions, endophthalmitis, uveitis, cystoid macular edema, choroidal neovascular membrane secondary to any retinal diseases, optic neuropathies, glaucoma, retinal detachment, toxic retinopathy, radiation retinopathy, or traumatic retinopathy.

* * * * *